(12) United States Patent
Ouyang et al.

(10) Patent No.: US 11,287,414 B2
(45) Date of Patent: Mar. 29, 2022

(54) SAMPLE DISPENSER INCLUDING AN INTERNAL STANDARD AND METHODS OF USE THEREOF

(71) Applicant: Purdue Research Foundation, West Lafayette, IN (US)

(72) Inventors: Zheng Ouyang, West Lafayette, IN (US); He Wang, West Lafayette, IN (US); Nicholas E. Manicke, West Lafayette, IN (US); Robert Graham Cooks, West Lafayette, IN (US); Qian Yang, West Lafayette, IN (US); Jiangjiang Liu, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 15 days.

(21) Appl. No.: 16/936,683

(22) Filed: Jul. 23, 2020

(65) Prior Publication Data
US 2020/0355671 A1 Nov. 12, 2020

Related U.S. Application Data

(63) Continuation of application No. 15/357,048, filed on Nov. 21, 2016, now Pat. No. 10,761,083, which is a
(Continued)

(51) Int. Cl.
*G01N 33/49* (2006.01)
*G01N 1/28* (2006.01)
(Continued)

(52) U.S. Cl.
CPC ............ *G01N 33/492* (2013.01); *G01N 1/28* (2013.01); *G01N 1/286* (2013.01);
(Continued)

(58) Field of Classification Search
CPC .... G01N 1/28; G01N 1/286; G01N 33/48785; G01N 33/48714; G01N 33/491;
(Continued)

(56) References Cited

U.S. PATENT DOCUMENTS 3,000,836 A 9/1961 Ginsburg
3,334,233 A 8/1967 Veal
(Continued)

FOREIGN PATENT DOCUMENTS

CN 101820979 A 9/2010
CN 102414778 A 4/2012
(Continued)

OTHER PUBLICATIONS

Gaskell, Simon J., "Electrospray:Principles and Practice", Journal of Mass Spectometry, vol. 32 677-688 (1997)) (Year: 1997).*
(Continued)

*Primary Examiner* — David E Smith
(74) *Attorney, Agent, or Firm* — Brown Rudnick LLP; Adam M. Schoen

(57) ABSTRACT

The invention generally relates to a sample dispenser including an internal standard and methods of use thereof.

11 Claims, 71 Drawing Sheets

Related U.S. Application Data continuation of application No. 13/784,094, filed on Mar. 4, 2013, now Pat. No. 9,500,572, which is a continuation-in-part of application No. 13/265,110, filed as application No. PCT/US2010/032881 on Apr. 29, 2010, now Pat. No. 8,859,956.

(60) Provisional application No. 61/608,944, filed on Mar. 9, 2012, provisional application No. 61/308,332, filed on Feb. 26, 2010, provisional application No. 61/246,707, filed on Sep. 29, 2009, provisional application No. 61/174,215, filed on Apr. 30, 2009.

(51) Int. Cl.

| | | |
|---|---|---|
| *H01J 49/16* | (2006.01) | |
| *H01J 49/00* | (2006.01) | |
| *G01N 33/487* | (2006.01) | |
| *G01N 1/10* | (2006.01) | |

(52) U.S. Cl.
CPC . *G01N 33/48714* (2013.01); *G01N 33/48785* (2013.01); *G01N 33/491* (2013.01); *H01J 49/0009* (2013.01); *H01J 49/0027* (2013.01); *H01J 49/16* (2013.01); *G01N 1/10* (2013.01); *G01N 2001/2893* (2013.01)

(58) Field of Classification Search
CPC .......... G01N 33/492; G01N 2001/2893; H01J 49/009; H01J 49/0027; H01J 49/0031; H01J 49/16
See application file for complete search history.

(56) References Cited

U.S. PATENT DOCUMENTS

| | | | |
|---|---|---|---|
| 3,997,469 A | 12/1976 | Howle | |
| 4,235,838 A | 11/1980 | Redmore et al. | |
| 4,755,670 A | 7/1988 | Syka et al. | |
| 4,757,198 A | 7/1988 | Korte et al. | |
| 4,828,547 A | 5/1989 | Sahi et al. | |
| 4,885,076 A | 12/1989 | Smith et al. | |
| 4,957,640 A | 9/1990 | Treybig et al. | |
| 5,141,868 A | 8/1992 | Shanks et al. | |
| 5,152,177 A | 10/1992 | Buck et al. | |
| 5,223,226 A | 6/1993 | Wittmer et al. | |
| 5,288,646 A | 2/1994 | Lundsgaard et al. | |
| 5,583,281 A | 12/1996 | Yu | |
| 6,297,499 B1 * | 10/2001 | Fenn ................ | H01J 49/167 250/288 |
| 6,452,168 B1 | 9/2002 | McLuckey et al. | |
| 6,477,238 B1 | 11/2002 | Schneider et al. | |
| 6,627,881 B1 | 9/2003 | Bertrand et al. | |
| 6,645,399 B2 | 11/2003 | Ahn et al. | |
| 6,781,121 B1 * | 8/2004 | Davis ................ | H01J 49/025 250/281 |
| 6,958,475 B1 | 10/2005 | Colby | |
| 6,982,416 B2 | 1/2006 | Villinger et al. | |
| 6,992,284 B2 | 1/2006 | Schultz et al. | |
| 7,005,635 B2 | 2/2006 | Ahern et al. | |
| 7,010,096 B1 | 3/2006 | Wooding | |
| 7,154,088 B1 | 12/2006 | Blain et al. | |
| 7,171,193 B2 | 1/2007 | Hoffman | |
| 7,223,969 B2 | 5/2007 | Schultz et al. | |
| 7,259,019 B2 | 8/2007 | Pawliszyn et al. | |
| 7,384,793 B2 | 6/2008 | McCash et al. | |
| 7,384,794 B2 | 6/2008 | Pawliszyn | |
| 7,510,880 B2 | 3/2009 | Gross et al. | |
| 7,544,933 B2 | 6/2009 | Cooks et al. | |
| 7,564,027 B2 | 7/2009 | Finch et al. | |
| 7,714,281 B2 | 5/2010 | Musselman | |
| 7,915,579 B2 | 3/2011 | Chen et al. | |
| 7,930,924 B2 | 4/2011 | Krogh et al. | |
| 8,030,088 B2 | 10/2011 | McCash et al. | |
| 8,076,639 B2 | 12/2011 | Cooks et al. | |
| 8,188,424 B2 | 5/2012 | Baykut et al. | |
| 8,294,892 B2 | 10/2012 | Sardashti et al. | |
| 8,304,718 B2 | 11/2012 | Ouyang et al. | |
| 8,330,119 B2 | 12/2012 | Chen et al. | |
| 8,334,505 B2 | 12/2012 | Robinson et al. | |
| 8,421,005 B2 | 4/2013 | Musselman | |
| 8,481,922 B2 | 7/2013 | Musselman | |
| 8,704,167 B2 * | 4/2014 | Cooks ................ | H01J 49/10 250/282 |
| 8,710,437 B2 | 4/2014 | Cooks et al. | |
| 8,754,365 B2 | 6/2014 | Krechmer et al. | |
| 8,816,275 B2 | 8/2014 | Ouyang et al. | |
| 8,859,956 B2 * | 10/2014 | Ouyang ................ | G01N 1/00 250/288 |
| 8,859,958 B2 * | 10/2014 | Ouyang ................ | G01N 1/00 250/288 |
| 8,859,959 B2 * | 10/2014 | Ouyang ................ | H01J 49/04 250/288 |
| 8,859,986 B2 | 10/2014 | Cooks et al. | |
| 8,895,918 B2 * | 11/2014 | Cooks ................ | G01N 30/91 250/282 |
| 8,932,875 B2 | 1/2015 | Cooks et al. | |
| 8,937,288 B1 | 1/2015 | Cooks et al. | |
| 9,035,239 B1 | 5/2015 | Cooks et al. | |
| 9,087,683 B2 | 7/2015 | Girault et al. | |
| 9,105,458 B2 | 8/2015 | Trimpin et al. | |
| 9,165,752 B2 | 10/2015 | Cooks et al. | |
| 9,500,630 B2 * | 11/2016 | Cooks ................ | H01J 49/168 |
| 9,620,344 B2 | 4/2017 | Cooks et al. | |
| 9,733,228 B2 | 8/2017 | Cooks et al. | |
| 9,797,872 B2 * | 10/2017 | Cooks ................ | H01J 49/0431 |
| 9,941,105 B2 | 4/2018 | Cooks et al. | |
| 10,088,461 B2 | 10/2018 | Cooks et al. | |
| 10,197,547 B2 | 2/2019 | Cooks et al. | |
| 10,204,772 B2 | 2/2019 | Cooks et al. | |
| 10,571,453 B2 * | 2/2020 | Cooks ................ | H01J 49/10 |
| 10,622,198 B2 | 4/2020 | Cooks et al. | |
| 2002/0034827 A1 | 3/2002 | Singh et al. | |
| 2002/0055184 A1 | 5/2002 | Naylor et al. | |
| 2002/0123153 A1 | 9/2002 | Moon et al. | |
| 2003/0136918 A1 | 7/2003 | Hartley | |
| 2003/0141392 A1 | 7/2003 | Nilsson et al. | |
| 2003/0180824 A1 | 9/2003 | Mpock et al. | |
| 2003/0199102 A1 | 10/2003 | Ostrup | |
| 2004/0011954 A1 | 1/2004 | Park | |
| 2004/0075050 A1 | 4/2004 | Rossier et al. | |
| 2004/0126890 A1 * | 7/2004 | Gjerde ................ | G01N 1/40 436/53 |
| 2004/0245457 A1 | 12/2004 | Granger et al. | |
| 2005/0072917 A1 | 4/2005 | Becker | |
| 2005/0092910 A1 * | 5/2005 | Geromanos .......... | C12Q 1/6872 250/282 |
| 2005/0098720 A1 | 5/2005 | Traynor et al. | |
| 2005/0112635 A1 | 5/2005 | Gentle et al. | |
| 2005/0117864 A1 | 6/2005 | Dziekan et al. | |
| 2005/0247870 A9 | 11/2005 | Park | |
| 2006/0093528 A1 | 5/2006 | Banerjee et al. | |
| 2006/0118713 A1 | 6/2006 | Matsui et al. | |
| 2006/0192107 A1 | 8/2006 | DeVoe et al. | |
| 2006/0200316 A1 | 9/2006 | Kanani et al. | |
| 2006/0249668 A1 | 11/2006 | Goldberg et al. | |
| 2007/0003965 A1 | 1/2007 | Ramsay et al. | |
| 2007/0025881 A1 | 2/2007 | Thompson et al. | |
| 2007/0151232 A1 | 7/2007 | Dalla Betta et al. | |
| 2007/0187589 A1 | 8/2007 | Cooks et al. | |
| 2008/0083873 A1 | 4/2008 | Giardina | |
| 2008/0128608 A1 | 6/2008 | Northen et al. | |
| 2008/0179511 A1 | 7/2008 | Chen et al. | |
| 2008/0210856 A1 | 9/2008 | Eide et al. | |
| 2008/0272091 A1 | 11/2008 | Kovtoun | |
| 2008/0283742 A1 | 11/2008 | Takeuchi et al. | |
| 2009/0071834 A1 | 3/2009 | Hafeman et al. | |
| 2009/0090856 A1 * | 4/2009 | Grant ................ | G01N 33/6848 250/282 |
| 2009/0127454 A1 | 5/2009 | Ritchie et al. | |
| 2009/0152371 A1 | 6/2009 | Stark et al. | |
| 2009/0280300 A1 | 11/2009 | Craighead et al. | |

(56) References Cited

U.S. PATENT DOCUMENTS

| | | |
|---|---|---|
| 2009/0283693 A1 | 11/2009 | Hsu et al. |
| 2009/0306230 A1 | 12/2009 | Semikhodskii et al. |
| 2009/0309020 A1 | 12/2009 | Cooks et al. |
| 2010/0001181 A1 | 1/2010 | Moini |
| 2010/0019143 A1 | 1/2010 | Dobson et al. |
| 2010/0059689 A1 | 3/2010 | Horiike et al. |
| 2010/0108879 A1 | 5/2010 | Bateman et al. |
| 2010/0230587 A1 | 9/2010 | Marshall et al. |
| 2010/0301209 A1 | 12/2010 | Ouyang et al. |
| 2011/0108724 A1 | 5/2011 | Ewing et al. |
| 2011/0108726 A1 | 5/2011 | Hiraoka et al. |
| 2011/0133077 A1 | 6/2011 | Henion et al. |
| 2011/0192968 A1 | 8/2011 | Makarov et al. |
| 2011/0193027 A1 | 8/2011 | Mackenzie et al. |
| 2011/0210265 A1 | 9/2011 | Lozano et al. |
| 2012/0018629 A1 | 1/2012 | Eikel et al. |
| 2012/0119079 A1 | 5/2012 | Ouyang et al. |
| 2012/0153139 A1 | 6/2012 | Qian et al. |
| 2013/0023005 A1 | 1/2013 | Chen et al. |
| 2013/0112017 A1 | 5/2013 | Ouyang et al. |
| 2013/0112866 A1 | 5/2013 | Ouyang et al. |
| 2013/0112867 A1 | 5/2013 | Ouyang et al. |
| 2013/0181010 A1 | 7/2013 | Ouyang et al. |
| 2013/0273560 A1 | 10/2013 | Cooks et al. |
| 2013/0299694 A1 | 11/2013 | Sato et al. |
| 2014/0008532 A1 | 1/2014 | Ouyang et al. |
| 2014/0048697 A1 | 2/2014 | Cooks et al. |
| 2014/0165701 A1 | 6/2014 | Wu et al. |
| 2014/0183351 A1 | 7/2014 | Cooks et al. |
| 2015/0309001 A1 | 10/2015 | Cooks et al. |
| 2017/0343526 A1 | 11/2017 | Cooks et al. |
| 2019/0137473 A1 | 5/2019 | Cooks et al. |

FOREIGN PATENT DOCUMENTS

| | | |
|---|---|---|
| JP | 2011-007690 A | 1/2011 |
| WO | 2001/053819 A1 | 7/2001 |
| WO | 2003/104814 A2 | 12/2003 |
| WO | 2004/060278 A2 | 7/2004 |
| WO | 2008/065245 A1 | 6/2008 |
| WO | 2008/103733 A2 | 8/2008 |
| WO | 2009/023361 A2 | 2/2009 |
| WO | 2010/127059 A1 | 11/2010 |
| WO | 2012/094227 A2 | 7/2012 |
| WO | 2012/170301 A1 | 12/2012 |
| WO | 2014/120552 A1 | 8/2014 |

OTHER PUBLICATIONS

Nemes, et al, 2012, "Ambient mass spectrometry for in vivo local analysis and in situ molecular tissue imaging," TrAC-Trends in Analytical Chemistry 34, pp. 22-33, published in United Kingdom.
Non-Final Office Action issued in U.S. Appl. No. 15/483,132, dated Aug. 21, 2017, 11 pages.
International Preliminary Report on Patentability issued in International Application No. PCT/US2014/034767, dated Jan. 7, 2016, 7 Pages.
Office Action issued in U.S. Appl. No. 16/809,171, dated Jul. 30, 2020, 8 pages.
Oradu, et al., 2012, "Multistep Mass Spectrometry Methodology for Direct Characterization of Polar Lipids in Green Microalgae Using Paperspray Ionization", Anal. Chem., 10576-10585.
Partial Extended Search Report dated Jan. 12, 2017 in couterpart EP Application No. 10770301.9.
Ratcliffe et al., 2007, "Surface Analysis under Ambient Conditions Using Plasma-Assisted Desorption/Ionization Mass Spectrometry," Anal. Chem., 79, pp. 6094-6101.
Ren, et al., 2013, "Direct Mass Spectrometry Analysis of Untreated Samples Ultralow Amounts Using Extraction Nano-Electrospray", Analytical Methods, vol. 5, No. 23, pp. 6686-6692.
Second Examiner's Report issued in Canadian Application No. 2,759,987, dated Feb. 17, 2017, 8 pages.
Sokol, et al., 2011, "Miniature mass spectrometer equipped with electrospray and desorption electrospray ionization for direct analysis of organics from solids and solutions," Int. J. Mass Spectrom. 306, pp. 187-195.
Soparawalla, et al., 2011, "In situ analysis of agrochemical residues on fruit using ambient ionization on a handheld mass spectrometer," Analyst, 2011, 136, pp. 4392-4396.
Su, et al., 2013, "Quantitative Paper Spray Mass Spectrometry Analysis of Drugs of Abuse", The Analyst, vol. 138, No. 16, pp. 4443-4447.
Takats, et al., 2004, "Mass spectrometry sampling under ambient conditions with desorption electrospray ionization," Science 306, pp. 471-473, published in USA.
Thibodeaux, et al., 2011,"Marine Oil Fate: Knowledge Gaps, Basic Research, and Development Needs; a Perspective based on the Depwater Horizon Spill" Environmental Engineering Science, 28, pp. 87-93.
Valentine, et al., 2010, "Propane respiration jump-starts microbial response to deep oiil spill", Science, 330, pp. 208-211.
Wang, et al., 2010, "Paper Spray for Direct Analysis of Complex Mixtures Using Mass Spectrometry," Angewandte Chemie, 49, pp. 877-880.
Zhang, et al., 2012, "Electrochemistry-Assisted Top-Down Characterization of Disulfide-Containing Proteins," Anal Chem., 84, pp. 1-7.
Zhang, et al., 2012, "Mass Spectrometric Analysis of Thiol Proteins/ Peptides Following Selenamide Derivatization and Electrolytic Reduction of Disulfide Bonds," 240 pages.
Zhang, et al., 2014, "Paper Spray Ionization of Noncovalent Protein Complexes," Anal. Chem., 5 pages.
Abe, et al., 2008, "Inkjet-Printed Microfluidic Multianalyte Chemical Sensing Paper," Anal. Chem. 80, pp. 6928-6934.
Atlas, et al., 2011, "Oil biodegradation and bioremediation: a tale of the two worst spilss in U.S. history" Environmental Science & Technology, 45, pp. 6709-6715.
Bruzewicz, et al., 2008, "Low-Cost Printing of Poly(dimethylsiloxane) Barriers to Define Microschannels in Paper," Anal. Chem., 80, pp. 3387-3392.
Claydon, et al. 1996, "The Rapid Identification of Intact Microorganisms Using Mass Spectrometry", Nature Biotechnology, vol. 14, No. 11, pp. 1584-1586.
Cody, et al, 2005, "Versatile New Ion Source for the Analysis of Materials in Open Air under Ambient Condition," Anal Chem, vol. 77, pp. 2297-2302.
Cooks, et al, 2006, "Ambient Mass Spectrometry," Science 311, pp. 1566-1570.
Cooks, et al., 2001, "New ionization methods and miniature mass spectrometers for biomedicine: DESI imaging for cancer diagnostics and paper spray ionization for therapeutic drug monitoring," Faraday Discussions 149, pp. 247-267.
Douglas, et al, 2012,"Paper Spray Ionization for the analysis of Naphthenic Acids," Irving k. Barber School of the Arts and Sciences, 7th Annual Undergraduate Research Conference, pp. 5-6.
Eckert, et al., 2012, "Chemical Characterization of Crude Petroleum Using Nanospray Desorption Eelectrospray Ionization Coupled With High-Resolution Mass Spectrometry", Analytical Chemistry, 84, pp. 1517-1525.
Examination Report issued in Indian Application No. 7914/CHENP/ 2011, dated Jan. 2, 2018, 4 pages.
Extended European Search Report issued in European Application No. 14818223.1, dated Oct. 18, 2016, 5 pages.
Extended European Search Report issued in European Application No. 14 875 647.1, dated Jun. 22, 2014, 13 pages.
Extended European Search Report issued in European Application No. 14745610.7, dated Sep. 7, 2016, 11 pages.
Extended European Search Report issued in European Application No. 19204134.1, dated Feb. 20, 2020, 12 pages.
Ferguson, et al., 2011, "Direct Ionization of Large Proteins and Protein Complexes by Desorption Electrospray Ionization-Mass Spectrometry," Anal. Chem., 83, pp. 6468-6473.
First Examiner's Report issued in Canadian Application No. 2,759,987, dated Mar. 21, 2016, 9 pages.

(56) References Cited

OTHER PUBLICATIONS

Gao, et al, 2006, "Handheld Rectilinear Ion Trap Mass Spectrometer," Anal. Chem., vol. 78: pp. 5994-6002.
Gao, et al., 2008, "Design and Characterization of a Multisource Hand-Held Tandem Mass Spectrometer", Z. Anal. Chem., 80, pp. 7198-7205.
Gaskell, 1997, "Electrospray: Principles and Practice," J. Mass. Spect., 32, pp. 677-688.
Ghosh, 2001, "Separation of proteins using hydrophobic interaction membrane chromatography," Journal of Chromatography, vol. 923, No. 1-2, 6 pages.
Ghosh, 2002, "Purification of lysozyme by microporous PVDF membrane-based chromatographic process," Biochemical Engineering Journal, vol. 14, No. 2, 8 pages.
Gough, et al. 1999, "Analysis of Oilfield Chemicals by Electrospray Mass Spectrometry", Rapid Communications in Mass Spectrometry, pp. 227-236.
Gough, et al., 1998, "Molecular Monitoring of Residual Corrosion Inhibitor Actives in Oilfields Fluids: Implications for Inhibitor Performance" Corrosion, 98 Paper No. 33, 12 Pages.
Harris, et al., 2011, "Ambient Sampling/Ionization Mass Spectrometry: Applications and Current Trends," Anal. Chem., 83, pp. 4508-4538.
Hou, et al., 2011, "Sampling Wand for an Ion Trap Mass Spectrometer," Anal. Chem, 83, pp. 1857-1861.
Huang, et al., 2010, "Ambient Ionization Mass Spectrometry," Ann. Rev. Anal. Chem., 3:, pp. 43-65.
Ifa, et al., 2010, "Desorption electrospray ionization and other ambient ionization methods: current progress and preview," Analyst 135, pp. 669-681, published in United Kingdom.
International Preliminary Report of Patentability issued in International Application No. PCT/US2010/032881, dated Nov. 10, 2011, 7 pages.
International Preliminary Report on Patentability issued in International Application No. PCT/US2009/045649, dated Dec. 9, 2010, 6 pages.
International Search Report and Written Opinion issued in International Application No. PCT/US2010/032881, dated Aug. 4, 2010, 9 pages.
International Search Report and Written Opinion issued in International Application No. PCT/US14/34767, dated Aug. 27, 2014, 20 pages.
International Search Report and Written Opinion issued in International Application No. PCT/US2010/032881, dated Aug. 4, 2010, 10 pages.
International Search Report and Written Opinion issued in International Application No. PCT/US2014/012746, dated Jul. 8, 2014, 15 pages.
International Search Report issued in International Application No. PCT/US2014/011000, dated Apr. 19, 2014, 2 pages.
Jjunju, et al., 2013, "In Situ Analysis of Corrosion Inhibitors Using a Portable Mass Spectrometer with Paper Spray Ionization", Analyst, 138,3740, first published on-line May 9, 2013, (10 Pages).
Joyce, 1991, "Special Report: Glassware, Plasticware Compete in Labs," May 27, 1991, The Scientist Magazine, 3 pages.
Kujawinski, et al., 2011, "Fate of Dispersants Associated with the Deepwater Horizon Oil Spill" Science and Technology, 45, pp. 1298-1306.
Li, et al, 2008, "Paper-Based Microfluidic Devices by Plasma Treatment," Anal. Chem, 80, pp. 9131-9134.
Liu, et al, 2012, "Signal and charge enhancement for protein analysis by liquid chromatography-mass spectrometry with desorption electrospray ionization," International Journal of Mass Spectrometry 325-327, pp. 161-166.
Liu, et al, 2013, "Recent advances of electrochemical mass spectrometry," Analyst, 138, pp. 5519-5539.
Liu, et al., 2010, "Development, Characterization and Application of Paper Spray Ionization", Anal. Chem. 82, 2463-2471.
Lozano, et al., 2005, "Ionic Liquid Ion Sources: Characterization of Externally Wetted Emitters", Journal of Colloid and Interface Science, 282, pp. 415-421.
Lui, et al, 2013, "Measuring Protein-Ligand Interactions Using Liquid Sample Desorption Electrospray Ionization Mass Spectrometry," Anal. Chem. 85, pp. 11966-11972.
Luo, et al., 2011, "Field ionization using densely spaced arrays of nickel-tipped carbon nanotubes". Chemical Physics Letters, Elsevier, vol. 505, No. 4,, pp. 126-129.
Mandal, et al. 2012, "Solid probe assisted nanoelectrospray ionization mass spectrometry for biological tissue Diagnostics," Analyst, 137, pp. 4658-4661.
Martinez, et al, 2007, "Patterned Paper as a Platform for Inexpensive, Low-Volume, Portable Bioassays," Angew. Chem. Int. Ed., 46:1318-1320.
Martinez, et al., 2008, "FLASH: A rapid method for prototyping paper-based microfluidic devices," Lab Chip, 8, pp. 2146-2150.
Martinez, et al., 2008, "Three-dimensional microfluidic devices fabricated in layered paper and tape," PNAS, 105, pp. 19606-19611.
Miao et.al., 2009, "Direct Analysis of Liquid Samples by Desorption Electrospray Ionization-Mass Spectrometry (DESI-MS)," J Am Soc Mass Spectrom, 20, pp. 10-19.
Narayanan, et al, 2014, "Molecular Ionization from Carbon Nanotube Paper", Angewandte Chemie International Edition, vol. 53, No. 23, pp. 5936-5940.

\* cited by examiner

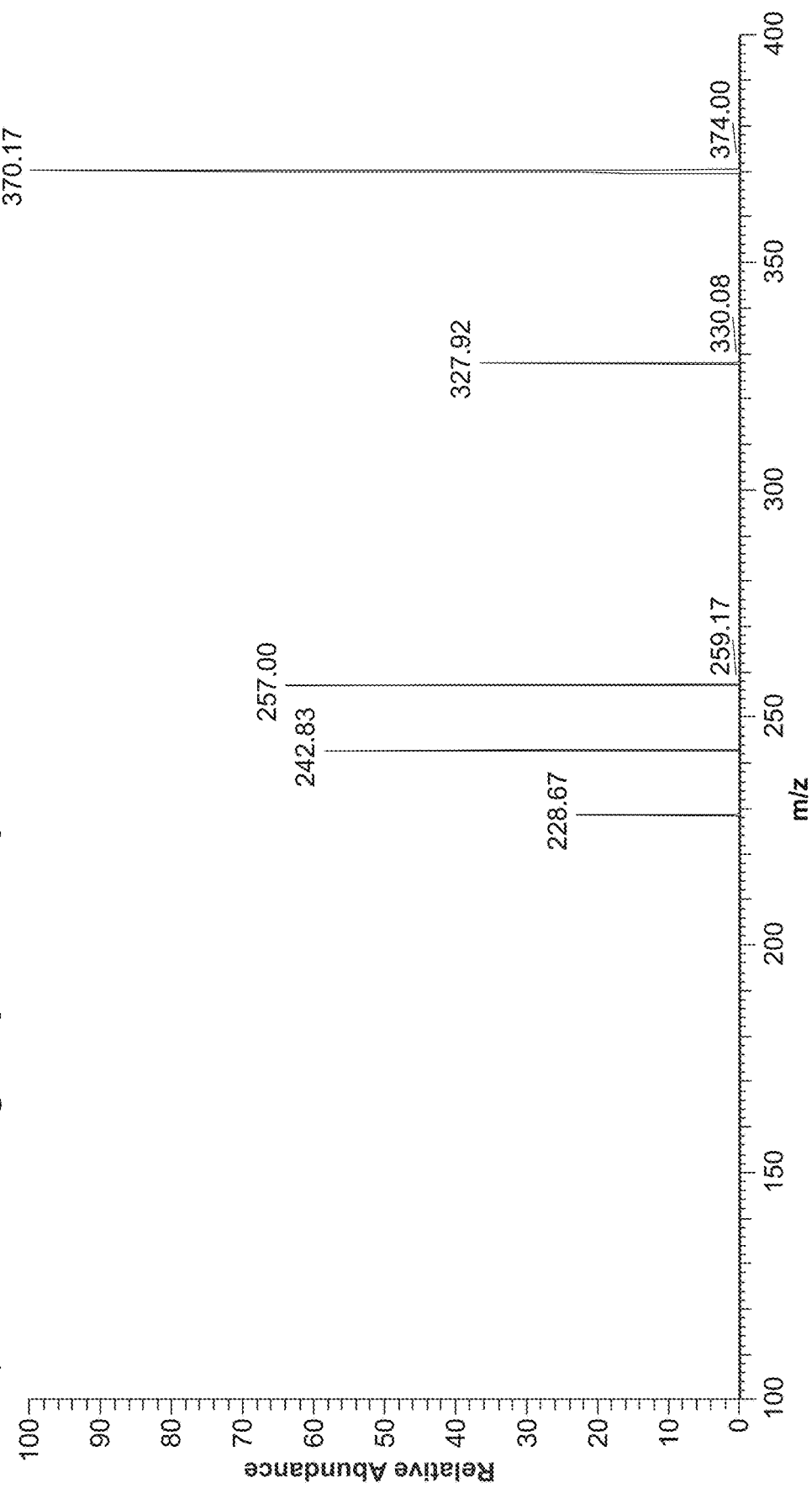

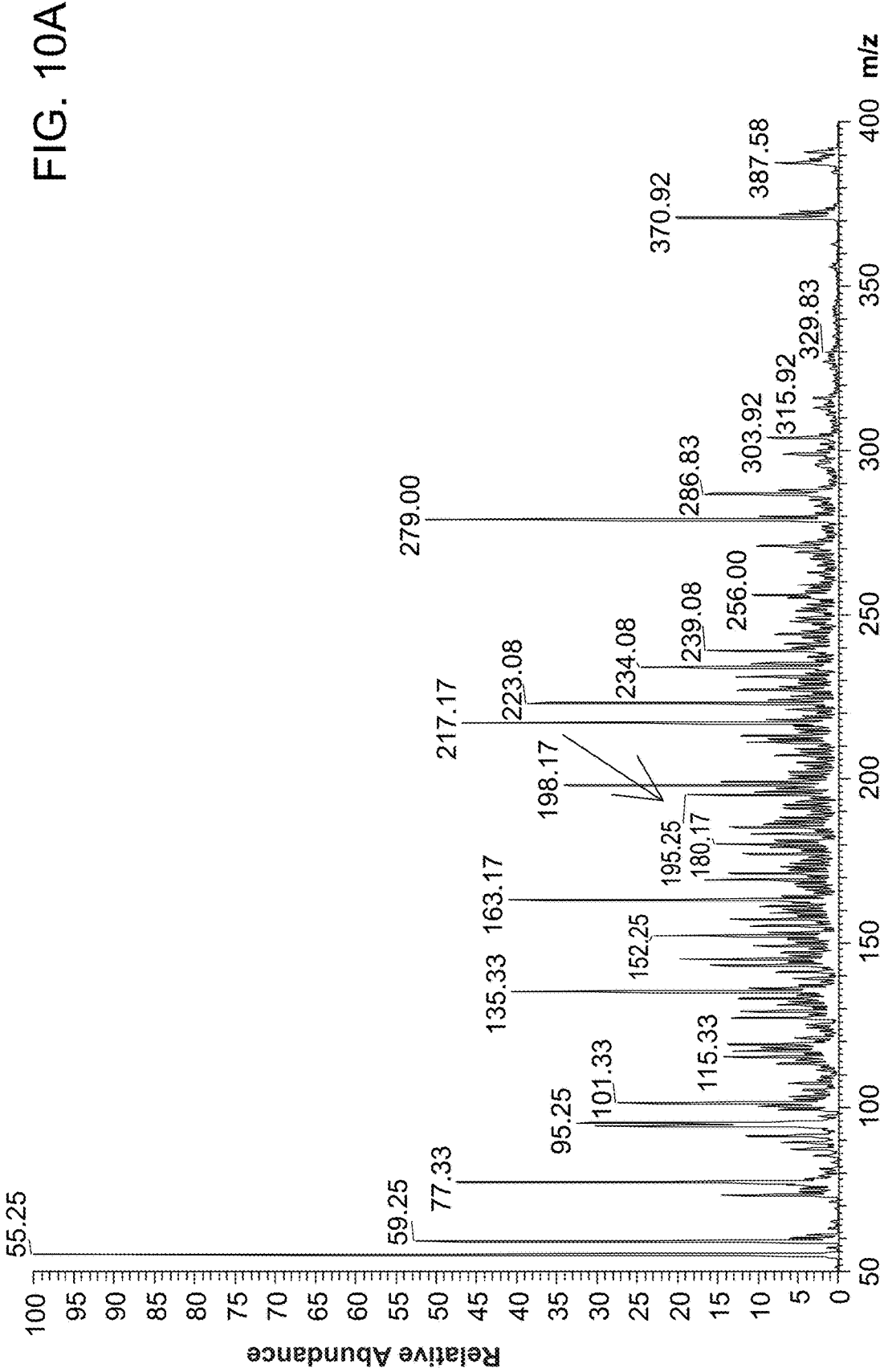

FIG. 29C  Lipids on tumor section
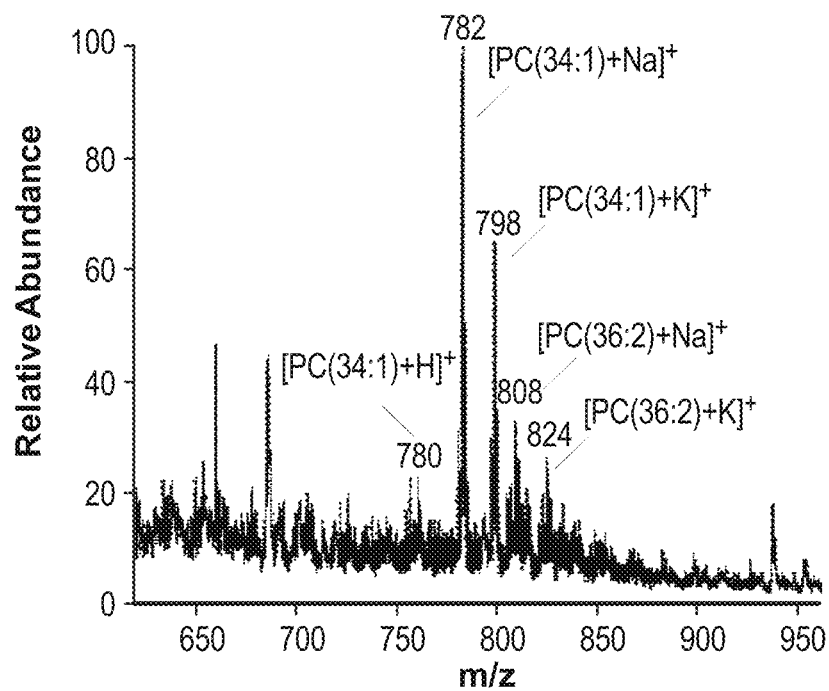
FIG. 29D  Lipids on non-tumor section
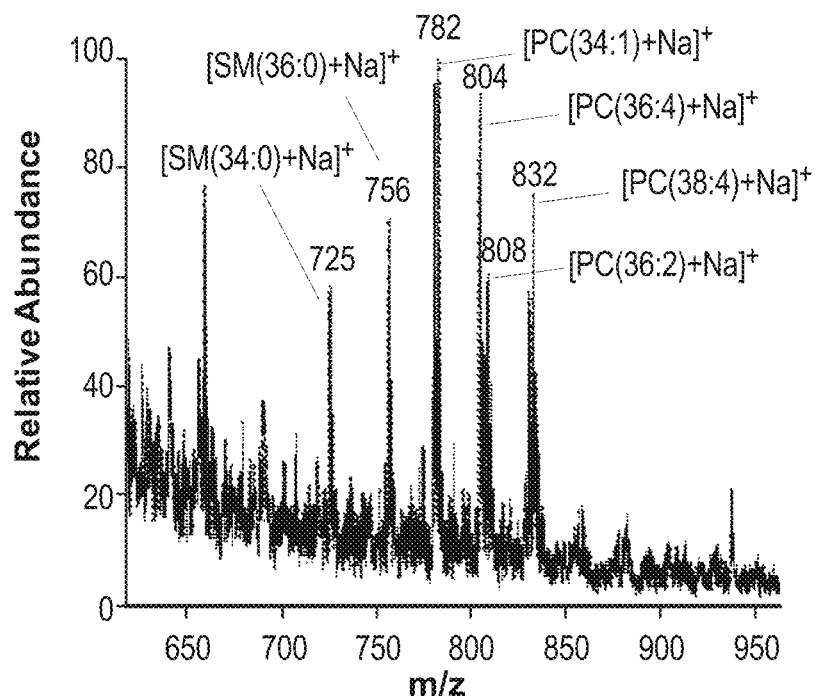

Analysis of dried serum spot on plain paper

Analysis of dried serum spot on paper preloaded with betaine aldehyde chloride

FIG. 34A
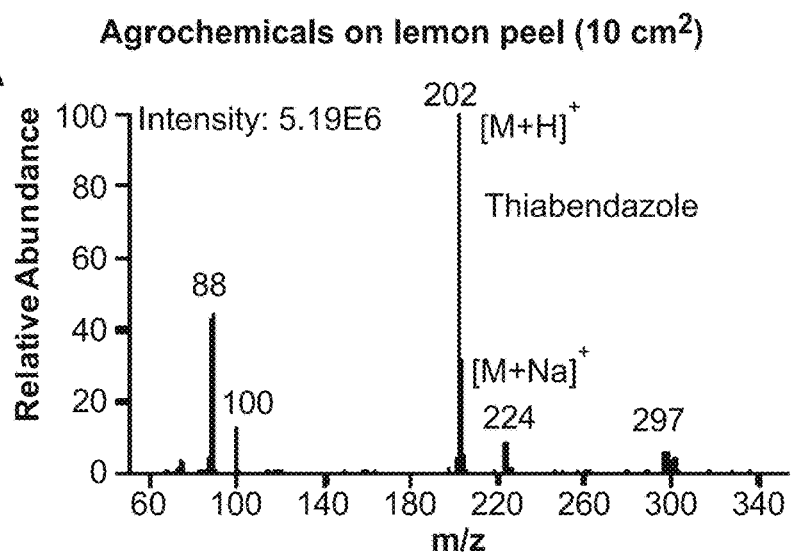
FIG. 34B
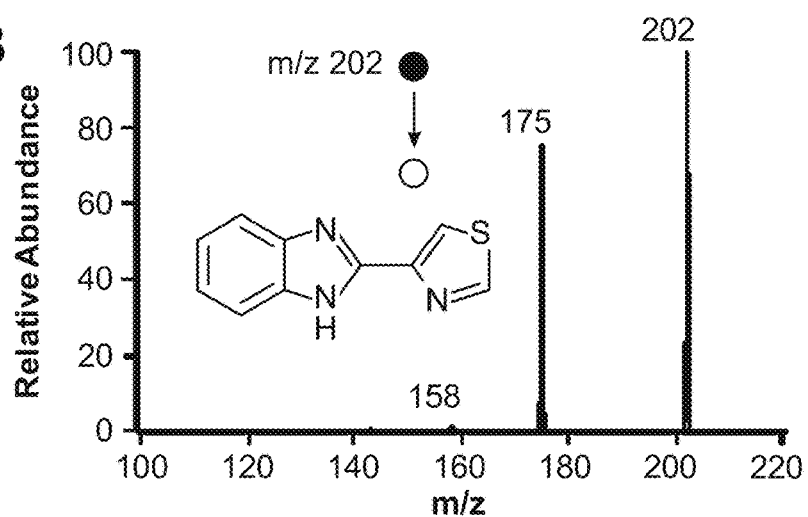
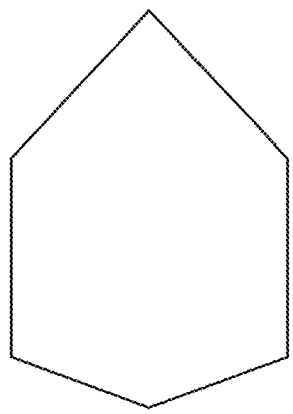
FIG 35

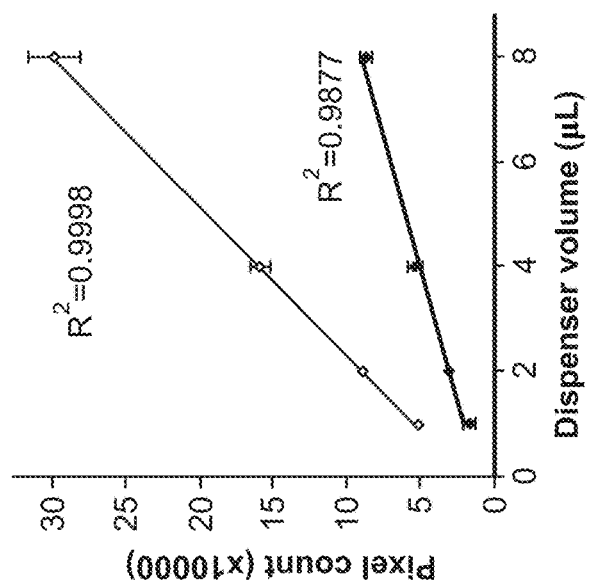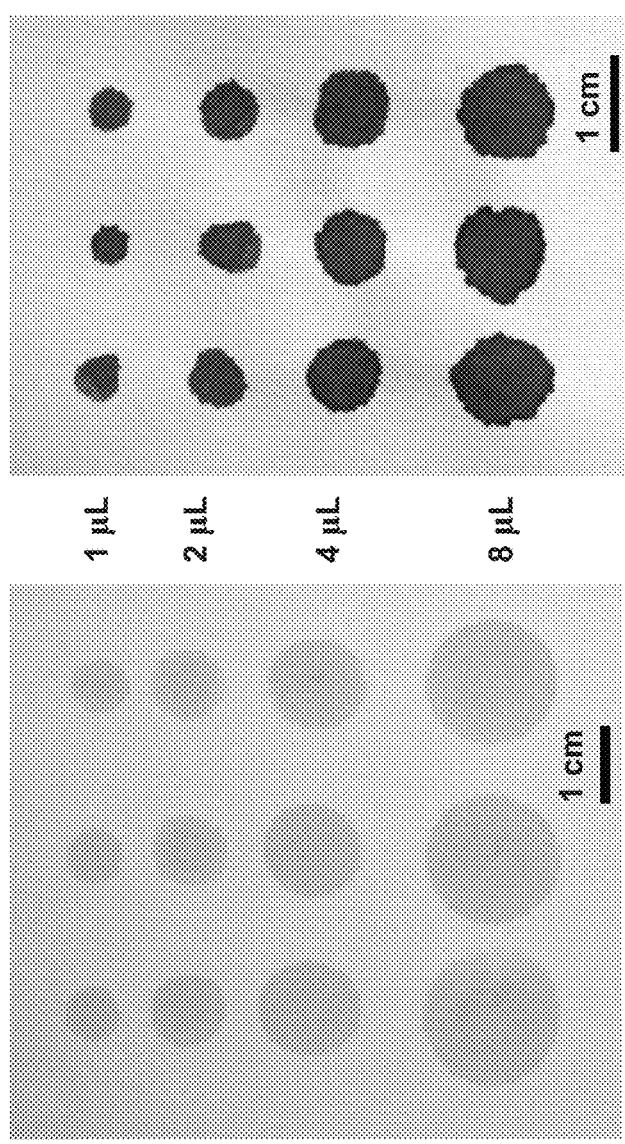
FIG. 42A
FIG. 42B
FIG. 42C

SAMPLE DISPENSER INCLUDING AN INTERNAL STANDARD AND METHODS OF USE THEREOF

RELATED APPLICATIONS

The present application is a continuation of U.S. nonprovisional application Ser. No. 15/357,048, filed Nov. 21, 2016, which is a continuation of U.S. nonprovisional application Ser. No. 13/784,094, filed Mar. 4, 2013, which is a continuation-in-part of U.S. nonprovisional application Ser. No. 13/265,110, filed Jan. 31, 2012, which is a 35 U.S.C. § 371 national phase application of PCT/US2010/032881, filed Apr. 29, 2010, which claims the benefit of and priority to each of U.S. provisional patent application Ser. No. 61/174,215, filed Apr. 30, 2009, U.S. provisional patent application Ser. No. 61/246,707 filed Sep. 29, 2009, and U.S. provisional patent application Ser. No. 61/308,332, filed Feb. 26, 2010. The present application also claims the benefit of and priority to U.S. provisional application Ser. No. 61/608,944, filed Mar. 9, 2012. The content of each of application is incorporated by reference herein in its entirety.

GOVERNMENT SUPPORT

This invention was made with government support under RR031246 and GM103454 awarded by National Institutes of Health. The government has certain rights in the invention.

FIELD OF THE INVENTION

The invention generally relates to a sample dispenser including an internal standard and methods of use thereof.

BACKGROUND

Quantitative analysis of complex mixtures using mass spectrometry is one of the most important territories in analytical chemistry. Each phase of the quantitative analysis procedure should be carefully optimized and precisely calibrated. Representative methods for quantitative analysis includes high-performance liquid chromatography-mass spectrometry (HPLC-MS) and gas chromatography-mass spectrometry (GC-MS). Both have been developed for decades and are already widely used for drug metabolism, biomarker discovery, protein/lipid study, environmental monitoring, food safety and forensic applications. A general procedure using a modern MS analysis system typically starts from sample preparation. Sample preparation typically involves analytes being concentrated, purified and extracted into pure solution, then chromatographically separated and analyzed using mass spectrometry in a successive manner. Either external standards or internal standards should be used for calibration. LC/GC-MS is a powerful method for quantitative analysis for complex mixtures, but is still labor intensive and time consuming, the operators also must be highly trained to use the instrument and to design and troubleshoot methods.

Elimination of sample preparation benefits MS analysis in quantitation, which has become a reality by using ambient ionization methods. Ambient analysis involves the interrogation of samples in their native environment to reduce the time required for analysis and to simplify the operations. One drawback is that analysis of untreated complex samples can lead to ion suppression, in which the detection of the analyte of interest is compromised due to the presence of other interfering chemicals. The sensitivity and reproducibility of the method can suffer due to these matrix effects. As in traditional quantitative MS analysis, the introduction of internal standards allows the best quantitative performance for ambient analysis. A problem with methods for introducing internal standards to samples is accurate reproducibility when dealing with small volumes. In such circumstance, using an air displacement pipette to transport sub-microliter liquid may result in a 12% error in pipetting accuracy, which is even worse for blood. Spiking internal standard into samples in a vial using pipetting and vortex mixing is not suitable either when dealing with microliter samples.

SUMMARY

The invention generally provides fluid dispensing devices and methods for quantitative analysis of trace compounds in small volumes of complex mixtures (~1 µL). Dispensing devices of the invention generally have a fluid chamber in which at least a portion of an inner wall of the chamber is coated with internal standard on its inner surface. Fluid containing the analytes that is taken into the chamber mixes with the internal standard so that dispensed fluid includes the internal standard. The internal standard automatically mixes into the sample during this process and the volumes of the internal standard solution and sample are both regulated by the volume of the chamber. The precision in quantitation is not sensitive to the variations in volume of the chamber. Devices of the invention significantly improved quantitation accuracy for analysis of 1 µL samples using various analysis techniques, such as ambient ionization methods.

In certain aspects, the invention provides a fluid dispenser that includes a fluid chamber. A portion of an inner wall of the chamber includes an internal standard. The chamber is configured such that fluid introduced to the chamber must interact with the portion of the chamber wall that includes the internal standard prior to flowing through an outlet of the chamber. The dispenser also includes a member coupled to the chamber such that it can control movement of fluid within the chamber. Generally, the chamber outlet is also an inlet for the fluid, but devices of the invention are not limited to such a configuration.

The fluid chamber may be any chamber capable of holding a liquid. In certain embodiments, the chamber is an elongate tube, such as a capillary tube. Typically, the internal standard coats a portion of an inner wall of the tube. In certain embodiments, the internal standard coats an entirety of the inner walls of the tube.

The member is typically a device that controls movement through application of pneumatic pressure. Any exemplary member is a compressible hollow bulb, such as the bulb of a pipette.

Another aspect of the invention provides a method for dispensing fluid. The method generally involves providing a fluid dispenser including a fluid chamber, in which a portion of an inner wall of the chamber includes an internal standard, the chamber being configured such that fluid introduced to the chamber must interact with the portion of the chamber wall that includes the internal standard prior to flowing through an outlet of the chamber; and a member coupled to the chamber such that it can control movement of fluid within the chamber. A fluid sample is loaded into the dispenser. Once loaded, the sample is given time (e.g., a few seconds to a few minutes, to a few days) sufficient for the sample to interact with the internal standard such that internal standard is introduced into the sample. The sample now containing internal standard is dispensed through the outlet. The member may facilitate loading the sample into the dispenser, or dispensing the sample through the outlet. Although, in some embodiments, capillary action alone is enough to load the sample into the dispenser and to accomplish a majority of the dispensing. Accordingly, the member does not need to be solely responsible for the loading and the dispensing.

Dispensers of the invention may be used with any liquid to which an internal standard needs to be introduced. In certain embodiments, the internal standard is a body fluid, such as blood, urine, or serum.

BRIEF DESCRIPTION OF THE FIGURES

FIG. 1 panel (B) is a drawing of a sample solution pre-spotted onto the paper and a droplet of solvent being subsequently supplied to the paper for electrospray ionization.

FIG. 2 panel (B) is a MS/MS spectrum of heroin (concentration: 1 ppb, volume: 10 μl, solvent: MeOH/H$_2$O/HOAc (50:49:1, v/v/v)).

FIG. 3 panel (B) is a MS/MS spectrum of caffeine (concentration: 10 ppb, volume: 10 μl, solvent: MeOH/H$_2$O/HOAc (50:49:1, v/v/v)).

FIG. 4 panel (B) is a MS/MS spectrum of benzoylecgonine (concentration: 10 ppb, volume: 10 μl, solvent: MeOH/H$_2$O/HOAc (50:49:1, v/v/v)).

FIG. 5 panel (B) is a MS/MS spectrum of serine (concentration: 100 ppb, volume: 10 μl, solvent: MeOH/H$_2$O/HOAc (50:49:1, v/v/v)).

FIG. 6 panel (B) is a MS/MS spectrum of bradykinin 2-9 (concentration: 1 ppm, volume: 10 μl, solvent: MeOH/H$_2$O/HOAc (50:49:1, v/v/v)).

FIG. 7 panel (B) shows the MS/MS spectrum of the blood spot without heroin.

FIG. 8 panel (B) shows the MS/MS spectrum of the urine spot without heroin.

FIG. 9 panel (B) is a MS spectrum showing caffeine detected from coffee powder. A paper slice was used to collect the coffee powder from a coffee bag by swabbing the surface.

FIG. 10 panel (A) is a MS spectrum showing that caffeine was detected in urine from a person who consumed coffee. FIG. 10 panel (B) is a MS spectrum showing that caffeine was not detected in urine from a person who had not consumed any coffee.

FIG. 13 panel (A) direct analysis of onion without sample preparation. FIG. 13 panel (B) using standard solution.

FIG. 34 panels (A and B) show mass spectra of agrochemicals that are present on a lemon peel purchased from a grocery store and swabbed with paper.

FIG. 35 shows a design of a substrate for paper spray with multiple corners. The angle of the corner to be used for spray is smaller than that of other corners.

FIG. 37, panel B is a schematic showing a glass capillary placed in the lower opening of a 1000 µL pipette tip. FIG. 37 panel C is a schematic showing using sampling capillary to transfer finger-stick blood and to deposit it onto paper substrate to make a dried blood spot.

FIG. 38, panel B is a photograph showing blood samples collected in the sampling capillaries. The length of each capillary is noted.

FIG. 39 panel B shows the ratio of MS/MS ion current for imatinib (m/z 494→m/z 394, 200 ng/mL) to that for imatinib-D8 (m/z 502→m/z 394, 100 ng/mL) measured from DBS prepared with sampling capillaries (top) and pipetting pre-mixed samples (bottom).

FIG. 40 panel B shows analysis of imatinib in blood with sampling capillaries and paper spray ionization. Bovine blood (1 µL) was applied directly to chromatography paper with the capillary dispenser coated with 0.1 ng imatinib-d8 as internal standard. DC voltage (4.2 kV) was applied to the paper wetted with 35 µL spray solvent (acetonitrile/water, 90:10, v:v). Inset shows the low-concentration range. Error bars represent the standard deviation for at least three replicates.

FIG. 41 panel B shows analysis of cocaine in urine (33-1000 ng/mL) using DESI, dried sample spot prepared on a glass slide.

FIG. 42, panel A is a photograph showing that liquid samples with low viscosity (methanol solution, urine, serum) could be dispensed on paper using capillary action only. Array of samples prepared with blue dye in methanol solution were prepared with the dispensers. FIG. 42, panel B is a photograph showing that blood was transferred on chromatography paper to form array of dried blood spots of different sizes. FIG. 42, panel C is a graph showing area of sample spot (Pixel count obtained from (FIG. 42, panel B)) vs. capillary volume.

DETAILED DESCRIPTION

Figure 1A:
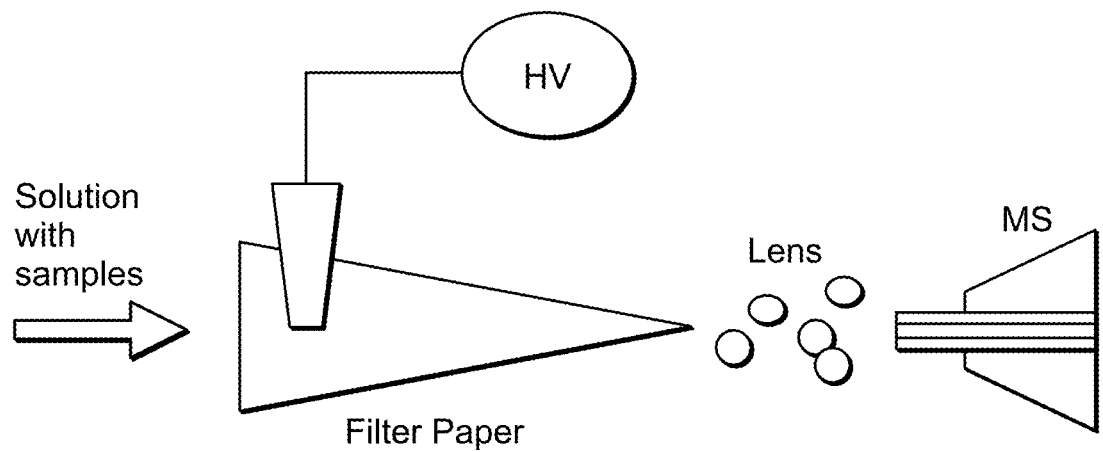
FIG. 1 panel (A) is a drawing of a sample solution being fed to a piece of paper for electrospray ionization.
Figure 1B:
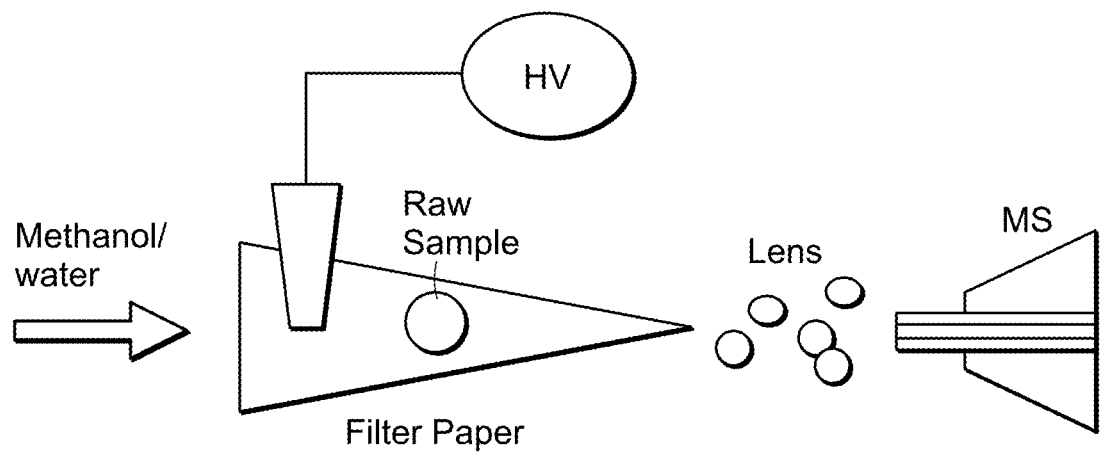

A new method of generating ions from fluids and solids for mass spectrometry analysis is described. Porous materials, such as paper (e.g. filter paper or chromatographic paper) or other similar materials are used to hold and transfer liquids and solids, and ions are generated directly from the edges of the material when a high electric voltage is applied to the material (FIG. 1). The porous material is kept discrete (i.e., separate or disconnected) from a flow of solvent, such as a continuous flow of solvent. Instead, sample is either spotted onto the porous material or swabbed onto it from a surface including the sample. The spotted or swabbed sample is then connected to a high voltage source to produce ions of the sample which are subsequently mass analyzed. The sample is transported through the porous material without the need of a separate solvent flow. Pneumatic assistance is not required to transport the analyte; rather, a voltage is simply applied to the porous material that is held in front of a mass spectrometer.

In certain embodiments, the porous material is any cellulose-based material. In other embodiments, the porous material is a non-metallic porous material, such as cotton, linen wool, synthetic textiles, or plant tissue. In still other embodiments, the porous material is paper. Advantages of paper include: cost (paper is inexpensive); it is fully commercialized and its physical and chemical properties can be adjusted; it can filter particulates (cells and dusts) from liquid samples; it is easily shaped (e.g., easy to cut, tear, or fold); liquids flow in it under capillary action (e.g., without external pumping and/or a power supply); and it is disposable.

In certain embodiments, the porous material is integrated with a solid tip having a macroscopic angle that is optimized for spray. In these embodiments, the porous material is used for filtration, pre-concentration, and wicking of the solvent containing the analytes for spray at the solid type.

In particular embodiments, the porous material is filter paper. Exemplary filter papers include cellulose filter paper, ashless filter paper, nitrocellulose paper, glass microfiber filter paper, and polyethylene paper. Filter paper having any pore size may be used. Exemplary pore sizes include Grade 1 (11 µm), Grade 2 (8 µm), Grade 595 (4-7 µm), and Grade 6 (3 µm), Pore size will not only influence the transport of liquid inside the spray materials, but could also affect the formation of the Taylor cone at the tip. The optimum pore size will generate a stable Taylor cone and reduce liquid evaporation. The pore size of the filter paper is also an important parameter in filtration, i.e., the paper acts as an online pretreatment device. Commercially available ultra filtration membranes of regenerated cellulose, with pore sizes in the low nm range, are designed to retain particles as small as 1000 Da. Ultra filtration membranes can be commercially obtained with molecular weight cutoffs ranging from 1000 Da to 100,000 Da.

Probes of the invention work well for the generation of micron scale droplets simply based on using the high electric field generated at an edge of the porous material. In particular embodiments, the porous material is shaped to have a macroscopically sharp point, such as a point of a triangle, for ion generation. Probes of the invention may have different tip widths. In certain embodiments, the probe tip width is at least about 5 µm or wider, at least about 10 µm or wider, at least about 50 µm or wider, at least about 150 µm or wider, at least about 250 µm or wider, at least about 350 µm or wider, at least about 400µ or wider, at least about 450 µm or wider, etc. In particular embodiments, the tip width is at least 350 µm or wider. In other embodiments, the probe tip width is about 400 µm. In other embodiments, probes of the invention have a three dimensional shape, such as a conical shape.

As mentioned above, no pneumatic assistance is required to transport the droplets. Ambient ionization of analytes is realized on the basis of these charged droplets, offering a simple and convenient approach for mass analysis of solution-phase samples.

Sample solution is directly applied on the porous material held in front of an inlet of a mass spectrometer without any pretreatment. Then the ambient ionization is performed by applying a high potential on the wetted porous material. In certain embodiments, the porous material is paper, which is a type of porous material that contains numerical pores and microchannels for liquid transport. The pores and microchannels also allow the paper to act as a filter device, which is beneficial for analyzing physically dirty or contaminated samples.

In other embodiments, the porous material is treated to produce microchannels in the porous material or to enhance the properties of the material for use as a probe of the invention. For example, paper may undergo a patterned silanization process to produce microchannels or structures on the paper. Such processes involve, for example, exposing the surface of the paper to tridecafluoro-1,1,2,2-tetrahydrooctyl-1-trichlorosilane to result in silanization of the paper. In other embodiments, a soft lithography process is used to produce microchannels in the porous material or to enhance the properties of the material for use as a probe of the invention. In other embodiments, hydrophobic trapping regions are created in the paper to pre-concentrate less hydrophilic compounds.

Hydrophobic regions may be patterned onto paper by using photolithography, printing methods or plasma treatment to define hydrophilic channels with lateral features of 200-1000 µm. See Martinez et al. (*Angew. Chem. Int. Ed.* 2007, 46, 1318-1320); Martinez et al. (*Proc. Natl Acad. Sci. USA* 2008, 105, 19606-19611); Abe et al. (*Anal. Chem.* 2008, 80, 6928-6934); Bruzewicz et al. (*Anal. Chem.* 2008, 80, 3387-3392); Martinez et al. (*Lab Chip* 2008, 8, 2146-2150); and Li et al. (*Anal. Chem.* 2008, 80, 9131-9134), the content of each of which is incorporated by reference herein in its entirety. Liquid samples loaded onto such a paper-based device can travel along the hydrophilic channels driven by capillary action.

Another application of the modified surface is to separate or concentrate compounds according to their different affinities with the surface and with the solution. Some compounds are preferably absorbed on the surface while other chemicals in the matrix prefer to stay within the aqueous phase. Through washing, sample matrix can be removed while compounds of interest remain on the surface. The compounds of interest can be removed from the surface at a later point in time by other high-affinity solvents. Repeating the process helps desalt and also concentrate the original sample.

Methods and systems of the invention use a porous material, e.g., paper, to hold and transport analytes for mass spectral analysis. Analytes in samples are pre-concentrated, enriched and purified in the porous material in an integrated fashion for generation of ions with application of a high voltage to the porous material. In certain embodiments, a discrete amount of transport solution (e.g., a droplet or a few droplets) is applied to assist movement of the analytes through the porous material. In certain embodiments, the analyte is already in a solution that is applied to the porous material. In such embodiments, no additional solvent need be added to the porous material. In other embodiments, the analyte is in a powdered sample that can be easily collected by swabbing a surface. Systems and methods of the invention allow for analysis of plant or animal tissues, or tissues in living organisms.

Methods and systems of the invention can be used for analysis of a wide variety of small molecules, including epinephrine, serine, atrazine, methadone, roxithromycin, cocaine and angiotensin I. All display high quality mass and MS/MS product ion spectra (see Examples below) from a variety of porous surfaces. Methods and systems of the invention allow for use of small volumes of solution, typically a few μL, with analyte concentrations on the order of 0.1 to 10 μg/mL (total amount analyte 50 pg to 5 ng) and give signals that last from one to several minutes.

Methods and systems of the invention can be used also for analysis of a wide variety of biomolecules, including proteins and peptides. Methods of the invention can also be used to analyze oligonucleotides from gels. After electrophoretic separation of oligonucleotides in the gel, the band or bands of interest are blotted with porous material using methods known in the art. The blotting results in transfer of at least some of the oligonucleotides in the band in the gel to the porous material. The porous material is then connected to a high voltage source and the oligonucleotides are ionized and sprayed into a mass spectrometer for mass spectral analysis.

Methods and systems of the invention can be used for analysis of complex mixtures, such as whole blood or urine. The typical procedure for the analysis of pharmaceuticals or other compounds in blood is a multistep process designed to remove as many interferences as possible prior to analysis. First, the blood cells are separated from the liquid portion of blood via centrifugation at approximately 1000×g for 15 minutes (Mustard, J. F.; Kinlough-Rathbone, R. L.; Packham, M. A. *Methods in Enzymology*; Academic Press, 1989). Next, the internal standard is spiked into the resulting plasma and a liquid-liquid or solid-phase extraction is performed with the purpose of removing as many matrix chemicals as possible while recovering nearly all of the analyte (Buhrman, D. L.; Price, P. I.; Rudewicz, P. J. *Journal of the American Society for Mass Spectrometry* 1996, 7, 1099-1105). The extracted phase is typically dried by evaporating the solvent and then resuspended in the a solvent used as the high performance liquid chromatography (HPLC) mobile phase (Matuszewski, B. K.; Constanzer, M. L.; Chavez-Eng, C. M., Ithaca, N.Y., Jul. 23-25 1997; 882-889). Finally, the sample is separated in the course of an HPLC run for approximately 5-10 minutes, and the eluent is analyzed by electrospray ionization-tandem mass spectrometry (Hopfgartner, G.; Bourgogne, E. *Mass Spectrometry Reviews* 2003, 22, 195-214).

Methods and systems of the invention avoid the above sample work-up steps. Methods and systems of the invention analyze a dried blood spots in a similar fashion, with a slight modification to the extraction procedure. First, a specialized device is used to punch out identically sized discs from each dried blood spot. The material on these discs is then extracted in an organic solvent containing the internal standard (Chace, D. H.; Kalas, T. A.; Naylor, E. W. *Clinical Chemistry* 2003, 49, 1797-1817). The extracted sample is dried on the paper substrate, and the analysis proceeds as described herein.

Examples below show that methods and systems of the invention can directly detect individual components of complex mixtures, such as caffeine in urine, 50 pg of cocaine on a human finger, 100 pg of heroin on a desktop surface, and hormones and phospholipids in intact adrenal tissue, without the need for sample preparation prior to analysis (See Examples below). Methods and systems of the invention allow for simple imaging experiments to be performed by examining, in rapid succession, needle biopsy tissue sections transferred directly to paper.

Analytes from a solution are applied to the porous material for examination and the solvent component of the solution can serve as the electrospray solvent. In certain embodiments, analytes (e.g., solid or solution) are pre-spotted onto the porous material, e.g., paper, and a solvent is applied to the material to dissolve and transport the analyte into a spray for mass spectral analysis.

In certain embodiments, a solvent is applied to the porous material to assist in separation/extraction and ionization. Any solvents may be used that are compatible with mass spectrometry analysis. In particular embodiments, favorable solvents will be those that are also used for electrospray ionization. Exemplary solvents include combinations of water, methanol, acetonitrile, and THF. The organic content (proportion of methanol, acetonitrile, etc. to water), the pH, and volatile salt (e.g. ammonium acetate) may be varied depending on the sample to be analyzed. For example, basic molecules like the drug imatinib are extracted and ionized more efficiently at a lower pH. Molecules without an ionizable group but with a number of carbonyl groups, like sirolimus, ionize better with an ammonium salt in the solvent due to adduct formation.

In certain embodiments, a multi-dimensional approach is undertaken. For example, the sample is separated along one dimension, followed by ionization in another dimension. In these embodiments, separation and ionization can be individually optimized, and different solvents can be used for each phase.

In other embodiments, transporting the analytes on the paper is accomplished by a solvent in combination with an electric field. When a high electric potential is applied, the direction of the movement of the analytes on paper is found to be related to the polarity of their charged forms in solution. Pre-concentration of the analyte before the spray can also be achieved on paper by placing an electrode at a point on the wetted paper. By placing a ground electrode near the paper tip, a strong electric field is produced through the wetted porous material when a DC voltage is applied, and charged analytes are driven forward under this electric field. Particular analytes may also be concentrated at certain parts of the paper before the spray is initiated.

In certain embodiments, chemicals are applied to the porous material to modify the chemical properties of the porous material. For example, chemicals can be applied that allow differential retention of sample components with different chemical properties. Additionally, chemicals can be applied that minimize salt and matrix effects. In other embodiments, acidic or basic compounds are added to the porous material to adjust the pH of the sample upon spotting. Adjusting the pH may be particularly useful for improved analysis of biological fluids, such as blood. Additionally, chemicals can be applied that allow for on-line chemical derivatization of selected analytes, for example to convert a non-polar compound to a salt for efficient electrospray ionization.

In certain embodiments, the chemical applied to modify the porous material is an internal standard. The internal standard can be incorporated into the material and released at known rates during solvent flow in order to provide an internal standard for quantitative analysis. In other embodiments, the porous material is modified with a chemical that allows for pre-separation and pre-concentration of analytes of interest prior to mass spectrum analysis.

The spray droplets can be visualized under strong illumination in the positive ion mode and are comparable in size to the droplets emitted from a nano-electrospray ion sources (nESI). In the negative ion mode, electrons are emitted and can be captured using vapor phase electron capture agents like benzoquinone. Without being limited by any particular theory or mechanism of action, it is believed that the high electric field at a tip of the porous material, not the fields in the individual fluid channels, is responsible for ionization.

The methodology described here has desirable features for clinical applications, including neonatal screening, therapeutic drug monitoring and tissue biopsy analysis. The procedures are simple and rapid. The porous material serves a secondary role as a filter, e.g., retaining blood cells during analysis of whole blood. Significantly, samples can be stored on the porous material and then analyzed directly from the stored porous material at a later date without the need transfer from the porous material before analysis. Systems of the invention allow for laboratory experiments to be performed in an open laboratory environment.

In other embodiments, the sample can be transferred using the capillary dispensers to substrates made from non-porous materials, such as PTFE or glass.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

EXAMPLES

The following examples are intended to further illustrate certain embodiments of the invention, and are not to be construed to limit the scope of the invention. Examples herein show that mass spectrometry probes of the invention can ionize chemical and biological samples, allowing for subsequent mass analysis and detection. An exemplary probe was constructed as a paper triangle, which was used to generate micron scale droplets by applying a high potential on the paper. The analytes were ionized from these electrically charged droplets and transported into a conventional mass spectrometer.

Examples below show that a wide range of samples could be directly analyzed in the ambient environment by probes of the invention in both of pure state and complex mixtures. The results showed that paper-based spray has the following benefits: it operated without sheath gas, i.e., few accessories were required for in situ analysis; biological samples (dried blood, urine) could be stored on the precut filter papers for months before analysis; filter paper minimized matrix effects seen with electrospray or nano electrospray in many samples (blood cells, salt and proteins) and enhanced the MS signal of chemicals in complex samples; powdered samples were easily collected by swabbing surfaces using paper pieces and then directly analyzed; the paper could be pretreated to contain internal standards that were released at known rates during solvent flow in quantitative analysis; and the paper could be pretreated to contain matrix suppression or absorption sites or to perform ion exchange or to allow on-line chemical derivatization of selected analytes.

Detection of most analytes was achieved as low as ppb levels (when examined as solutions) or in the low ng to pg range (when solids were examined) and the detection time was less than one minute. Certain Examples below provide a protocol for analyzing a dried blood spot, which can also be used for in situ analysis of whole blood samples. The dried blood spot method is also demonstrated to be compatible with the storage and transport of blood sample for blood screening and other clinical tests.

Devices of the invention integrated the capabilities of sampling, pre-separation, pre-concentration and ionization. Methods and systems of the invention simplify the problem of sample introduction in mass analyzers.

Example 1: Construction of an MS Probe

Filter paper was cut into triangular pieces with dimensions of 10 mm long and 5 mm wide and used as a sprayer (FIG. 1). A copper clip was attached to the paper, and the paper was oriented to face an inlet of a mass spectrometer (FIG. 1). The copper clip was mounted on a 3D moving stage to accurately adjust its position. A high voltage was applied to the copper clip and controlled by a mass spectrometer to generate analyte ions for mass detection.

Samples were directly applied to the paper surface that served as a sample purification and pre-concentration device. Filter paper allowed liquid samples to move through the hydrophilic network driven by capillary action and electric effects and to transport them to the tip of the paper. Separation could take place during this transport process. Sample solution was sprayed from the tip and resulted in ionization and MS detection when a high voltage (~4.5 kV) was applied to the paper surface.

All experiments were carried out with a Finnigan LTQ mass spectrometer (Thermo Electron, San Jose, Calif.). The typical temperature of the capillary inlet was set at 150° C. while 30° C. for heroin detection. The lens voltage was set at 65 V for sample analysis and 240 V for survival yield experiment. Tandem mass spectra were collected using collision-induced dissociation (CID) to identify analytes in tested samples, especially for complex mixtures and blood samples.

Example 2: Spray Generation

Spray was produced by applying a high potential on the wetted paper triangle. One paper triangle was placed in front of the inlet of LTQ with its sharp tip facing to the inlet, separated by 3 mm or more. Typically, 10 uL sample solution was applied to wet the paper triangle. The solution can wet or saturate the paper or form a thin layer of liquid film on the surface of the paper. A high potential (3-5 kV) was applied between the paper triangle and mass inlet to generate an electric field, which induced a charge accumulation on the liquid at the tip of paper triangle. The increasing coulombic force breaks the liquid to form charged droplets and then the solvent evaporated during the flight of droplets from the paper tip to the mass analyzer. Paper spray required no sheath gas, heating or any other assistance to remove the solvent.

When liquid accumulated on the paper triangle, a Taylor cone was observed at the tip when examined with a microscope. The droplets formed were clearly visible under strong illumination. The Taylor cone and visible spray disappeared after a short time of evaporation and spray. However, the mass signal lasted for a much longer period (several minutes). This revealed that the paper triangle could work in two modes for mass analysis. In a first mode, the liquid was transported inside the paper at a rate faster than the liquid could be consumed as spray at the paper tip, resulting in a large cone being formed at the paper tip and droplets being generated. In a second mode, the liquid transport inside the paper was not able to move at a rate fast enough to keep up with the spray consumption, and droplets were not visible. However, it was observed that ionization of analytes did take place. The first mode provided ESI like mass spectra and the second mode provided spectra with some of the features APCI spectra. In the latter case, the paper triangle played a role analogous to a conductive needle to generate a high electric field to ionize the molecules in the atmosphere. It was observed that the mass signal in the first mode was stronger than the mass signal in the second mode by approximately two orders of magnitude under the conditions and for the samples tested.

Example 3: Probe Considerations

Probe Materials

A number of porous materials were tested to generate charged droplets for mass spectrometry. The materials were shaped into triangles having sharp tips and sample solution was then applied to the constructed probes. Data herein show that any hydrophilic and porous substrate could be used successfully, including cotton swab, textile, plant tissues as well as different papers. The porous network or microchannels of these materials offered enough space to hold liquid and the hydrophilic environment made it possible for liquid transport by capillary action. Hydrophobic and porous substrates could also be used successfully with properly selected hydrophobic solvents.

For further investigation, six kinds of commercialized papers were selected and qualitatively tested to evaluate their capabilities in analyte detection. Filter papers and chromatography paper were made from cellulose, while glass microfiber filter paper was made from glass microfiber. FIG. 19 shows the mass spectra of cocaine detection on those papers. The spectrum of glass fiber paper (FIG. 19 panel E) was unique because the intensity of background was two orders of magnitude lower than other papers and the cocaine peak (m/z, 304) could not be identified.

It was hypothesized that the glass fiber paper was working on mode II and prohibiting efficient droplet generation, due to the relative large thickness (~2 mm). This hypothesis was proved by using a thin layer peeled from glass fiber paper for cocaine detection. In that case, the intensity of the background increased and a cocaine peak was observed. All filter papers worked well for cocaine detection, (FIG. 19 panels A-D). Chromatography paper showed the cleanest spectrum and relative high intensity of cocaine (FIG. 19 panel F).

Probe Shape and Tip Angle

Figure 27A:
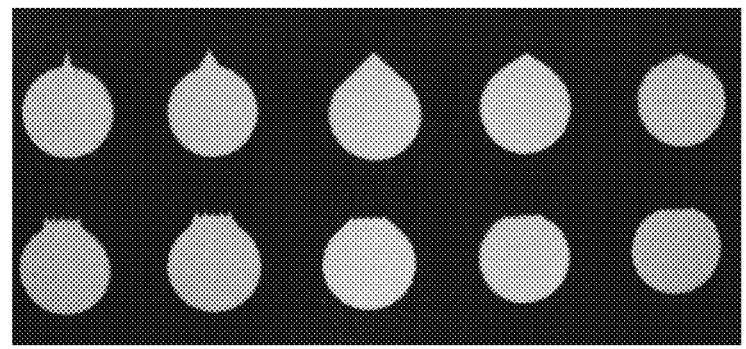
FIG. 27 panel (A) is a picture showing different tip angles for probes of the invention. From left to right, the angles are 30, 45, 90, 112, 126 degree, respectively. Panel (B) is a graph showing the effect of angle on MS signal intensity. All MS signals were normalized to the MS signal using the 90 degree tip.
Figure 27B:
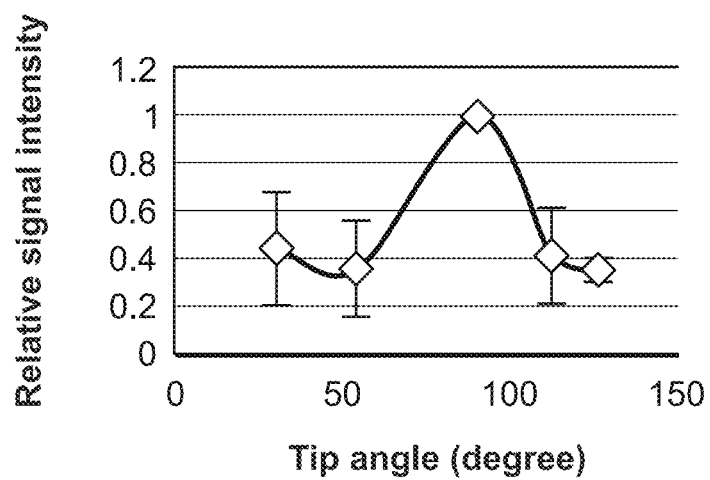

Many different probe shapes were investigated with respect to generating droplets. A preferred shape of the porous material included at least one tip. It was observed that the tip allowed ready formation of a Taylor cone. A probe shape of a triangle was used most often. As shown in FIG. 25 panels (A-C), the sharpness of the tip, the angle of the tip (FIG. 27 panels A and B), and the thickness of the paper substrate could affect the spray characteristics. The device of a tube shape with multiple tips (FIG. 25 panel D) is expected to act as a multiple-tip sprayer, which should have improved spray efficiency. An array of micro sprayers can also be fabricated on a DBS card using sharp needles to puncture the surface (FIG. 25 panel E).

Example 4: Configuration of Probe with Inlet of a Mass Spectrometer

Figure 20A:
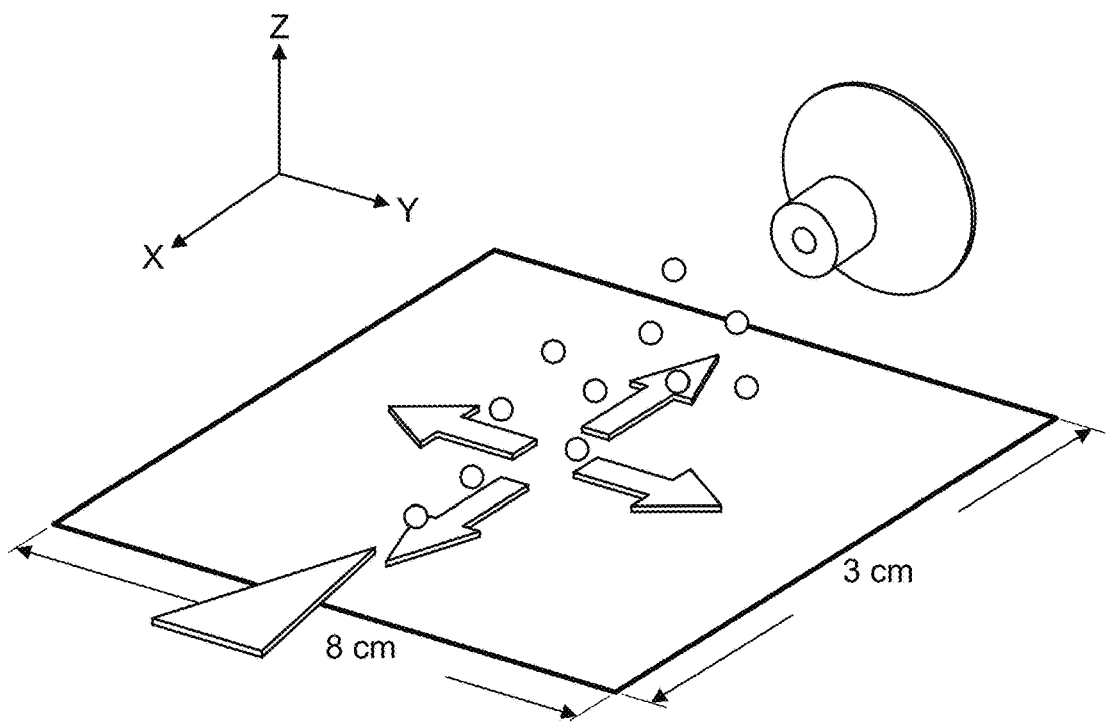
FIG. 20 panel (A) shows a schematic setup for characterizing the spatial distribution of paper spray. Panel (B) is a 2D contour plot showing the relative intensity of m/z 304 when the probe is moved in the x-y plane with respect to the inlet of the mass spectrometer. Panel (C) is a graph showing signal duration of m/z 304 when loading cocaine solution on paper with different concentrations or volumes, or sealed by Teflon membrane.
Figure 20B:
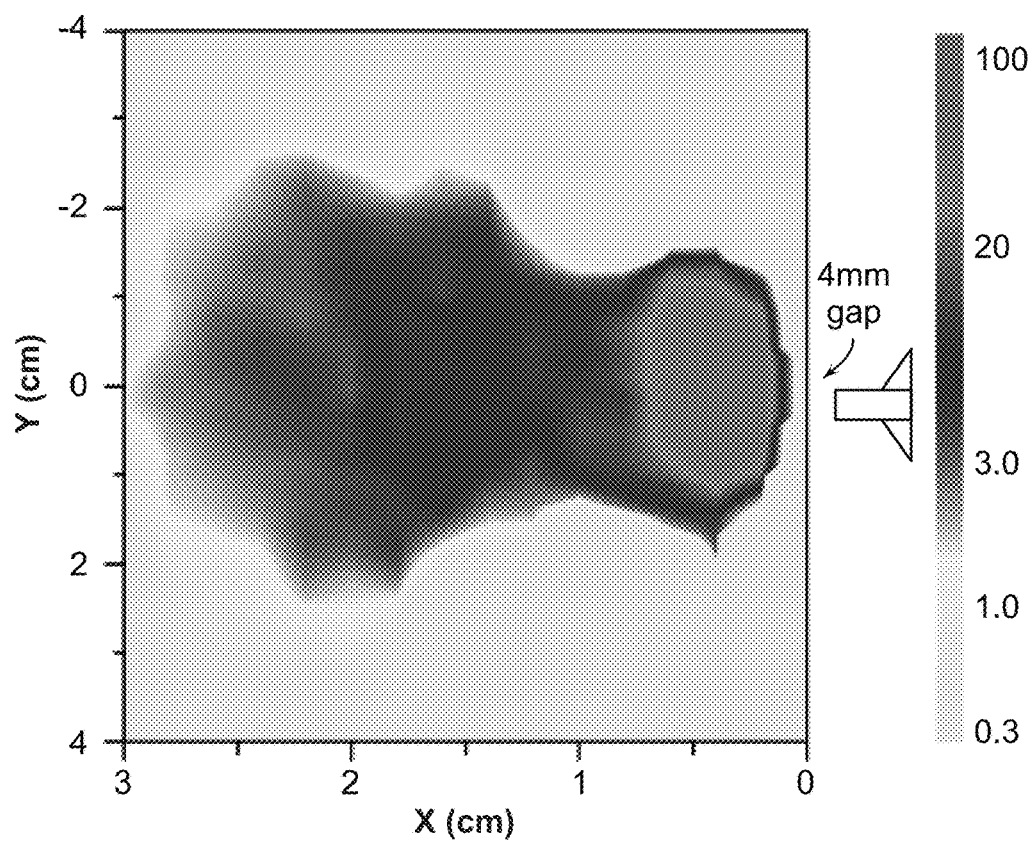
Figure 20C:
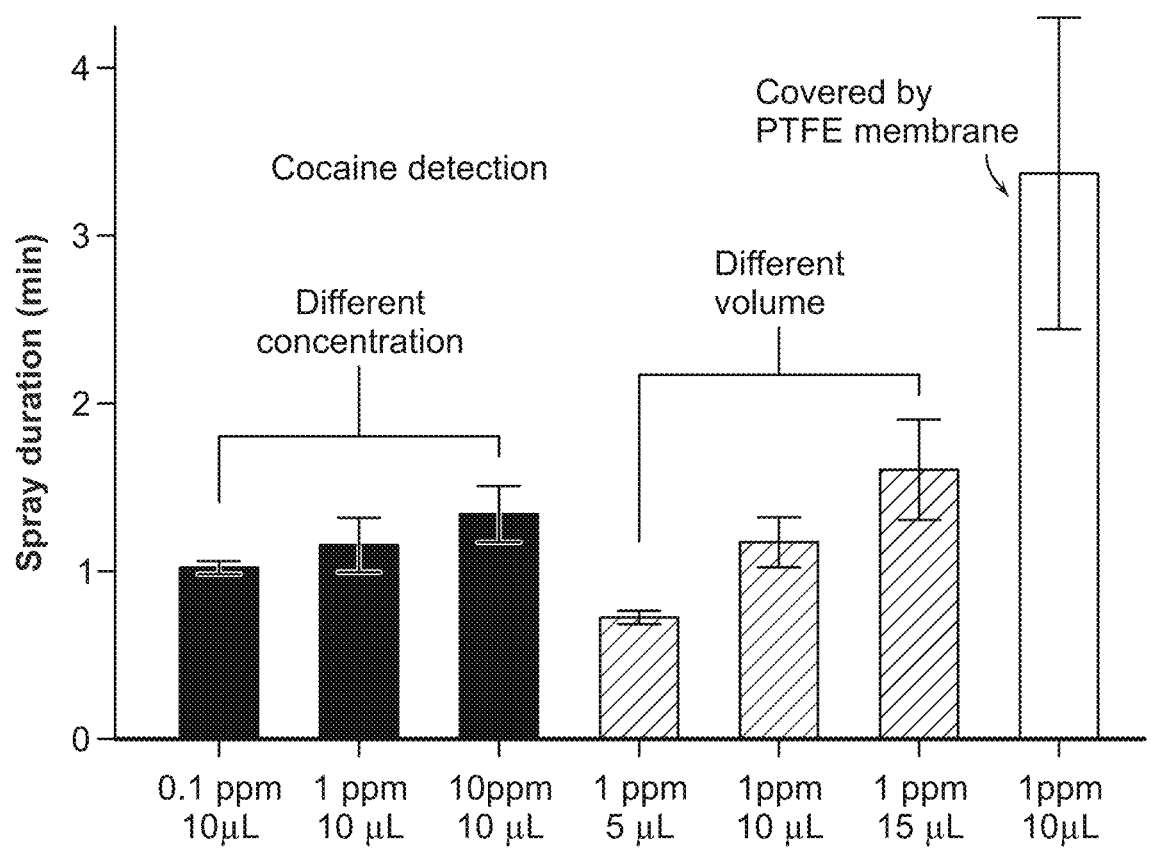
Figure 21A:
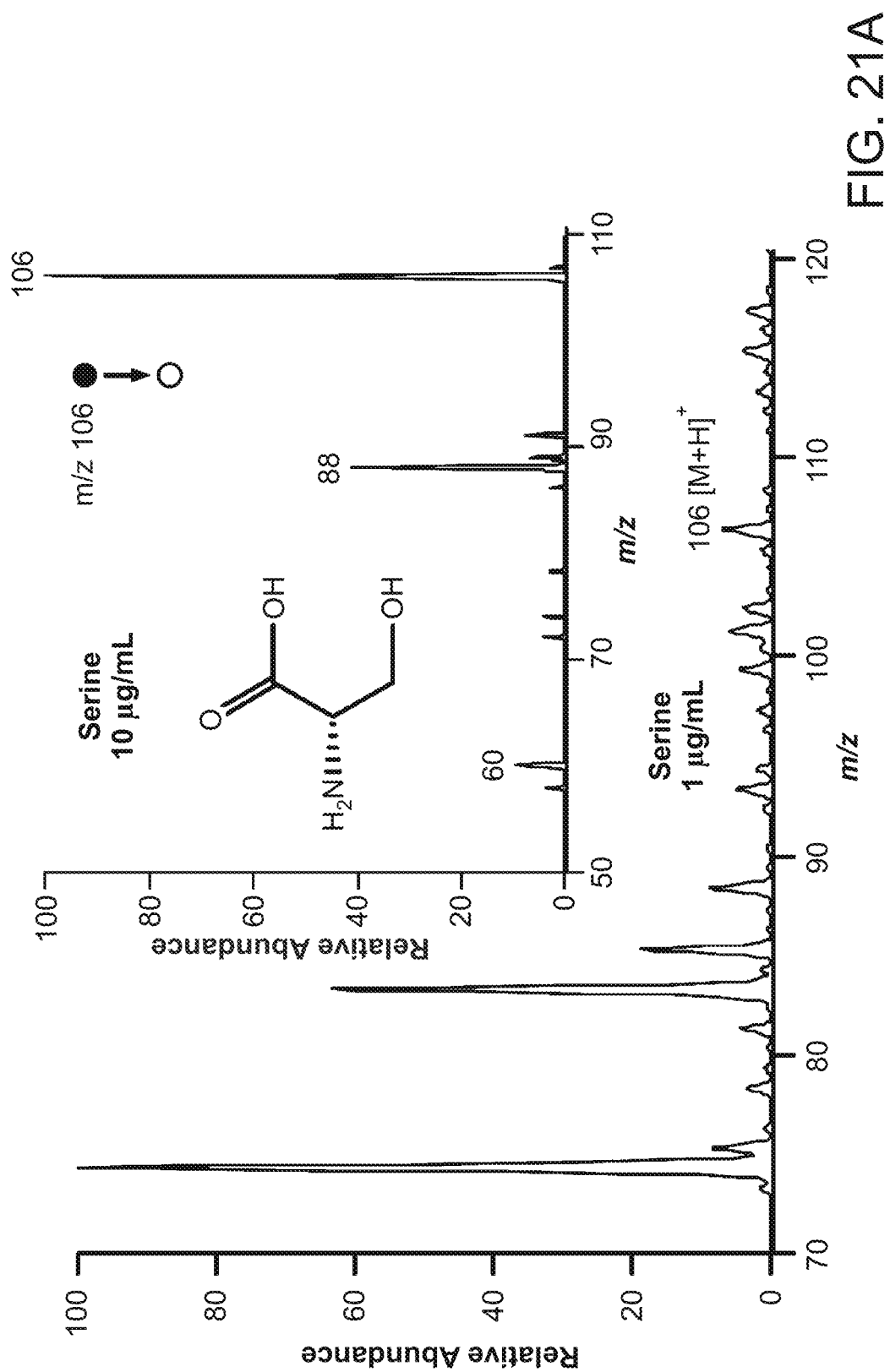
FIG. 21 is a set of MS spectra of pure chemical solutions and their corresponding MS/MS spectra. Spectra were obtained for (A) serine, (B) methadone, (C) roxithromycin, and (D) bradykinin 2-9.
Figure 21B:
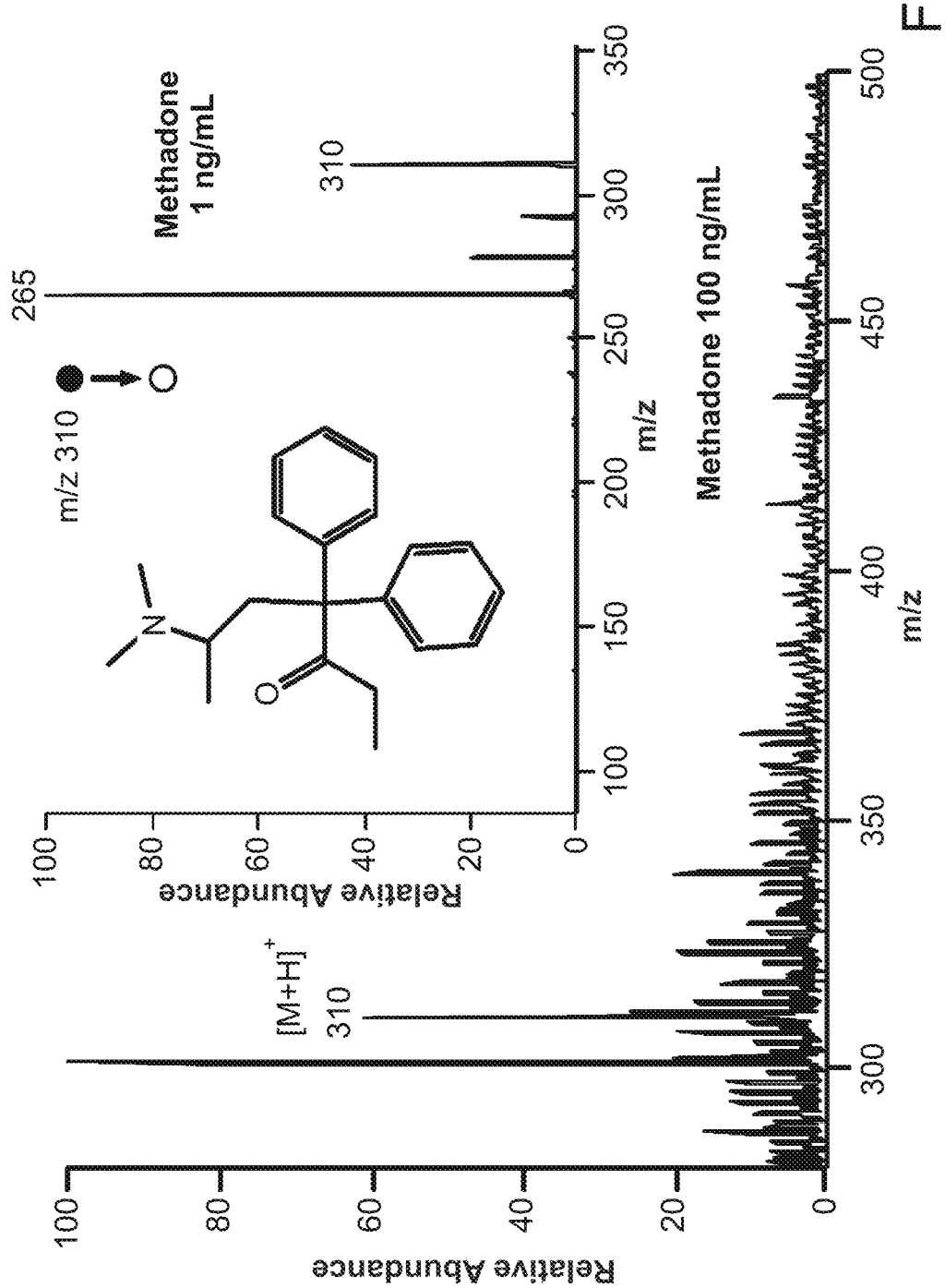
Figure 21C:
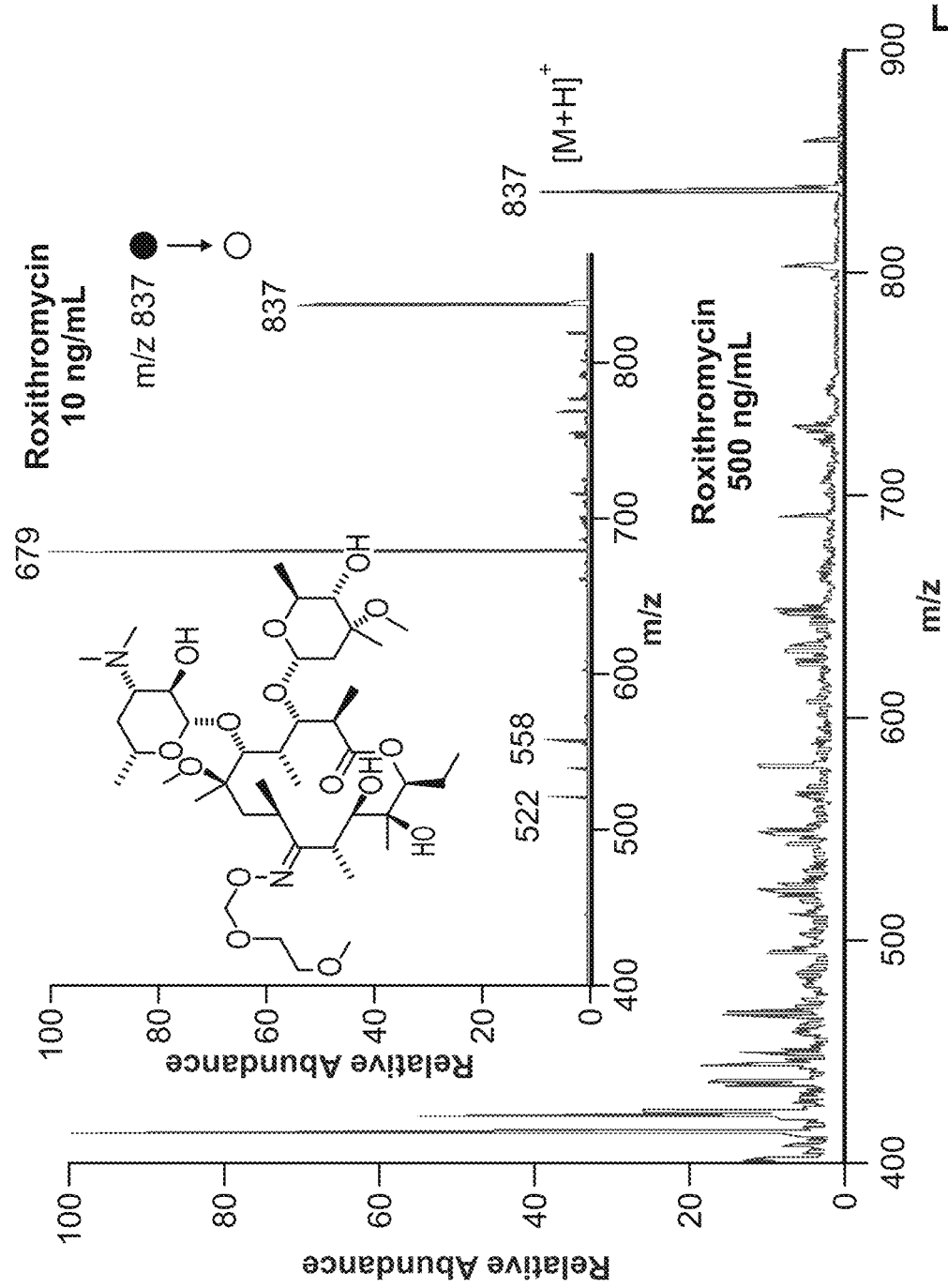
Figure 21D:
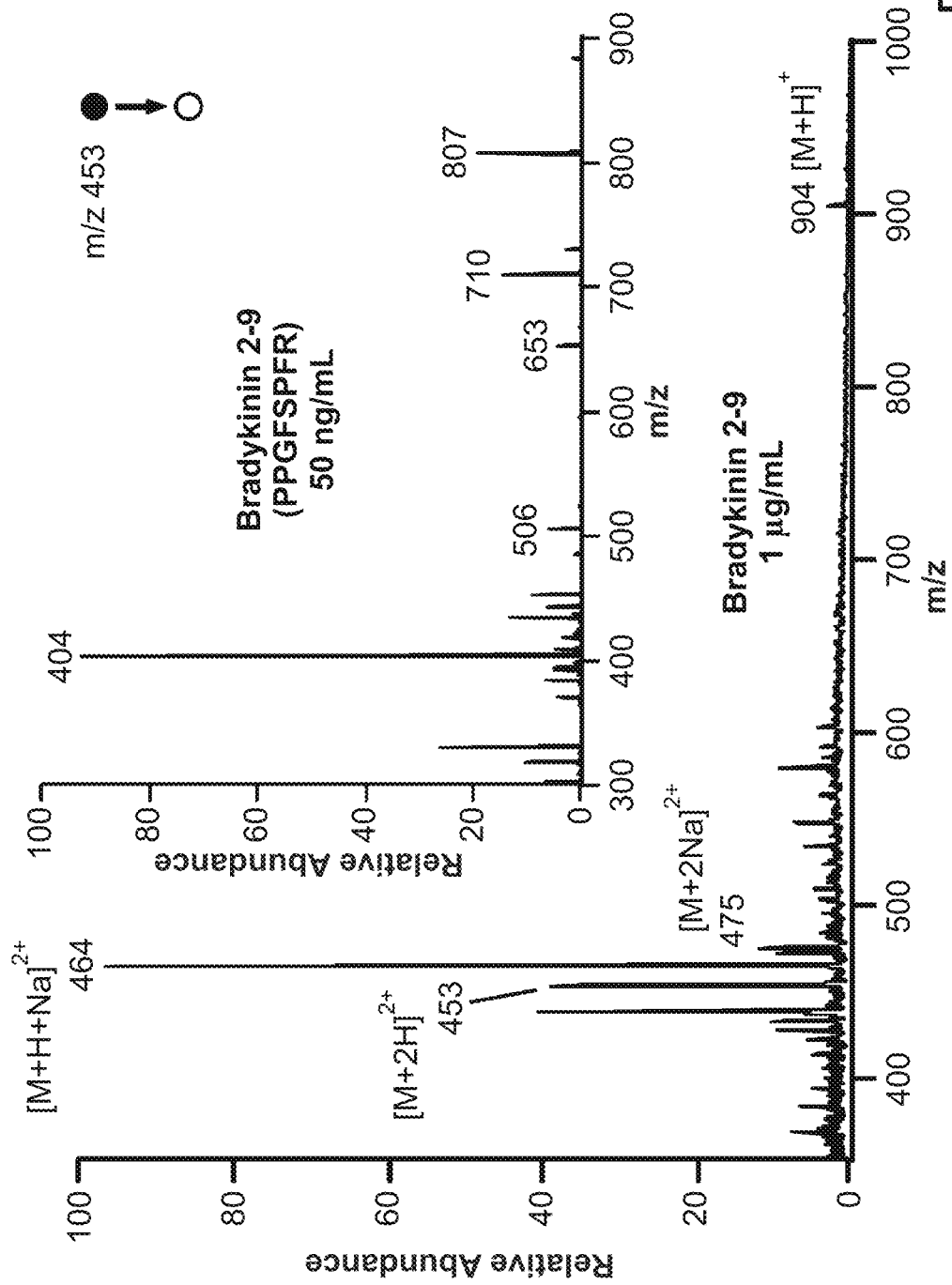
Figure 22A:
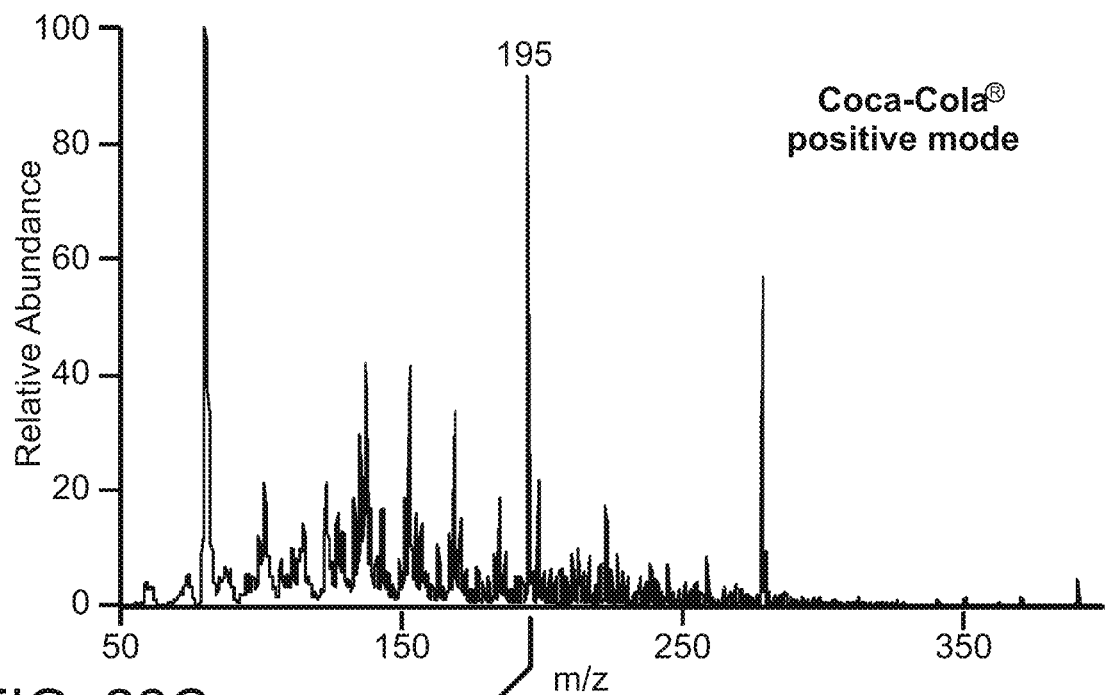
FIG. 22 is a set of mass spectra showing analysis of chemicals from complex mixtures and direct analysis from surfaces without sample preparation. Panels (A and B) are mass spectra of COCA-COLA (cola drink), which was directly analyzed on paper in both of (A) positive and (B) negative mode. Panel (C) is a mass spectrum of caffeine. Panel (D) is a mass spectrum of potassium benzoate. Panel (E) is a mass spectrum of acesulfame potassium. Panel (F) is a mass spectrum of caffeine detected from urine. Panel (G) is a mass spectrum of heroin detected directly from a desktop surface after swabbing of the surface by probes of then invention.
Figure 22C:
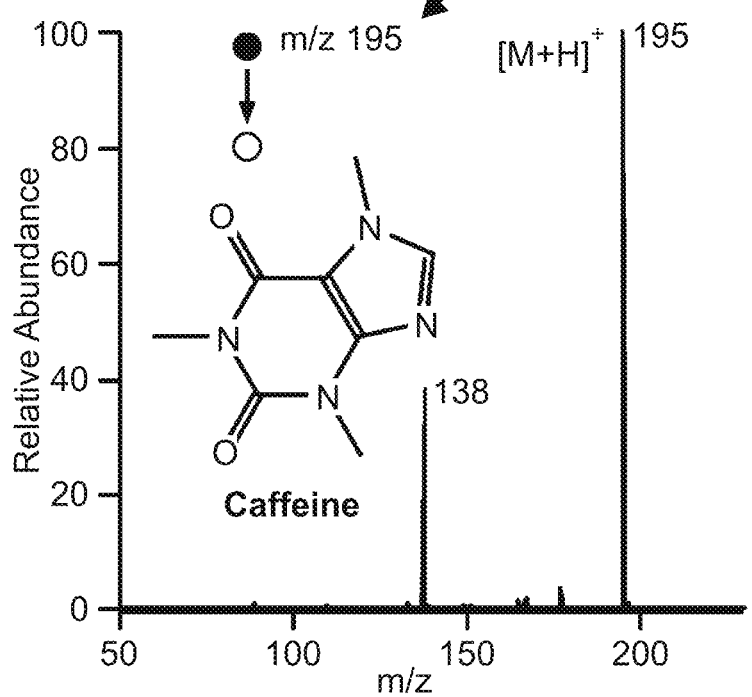
Figure 22B:
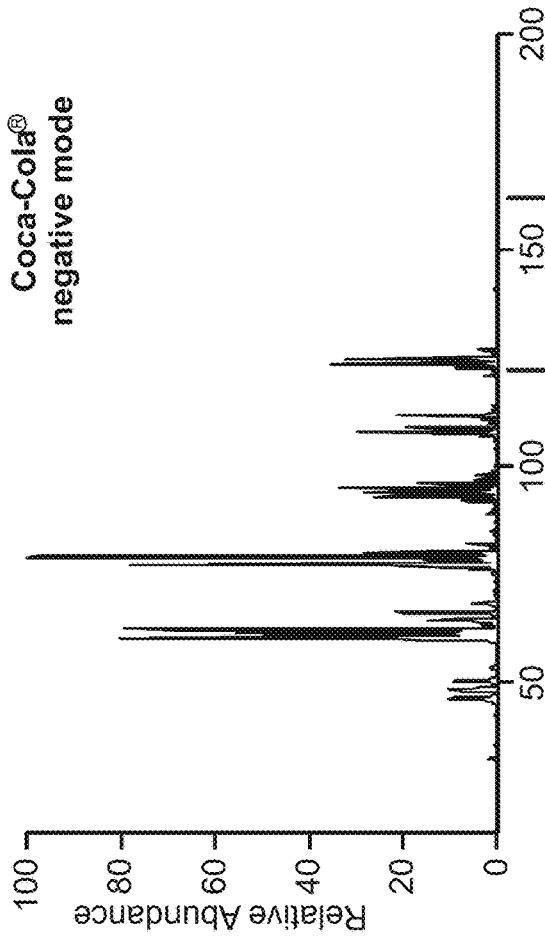
Figure 22E:
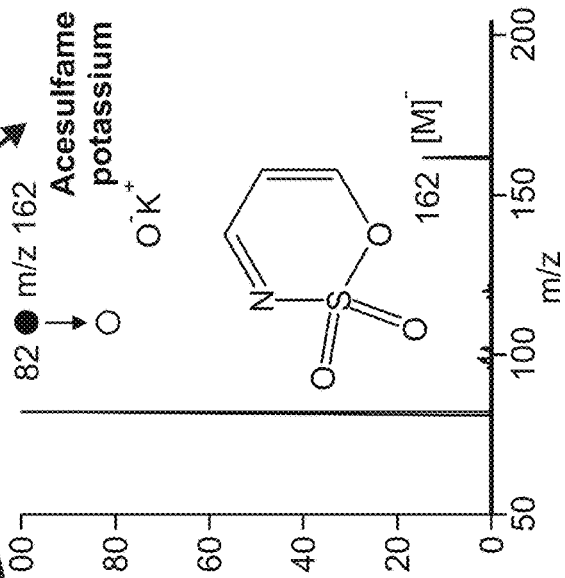
Figure 22D:
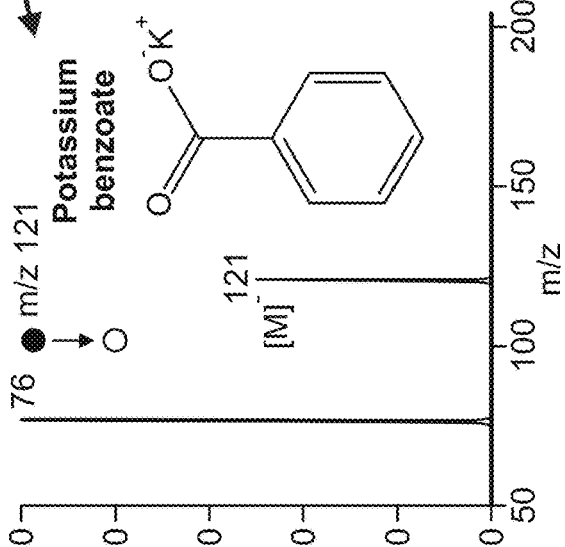
Figure 22F:
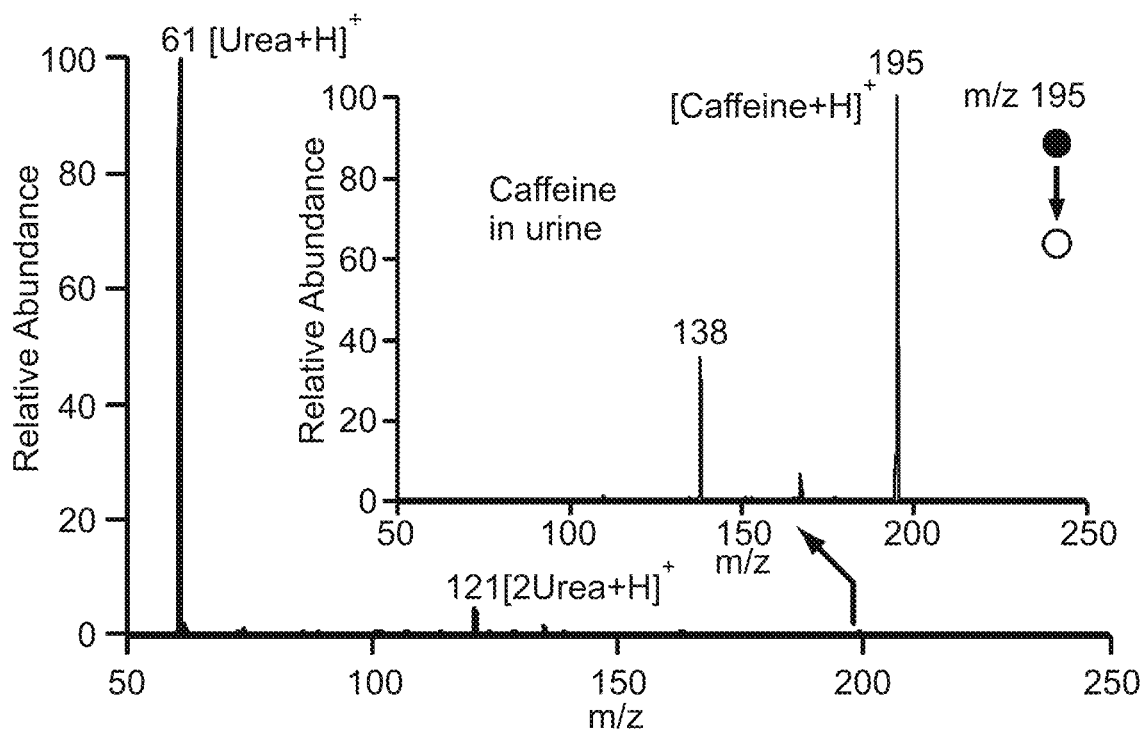
Figure 22G:
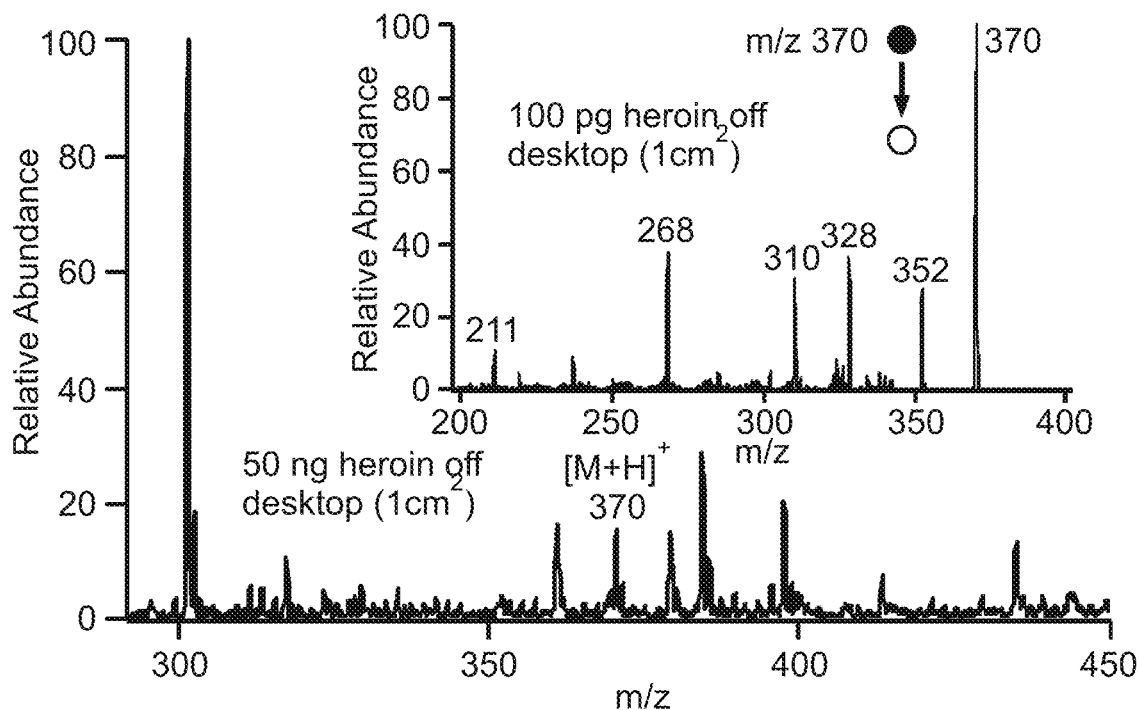

A paper triangle was mounted on a 2D moving stage to determine how the mass signal was affected by the relative positions of the paper triangle and the mass spectrometer inlet. The paper triangle was moved 8 cm in the y-direction in a continuous manner and 3 cm in the x-direction with a 2 mm increment for each step (FIG. 20 panel A). Cocaine solution (1 ug/mL, methanol/water, 1:1 v/v) was continuously fed onto the paper surface. The mass spectrum was continuously recorded during the entire scan. A contour plot of the peak intensity of protonated cocaine (m/z, 304) was created from the normalized data extracted from the mass spectrum (FIG. 20 panel B). The contour plot shows that it was not necessary for the paper triangle to be placed directly in-line with the inlet of the mass spectrometer to generate droplets.

Spray duration was also tested (FIG. 20 Panel C). Paper triangles (size 10 mm, 5 mm) were prepared. First, 10 uL solutions were applied on the paper triangles with different concentration of 0.1, 1 and 10 ug/mL. The spray time for each paper was just slightly varied by the difference of concentration. After that, 1 ug/mL cocaine solutions were applied on the paper triangles with different volumes of 5 uL, 10 uL and 15 uL. The spray times showed a linear response followed by the increasing sample volumes.

In another test, the paper was sealed with a PTFE membrane to prevent evaporation of solution, which prolonged the spray time by about three times. These results indicate that paper spray offers long enough time of spray for data acquisition even using 5 uL solution, and the intensity of signal is stable during the entire spray period.

Example 5: Separation and Detection

Figure 24:
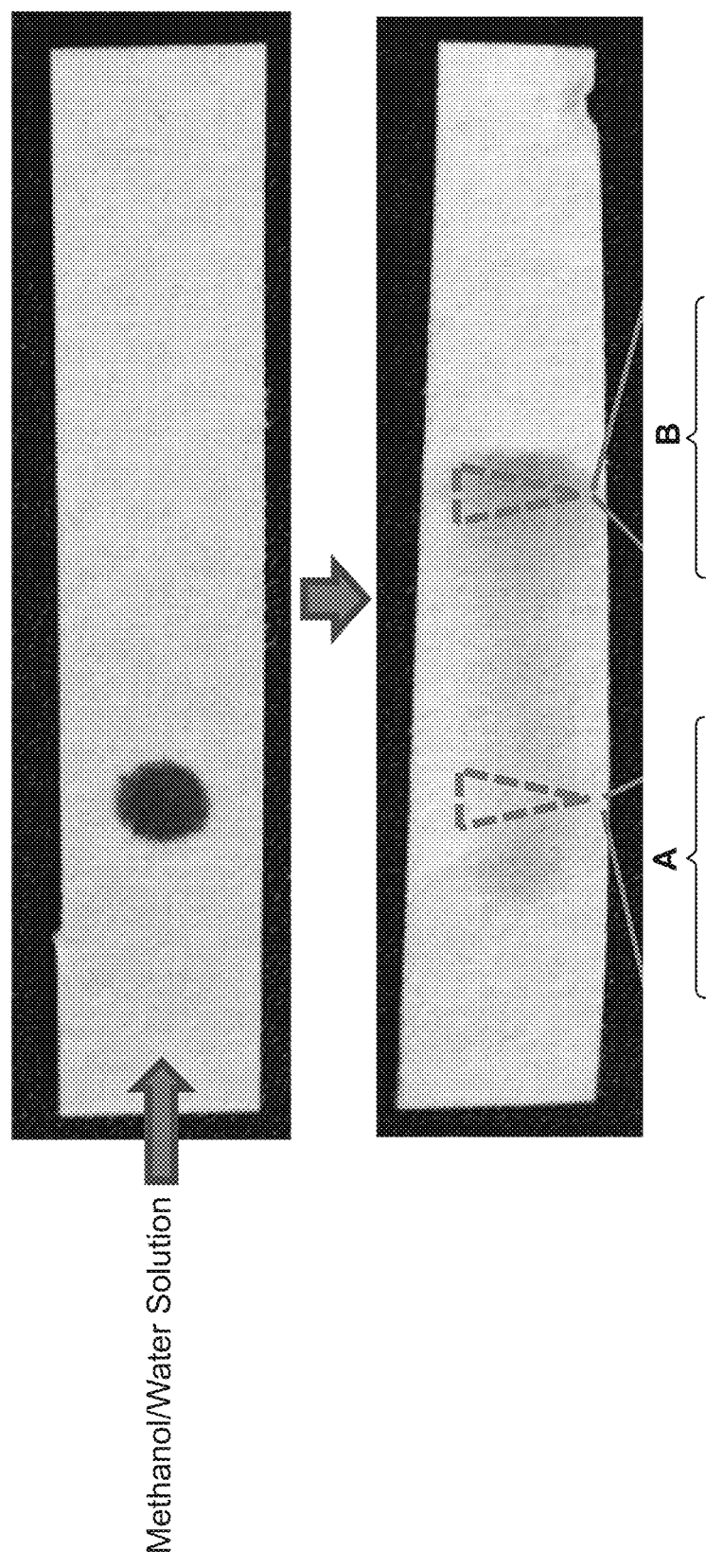
FIG. 24 shows analysis of two dyes, methylene blue (m/z 284) and methyl violet (m/z 358.5), separated by TLC. Dye mixture solution (0.1 µl of a 1 mg/mL solution) was applied onto the chromatography paper (4 cm×0.5 cm) and dried before TLC and paper spray MS analysis.
Figure 24:
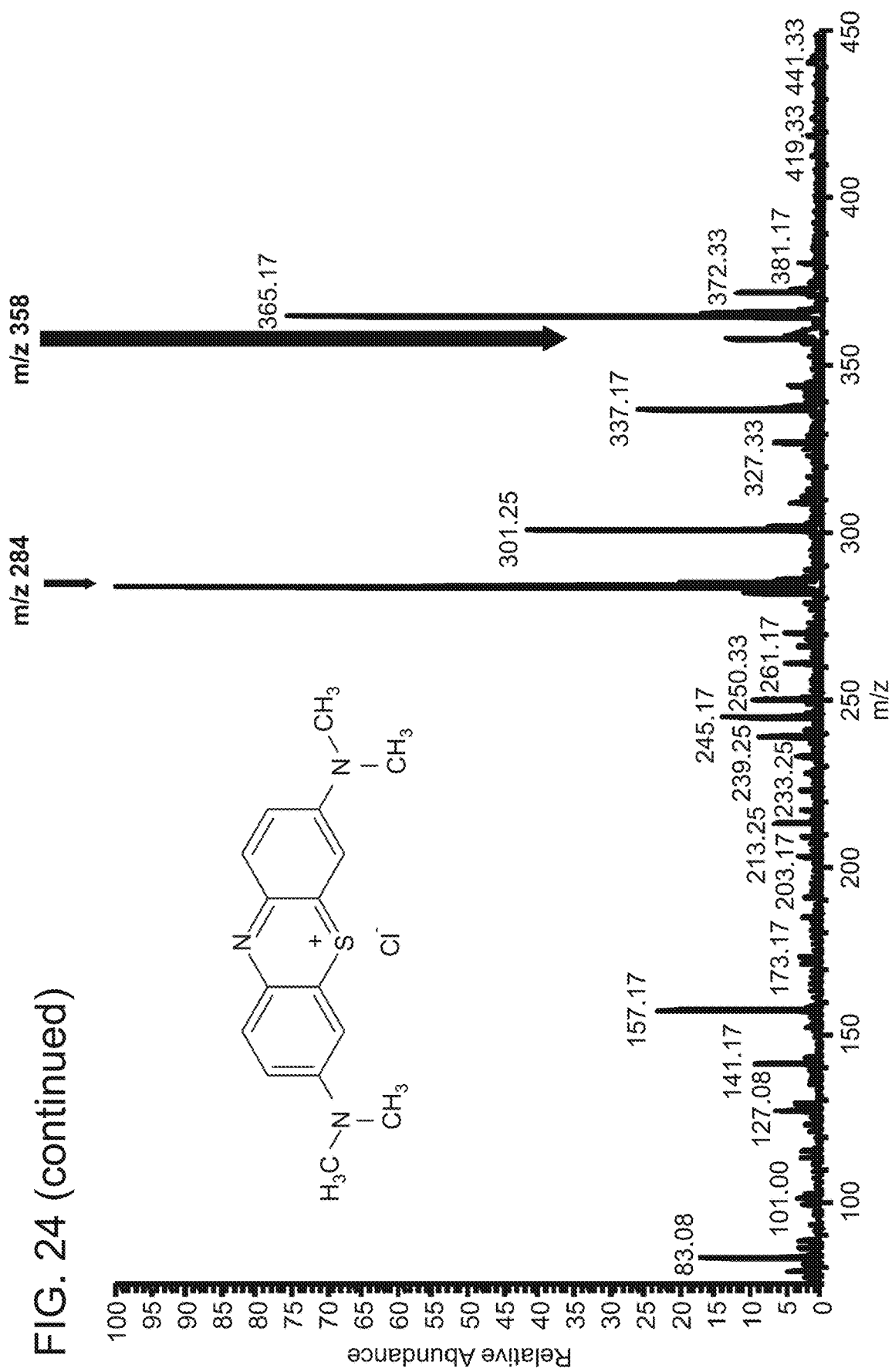
Figure 24:
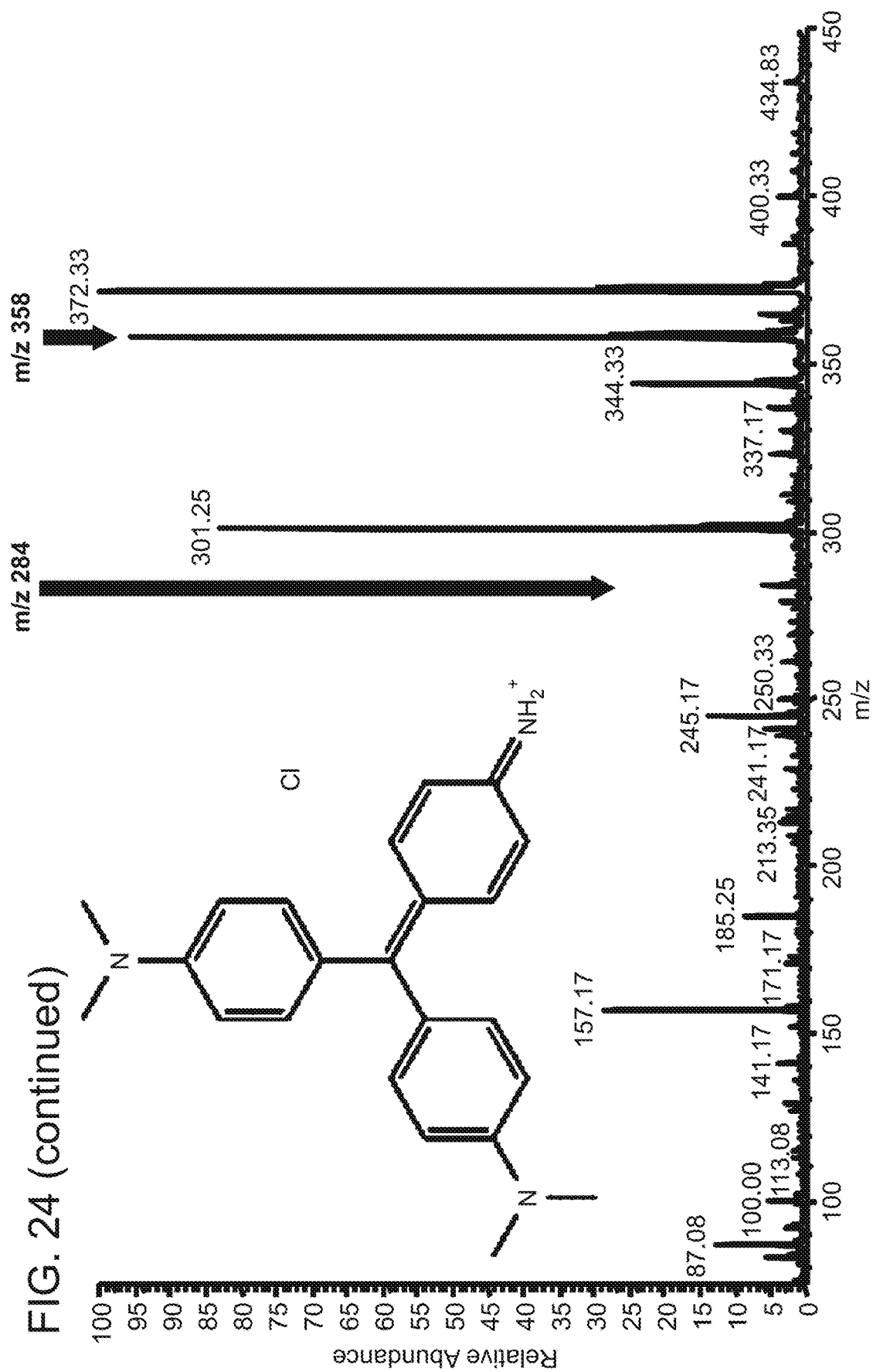
Figure 25C:
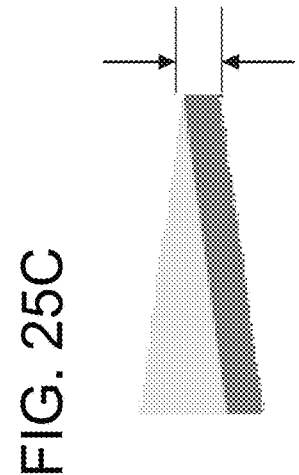
FIG. 25 shows different shapes, thicknesses, and angles for probes of the invention. Panel (A) shows sharpness. Panel (B) shows angle of the tip. Panel (C) shows thickness of the paper. Panel (D) shows a device with multiple spray tips. Panel (E) shows a DBS card with micro spray tips fabricated with sharp needles.
Figure 25B:
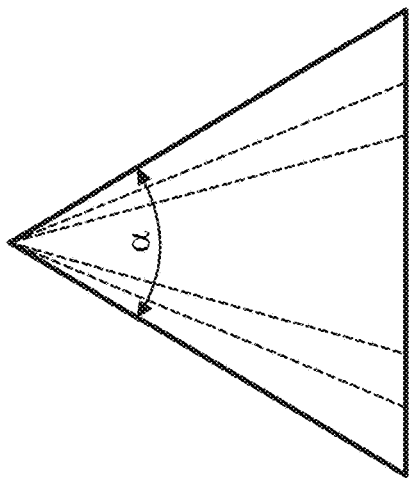
Figure 25A:
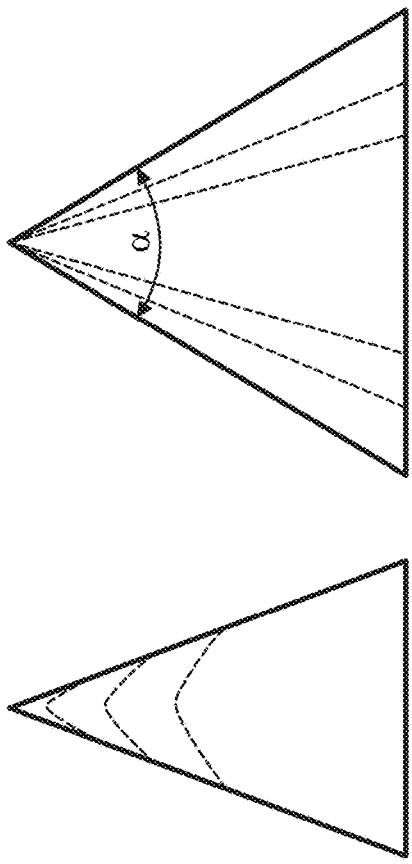
Figure 25E:
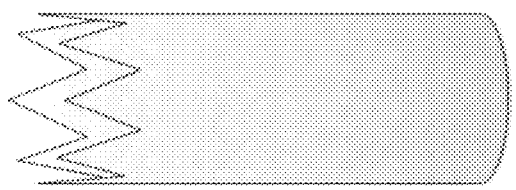
Figure 25D:
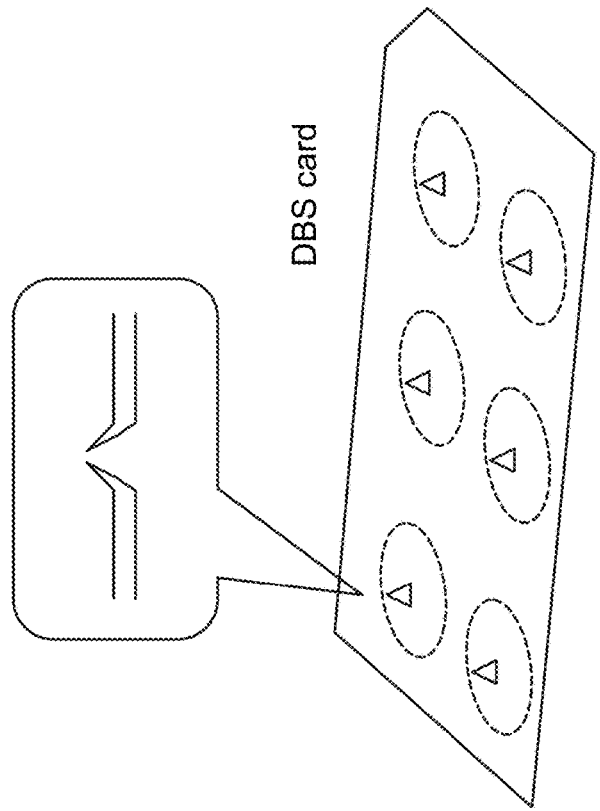
Figure 26A:
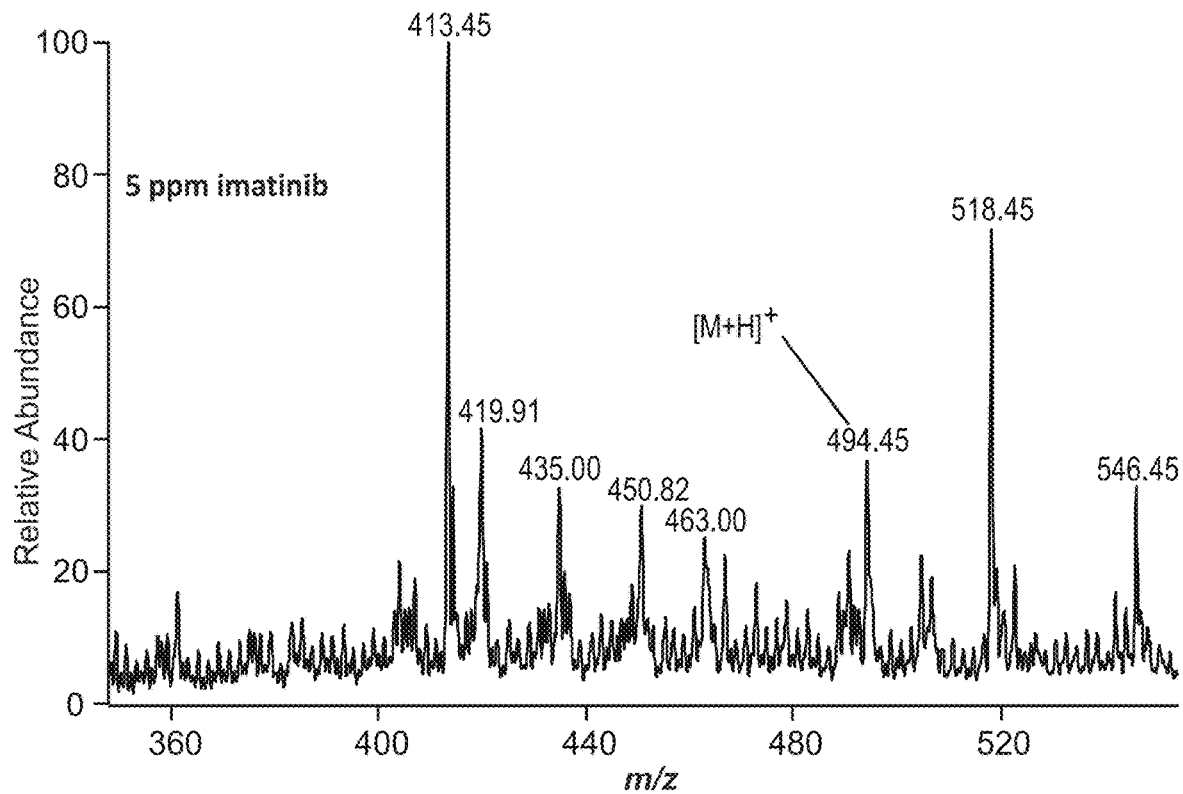
FIG. 26 is a set of mass spectra of imatinib from human serum using direct spray from a C4 zip-tip of conical shape. Human serum samples (1.5 µL each) containing imatinib were passed through the porous C4 extraction material three times and then 3 µL methanol was added onto the zip-tip with 4 kV positive DC voltage applied to produce the spray. Panel (A) shows a MS spectrum for 5 µg/mL. Panel (B) shows a MS/MS spectrum for 5 ng/mL.
Figure 26B:
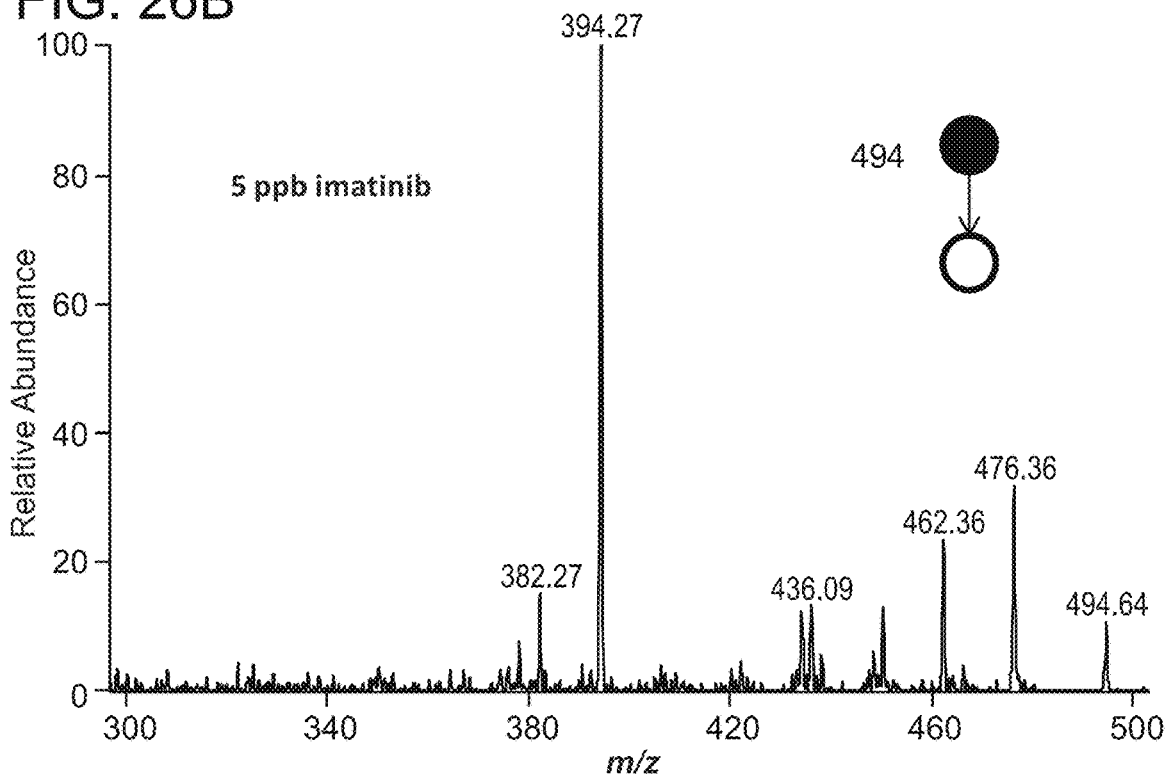

Probes of the invention include a porous material, such as paper, that can function to both separate chemicals in biological fluids before in situ ionization by mass spectrometry. In this Example, the porous material for the probe was chromatography paper. As shown in FIG. 24, a mixture of two dyes was applied to the paper as a single spot. The dyes were first separated on the paper by TLC (thin layer chromatograph) and the separated dyes were examined using MS analysis by methods of the invention with the paper pieces cut from the paper media (FIG. 24). Data show the separate dyes were detected by MS analysis (FIG. 24).

The chromatography paper thus allowed for sample collection, analyte separation and analyte ionization. This represents a significant simplification of coupling chromatography with MS analysis. Chromatography paper is a good material for probes of the invention because such material has the advantage that solvent movement is driven by capillary action and there is no need for a syringe pump. Another advantage is that clogging, a serious problem for conventional nanoelectrospray sources, is unlikely due to its multi-porous characteristics. Therefore, chromatography paper, a multi-porous material, can be used as a microporous electrospray ionization source.

Example 6: Pure Compounds: Organic Drugs, Amino Acids, and Peptides

As already described, probes and methods of the invention offer a simple and convenient ionization method for mass spectrometry. Paper triangles were spotted with different compounds and connected to a high voltage source to produce ions. All experiments were carried out with a Finnigan LTQ mass spectrometer (Thermo Electron, San Jose, Calif.). Data herein show that a variety of chemicals could be ionized in solution phase, including amino acid, therapeutic drugs, illegal drugs and peptides.

Figure 2A:
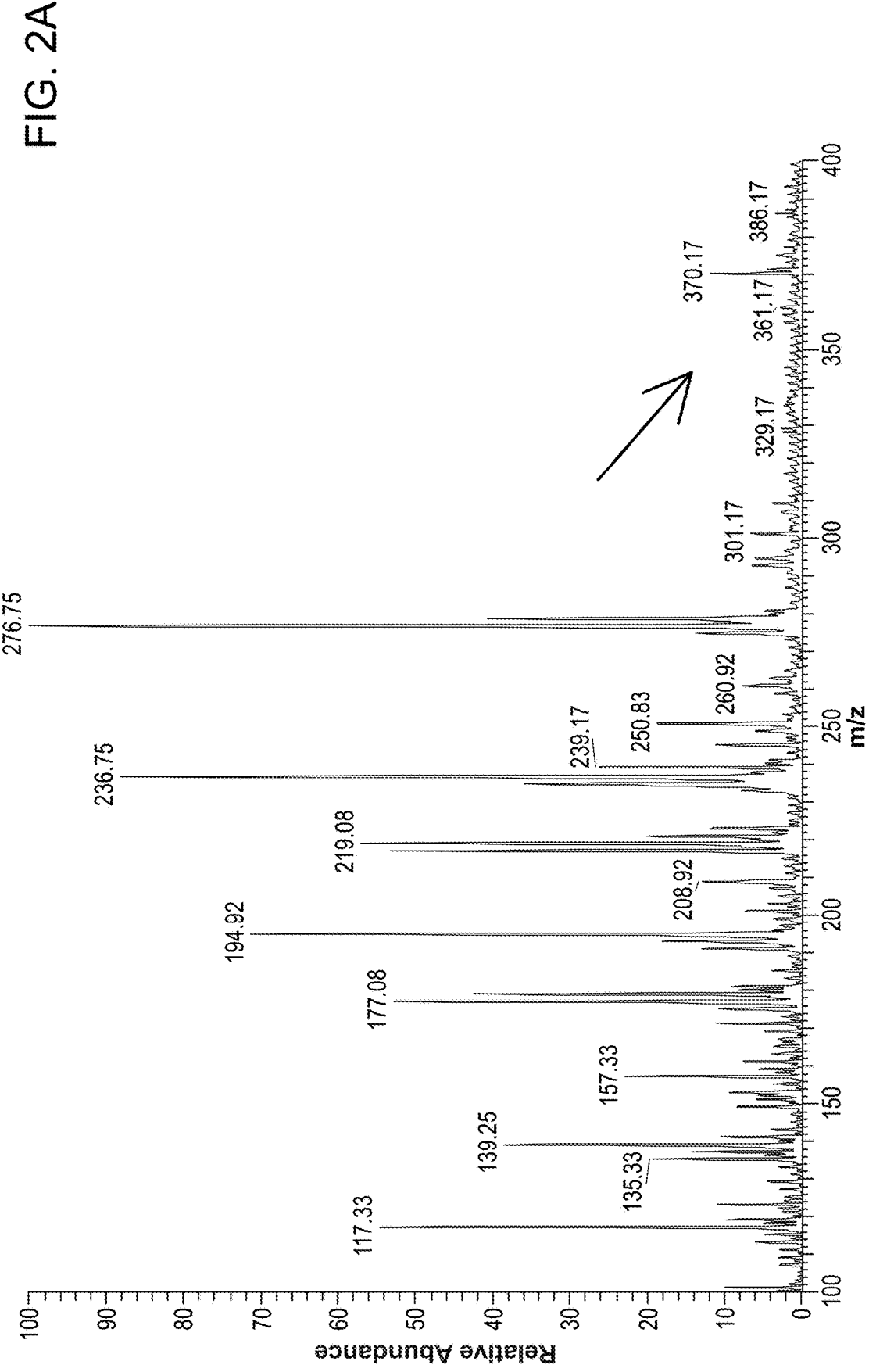
FIG. 2 panel (A) is a MS spectrum of heroin (concentration: 1 ppm, volume: 10 μl, solvent: MeOH/H$_2$O/HOAc (50:49:1, v/v/v)) using probes of the invention.
Figure 2B:
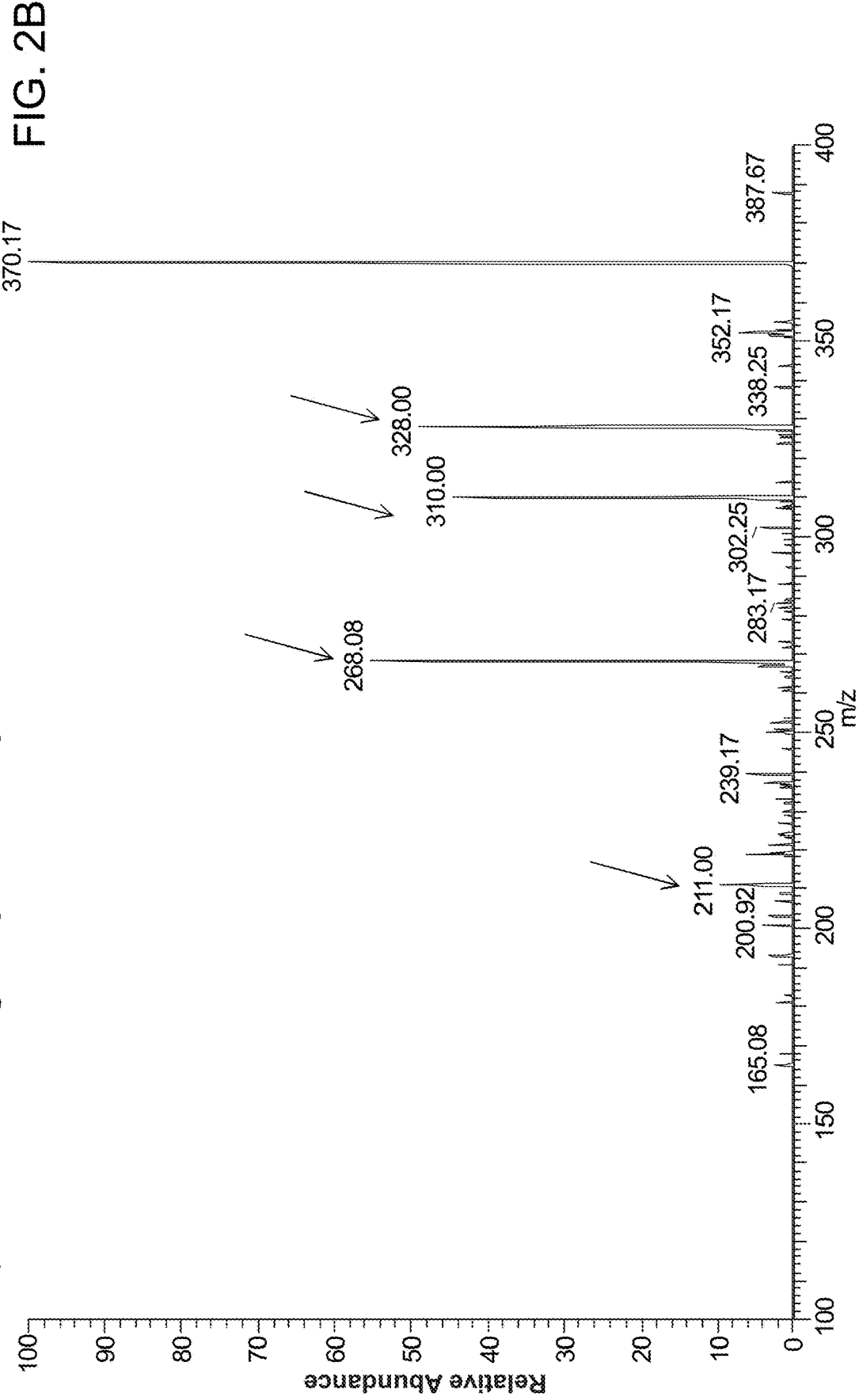

FIG. 2 panel (A) shows an MS spectrum of heroin (concentration: 1 ppm, volume: 10 µl, solvent: MeOH/H$_2$O/HOAc (50:49:1, v/v/v)) using probes of the invention. FIG. 2 panel (B) shows MS/MS spectrum of heroin (concentration: 1 ppb, volume: 10 µl, solvent: MeOH/H$_2$O/HOAc (50:49:1, v/v/v)).

Figure 3A:
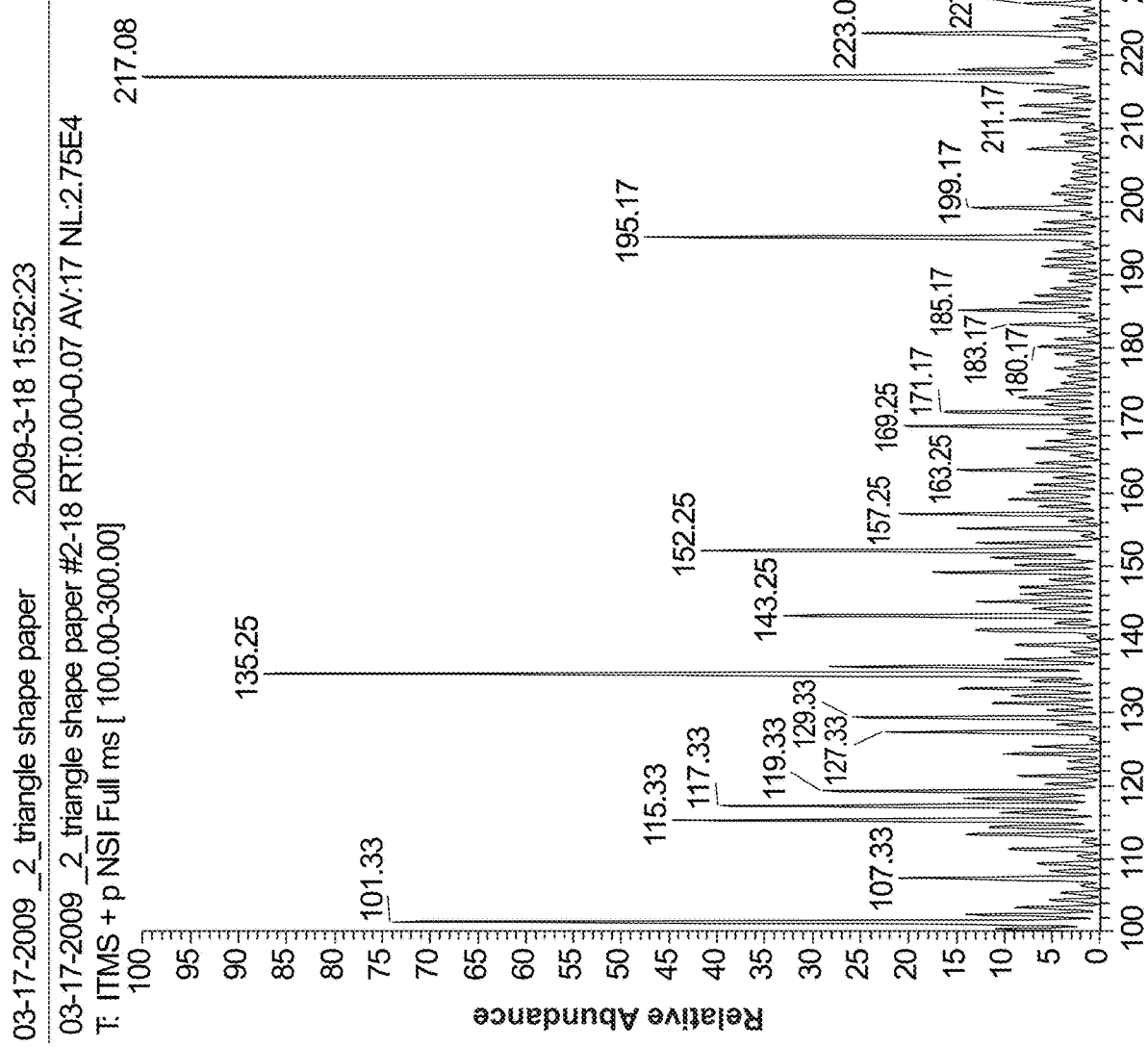
FIG. 3 panel (A) is a MS spectrum of caffeine (concentration: 10 ppm, volume: 10 μl, solvent: MeOH/H$_2$O/HOAc (50:49:1, v/v/v)) using probes of the invention.
Figure 3B:
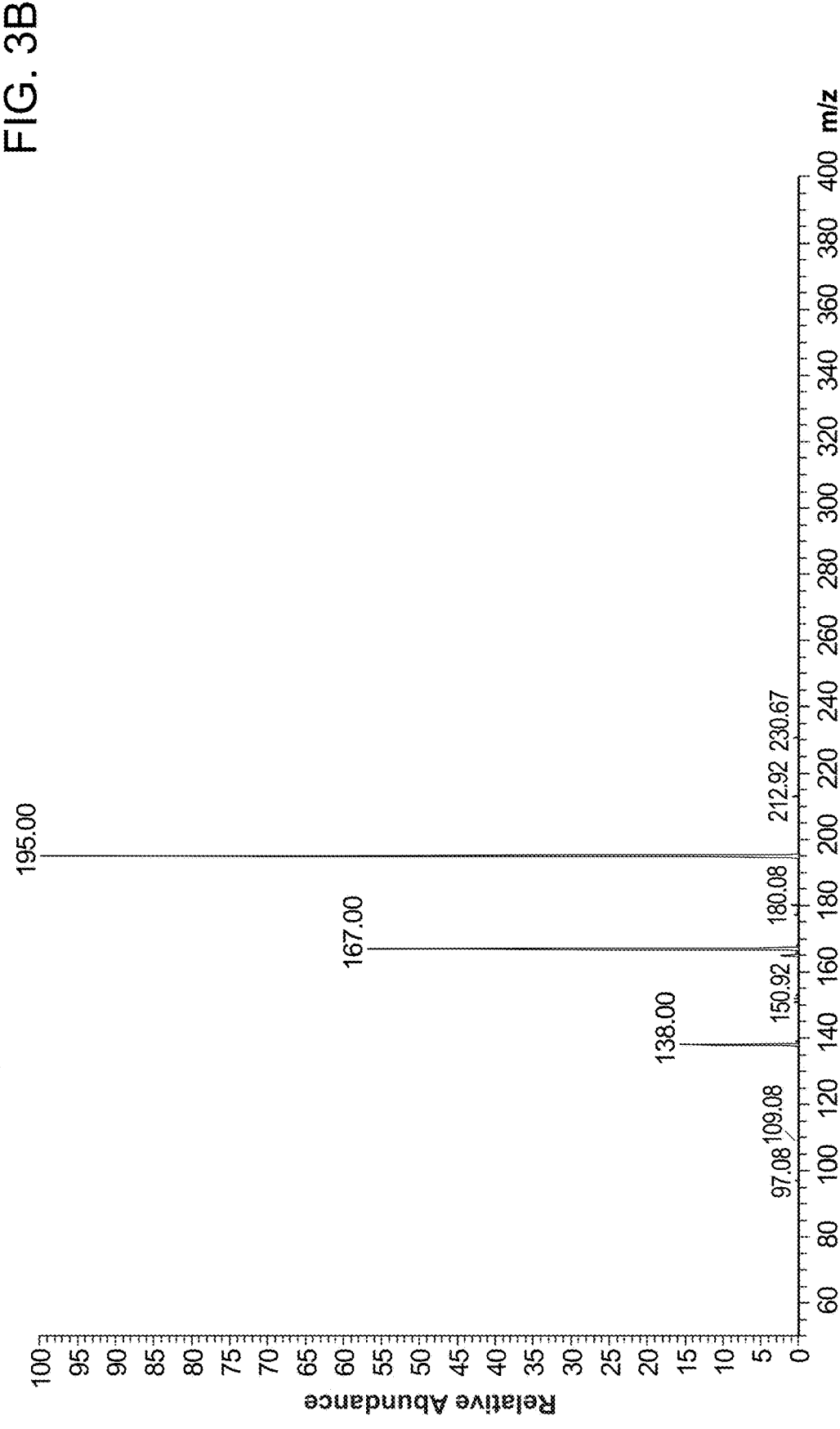

FIG. 3 panel (A) shows MS spectrum of caffeine (concentration: 10 ppm, volume: 10 µl, solvent: MeOH/H$_2$O/HOAc (50:49:1, v/v/v)) using probes of the invention. FIG. 3 panel (B) shows MS/MS spectrum of caffeine (concentration: 10 ppb, volume: 10 µl, solvent: MeOH/H$_2$O/HOAc (50:49:1, v/v/v)). Peak 167 also exists in the blank spectrum with solvent and without caffeine.

Figure 4A:
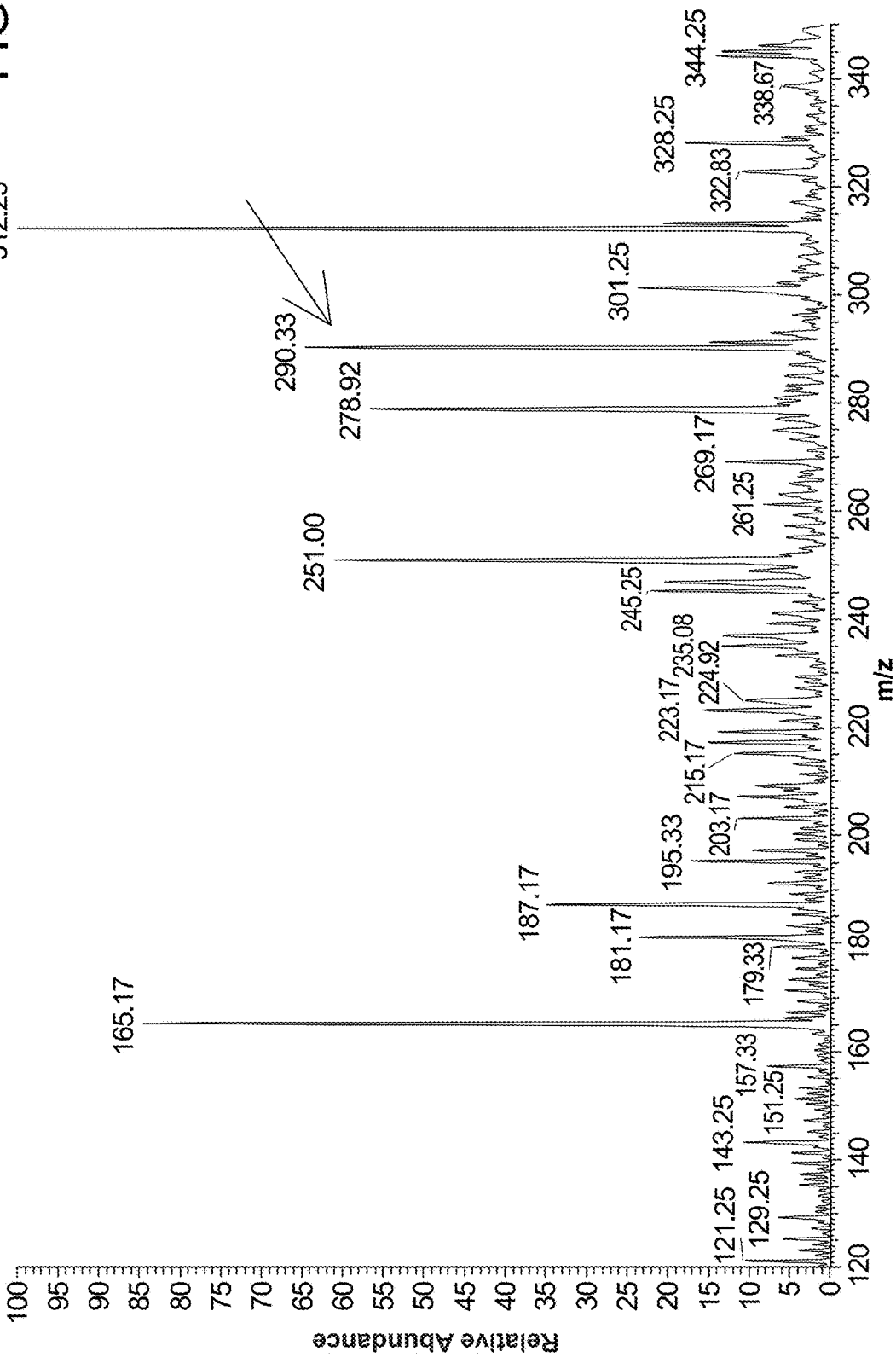
FIG. 4 panel (A) is a MS spectrum of benzoylecgonine (concentration: 10 ppm, volume: 10 μl, solvent: MeOH/H$_2$O/HOAc (50:49:1, v/v/v)) using probes of the invention.
Figure 4B:
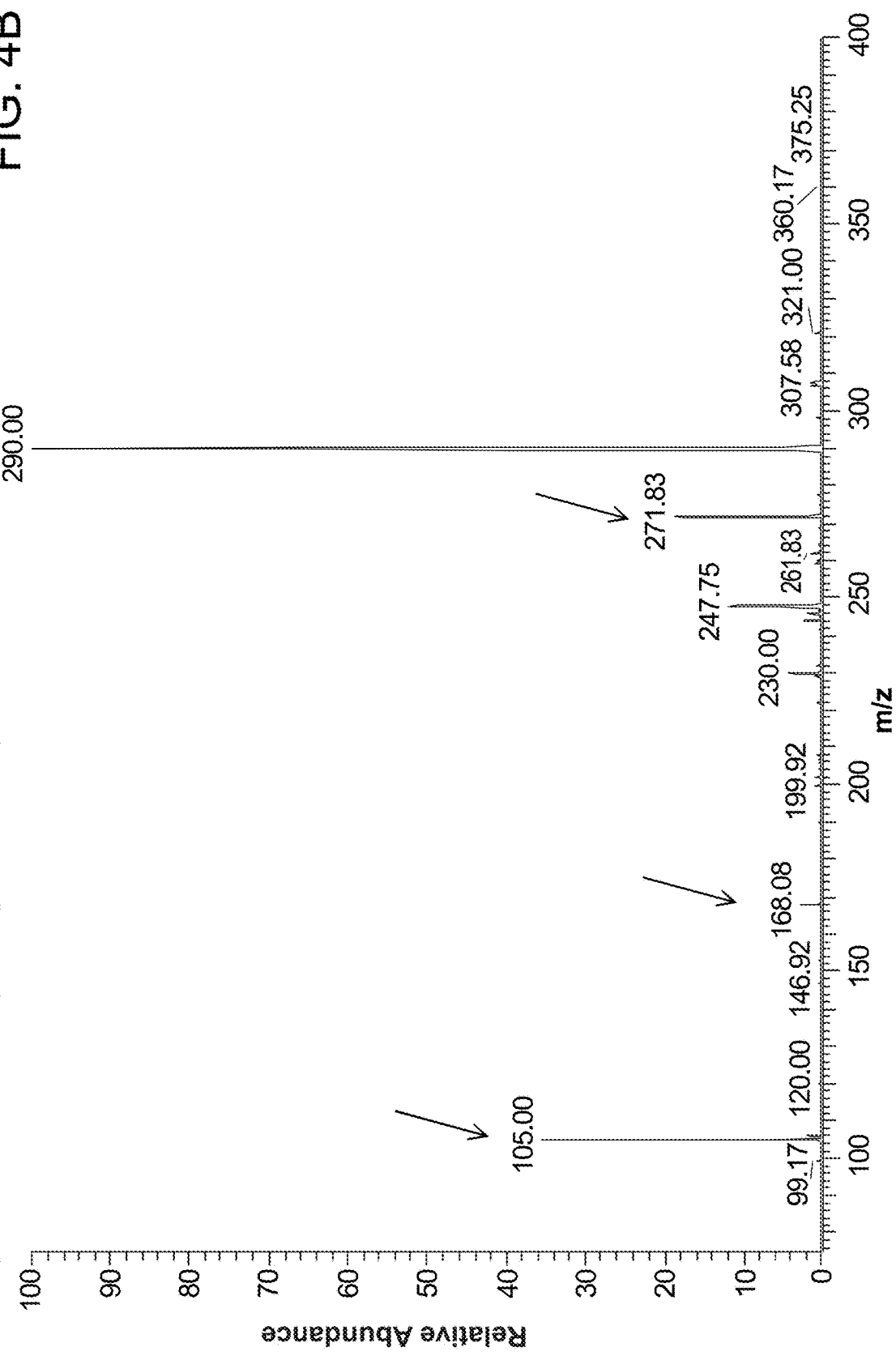

FIG. 4 panel (A) shows MS spectrum of benzoylecgonine (concentration: 10 ppm, volume: 10 µl, solvent: MeOH/H$_2$O/HOAc (50:49:1, v/v/v)) using probes of the invention. FIG. 4 panel (B) shows MS/MS spectrum of benzoylecgonine (concentration: 10 ppb, volume: 10 µl, solvent: MeOH/H$_2$O/HOAc (50:49:1, v/v/v)).

Figure 5A:
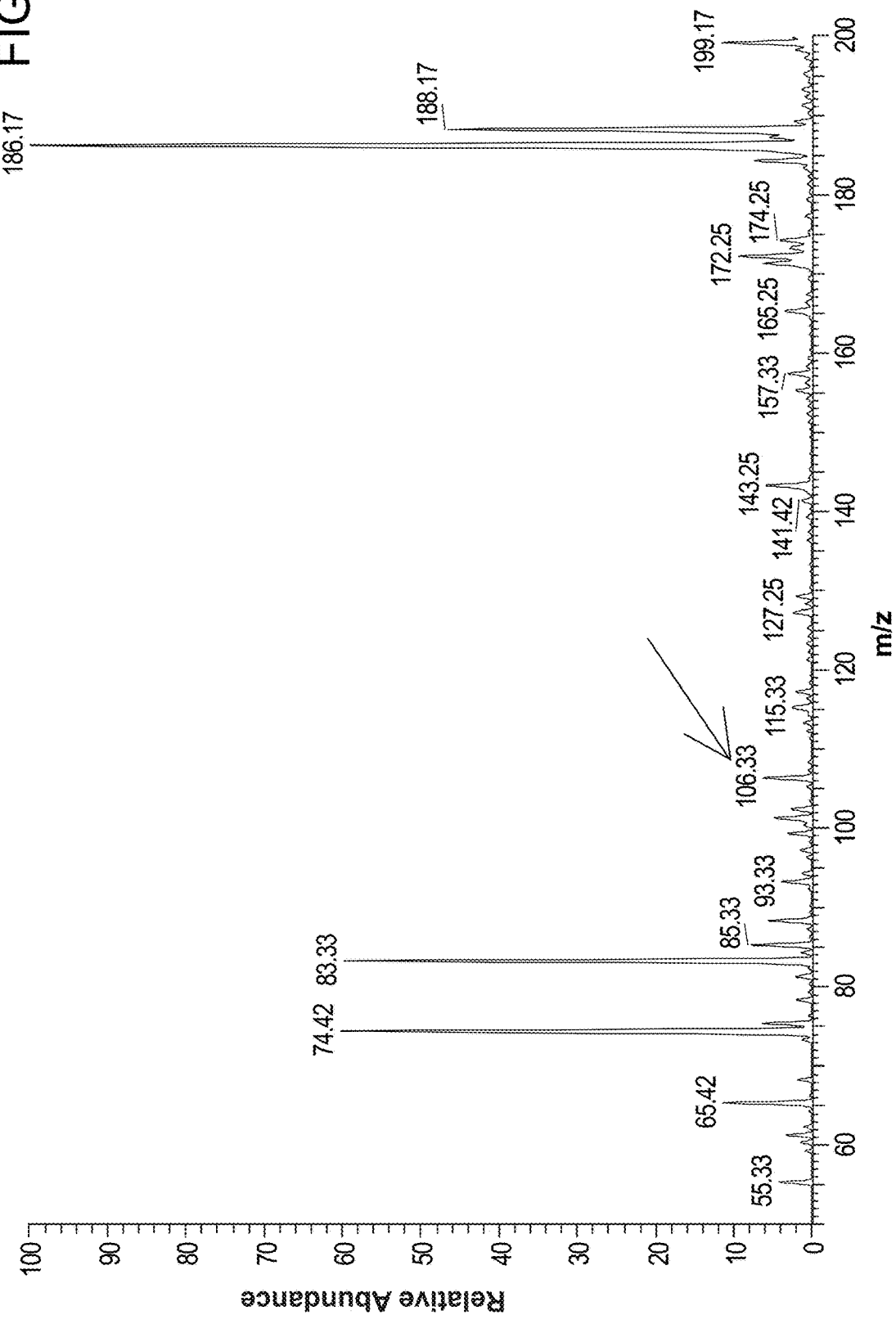
FIG. 5 panel (A) is a MS spectrum of serine (concentration: 1 ppm, volume: 10 μl, solvent: MeOH/H$_2$O/HOAc (50:49:1, v/v/v)) using probes of the invention.
Figure 5B:
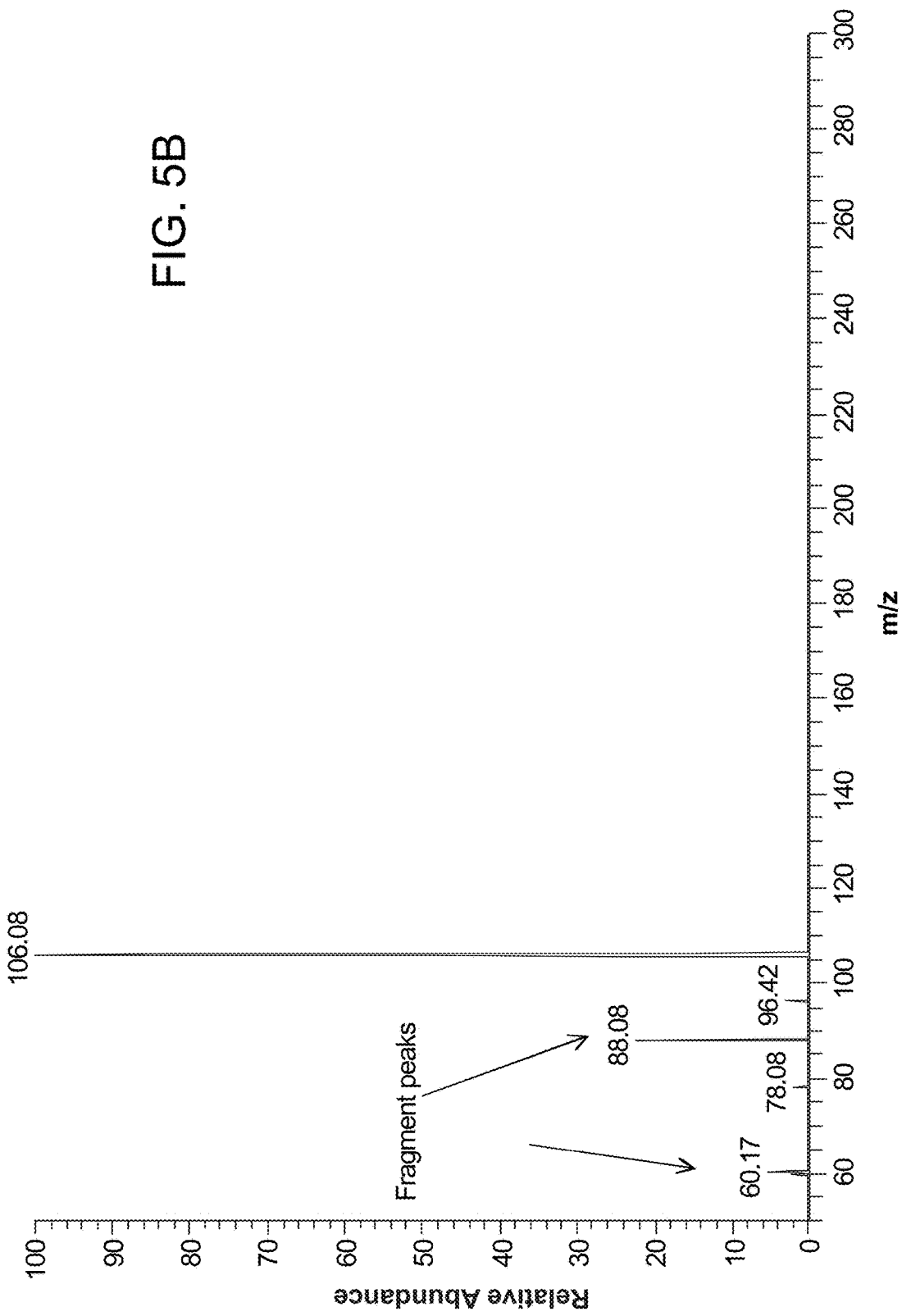

FIG. 5 panel (A) shows MS spectrum of serine (concentration: 1 ppm, volume: 10 µl, solvent: MeOH/H$_2$O/HOAc (50:49:1, v/v/v)) using probes of the invention. FIG. 5 panel (B) shows MS/MS spectrum of serine (concentration: 100 ppb, volume: 10 µl, solvent: MeOH/H$_2$O/HOAc (50:49:1, v/v/v)). Peak 74 and 83 also exist in the blank spectrum with solvent and without serine. FIG. 21 panel (A) shows MS spectrum of serine (m/z, 106) using probes of the invention. Panel (A) also shows MS/MS spectrum of serine (m/z, 106).

FIG. 21 Panel (B) shows MS spectrum of methadone (m/z, 310) using probes of the invention. Panel (B) also shows MS/MS spectrum of methadone (m/z, 310). Panel (C) shows MS spectrum of roxithromycin (m/z, 837) using probes of the invention. Panel (B) also shows MS/MS spectrum of roxithromycin (m/z, 837).

Figure 6A:
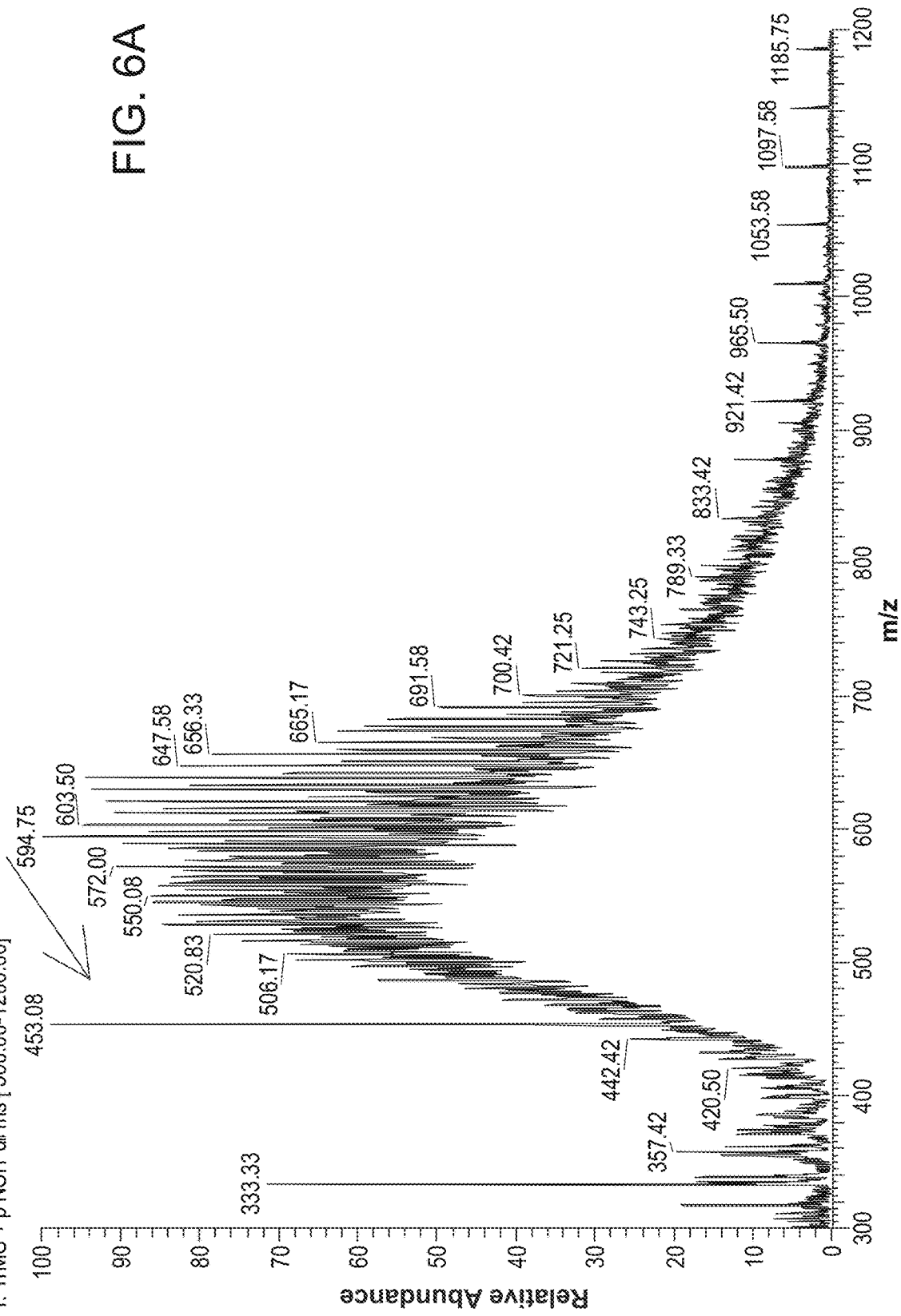
FIG. 6 panel (A) is a MS spectrum of peptide bradykinin 2-9 (concentration: 10 ppm, volume: 10 μl, solvent: MeOH/H$_2$O/HOAc (50:49:1, v/v/v)) using probes of the invention.
Figure 6B:
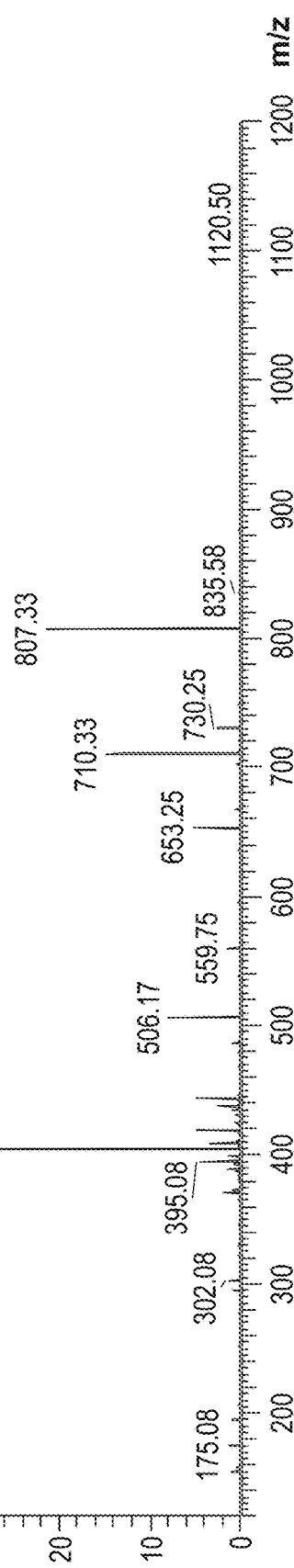

FIG. 6 panel (A) shows MS spectrum of peptide bradykinin 2-9 (concentration: 10 ppm, volume: 10 µl, solvent: MeOH/H$_2$O/HOAc (50:49:1, v/v/v)) using probes of the invention. FIG. 6 panel (B) shows MS/MS spectrum of bradykinin 2-9 (concentration: 1 ppm, volume: 10 µl, solvent: MeOH/H$_2$O/HOAc (50:49:1, v/v/v)). The hump in the spectrum is assumed to be caused by polymers, such as polyethylene glycol (PEG), which are frequently added to materials in industry. FIG. 21 panel (D) shows MS spectrum of bradykinin 2-9 (m/z, 453) using probes of the invention. Panel (D) also shows MS/MS spectrum of bradykinin 2-9 (m/z, 453). Panel D further shows adduct ions [M+H] (m/z, 904), [M+2H]$^{2+}$ (m/z, 453), [M+H+Na]$^{2+}$ (m/z, 464) and [M+2Na]$^{2+}$ (m/z, 475). The m/z 453 peak was double charged adduct ion confirmed by the MS/MS spectrum.

Figure 11A:
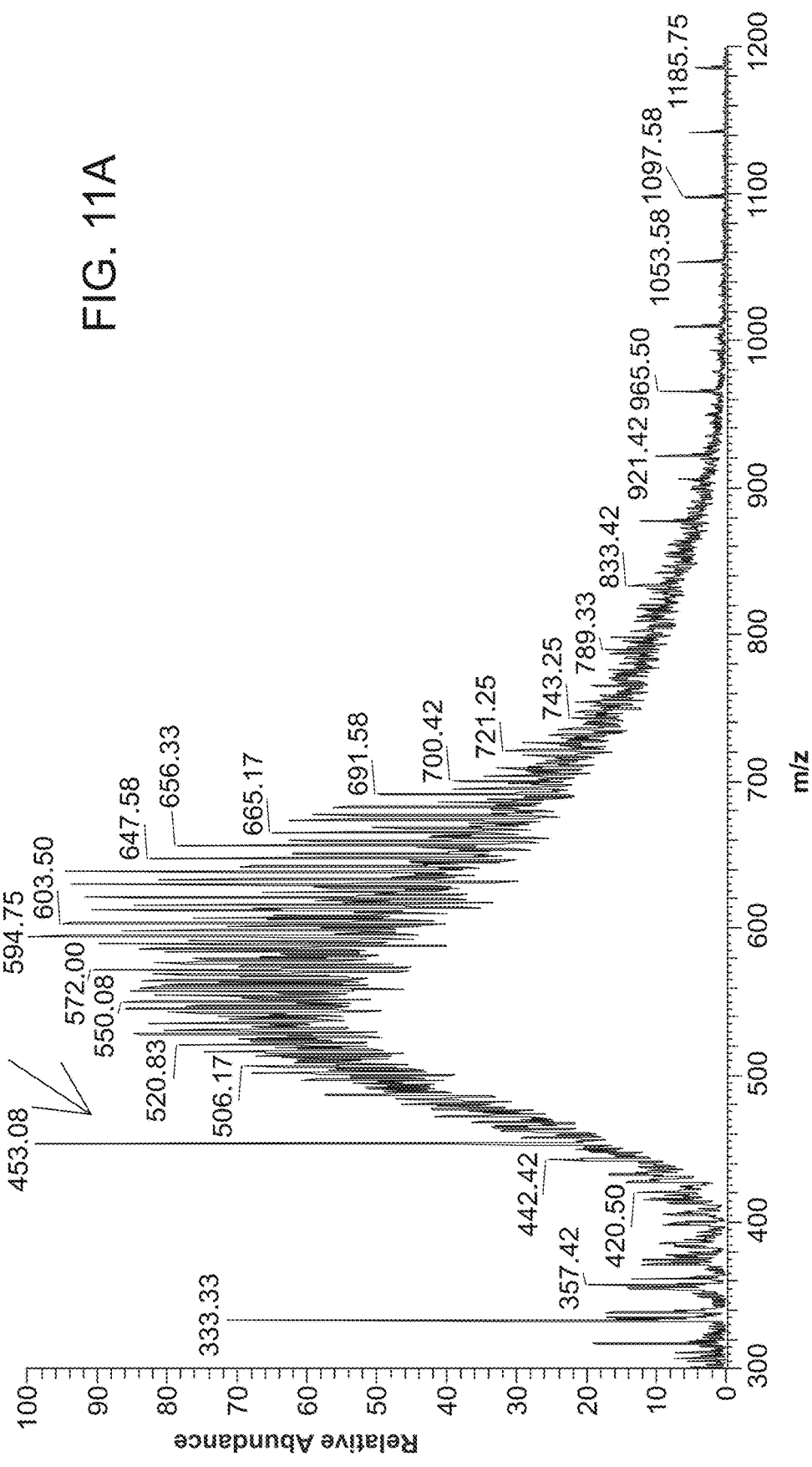
FIG. 11 are MS spectra showing the difference between peptide analysis (10 ppm of bradykinin 2-9) on (A) paper triangle and (B) PVDF membrane using the same parameters (~2 kV, Solvent: MeOH:H$_2$O=1:1).
Figure 11B:
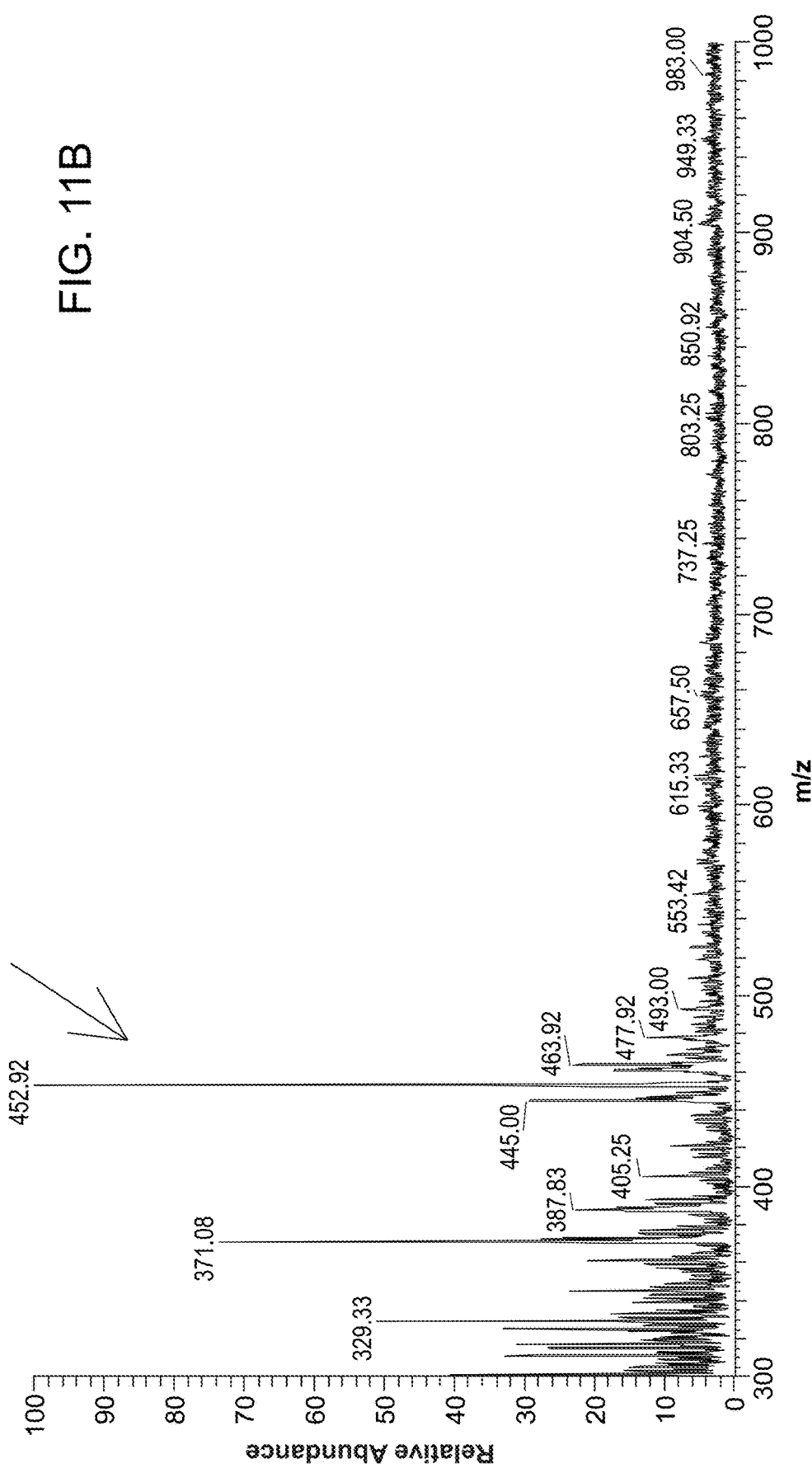
Figure 12A:
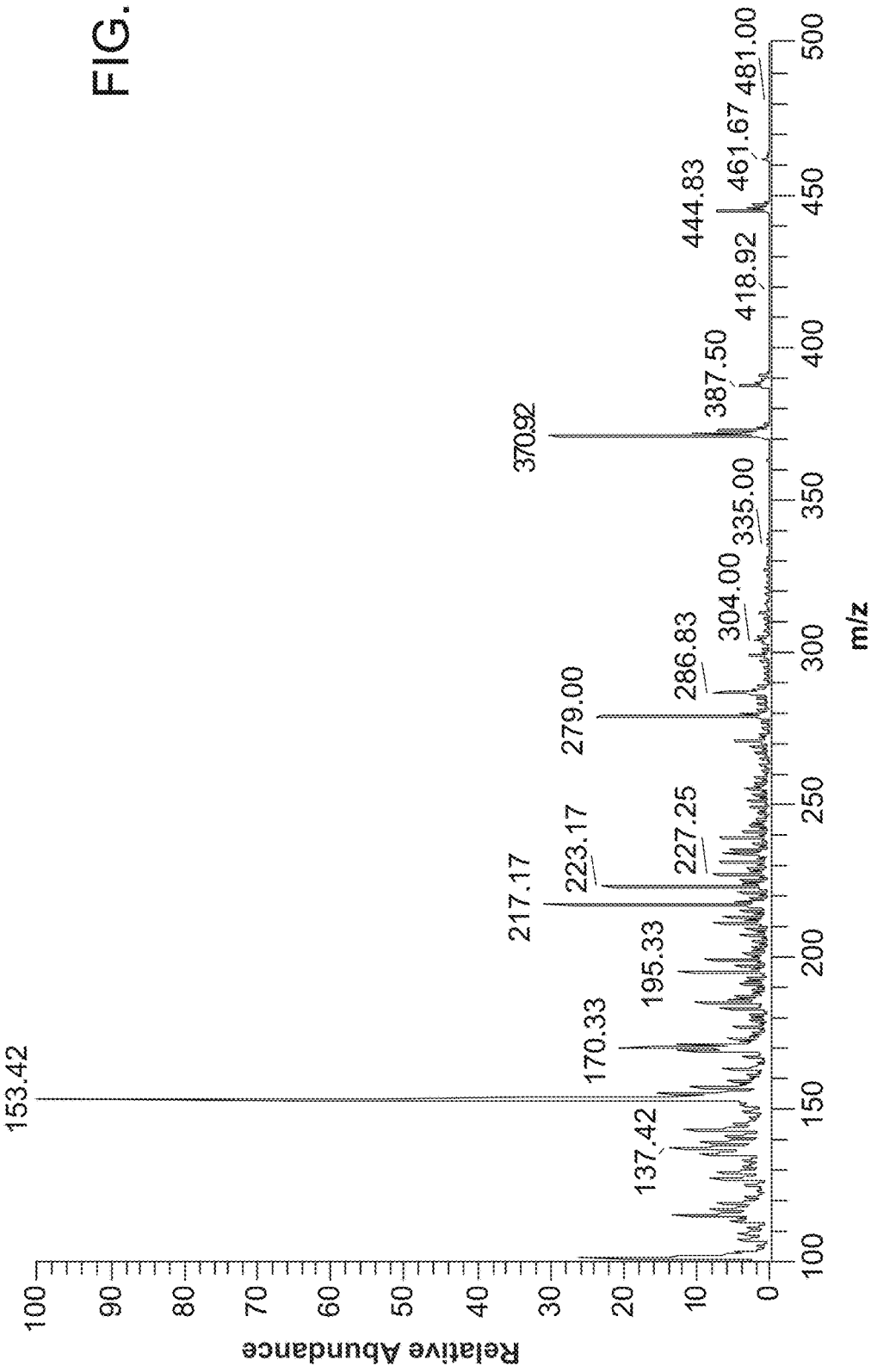
FIG. 12 shows direct MS spectra of plant tissues using sliced tissues of four kinds of plants. (A) Onion, (B) Spring onion, and two different leaves (C) and (D).
Figure 12B:
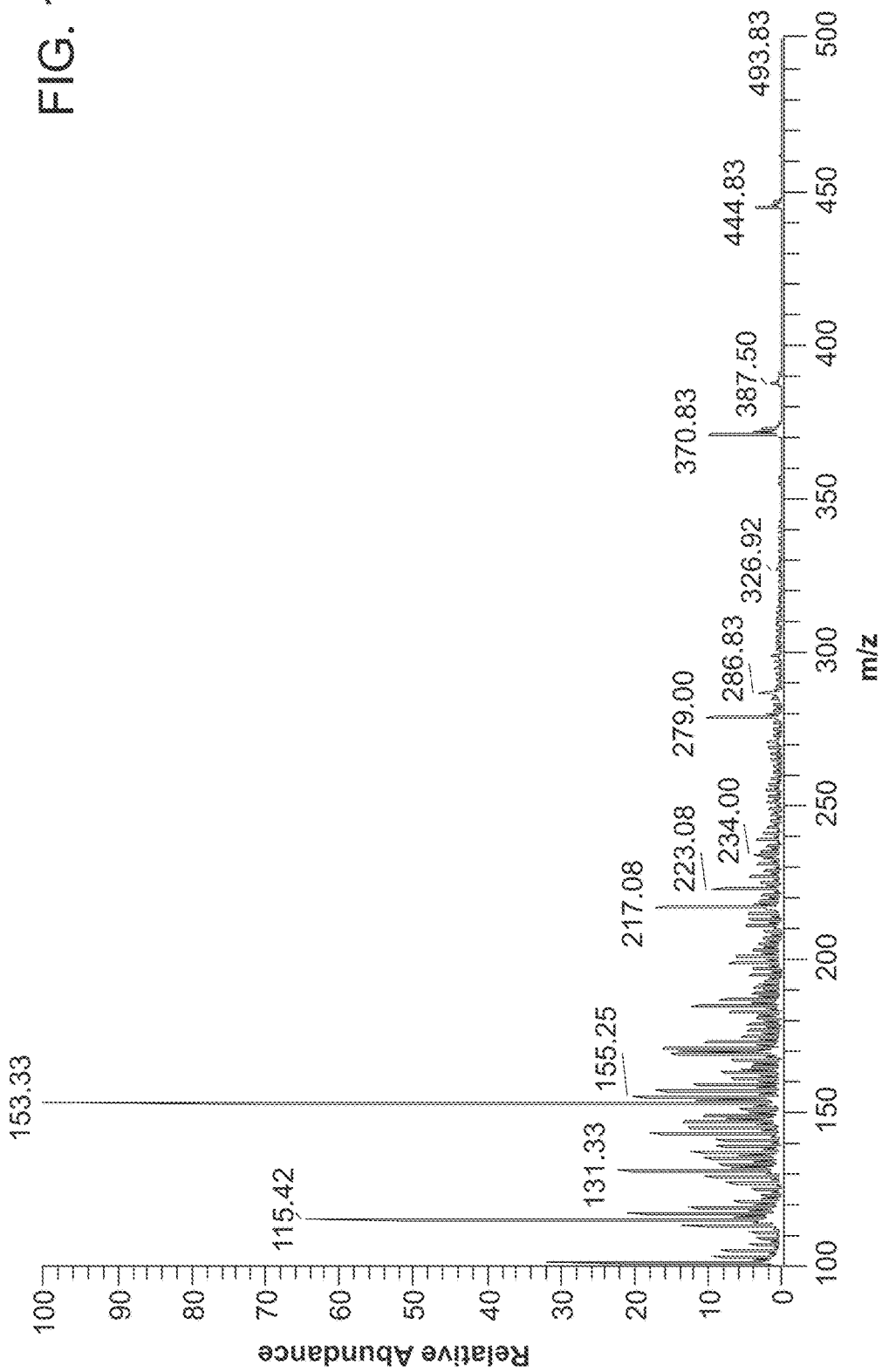
Figure 12C:
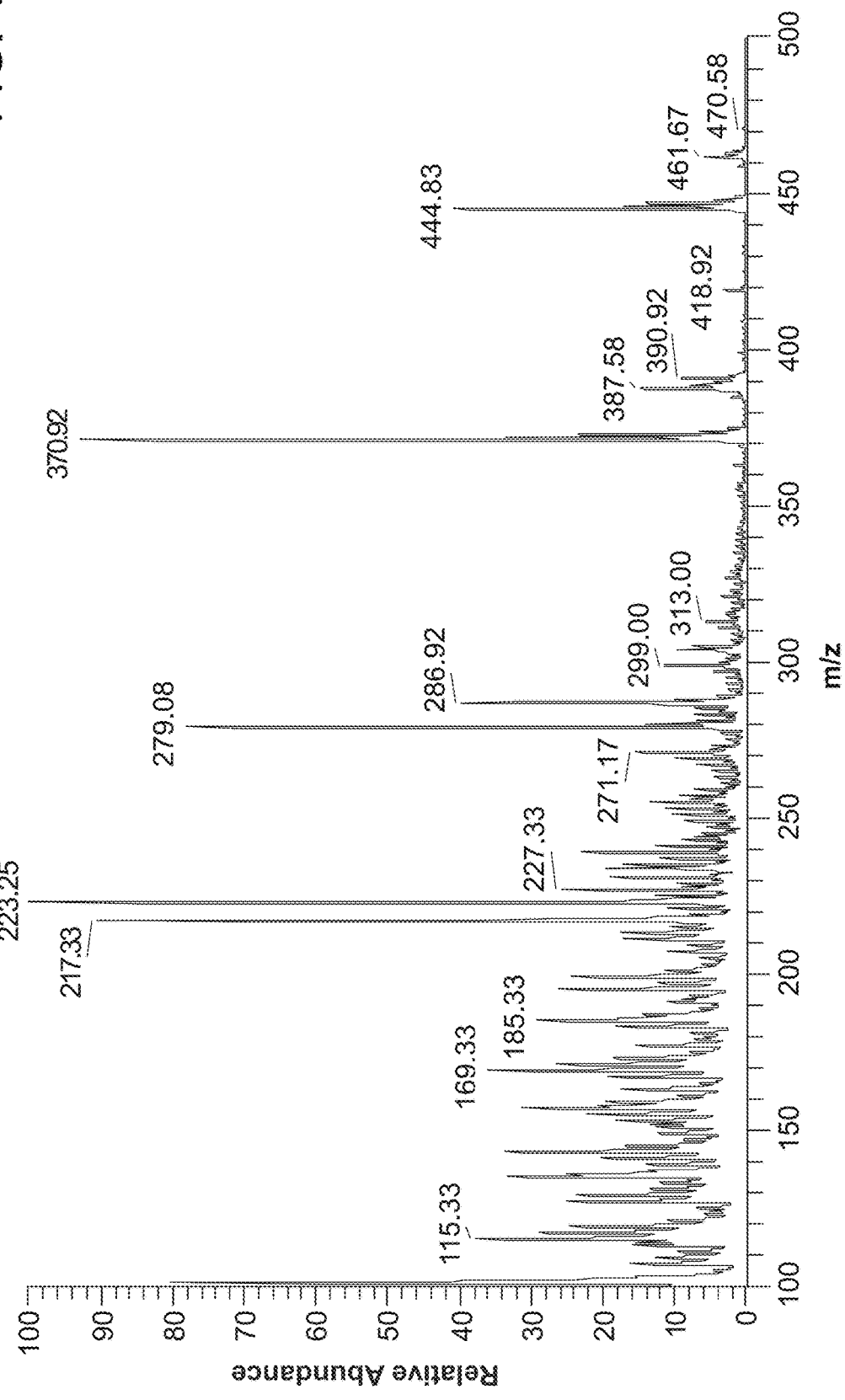
Figure 12D:
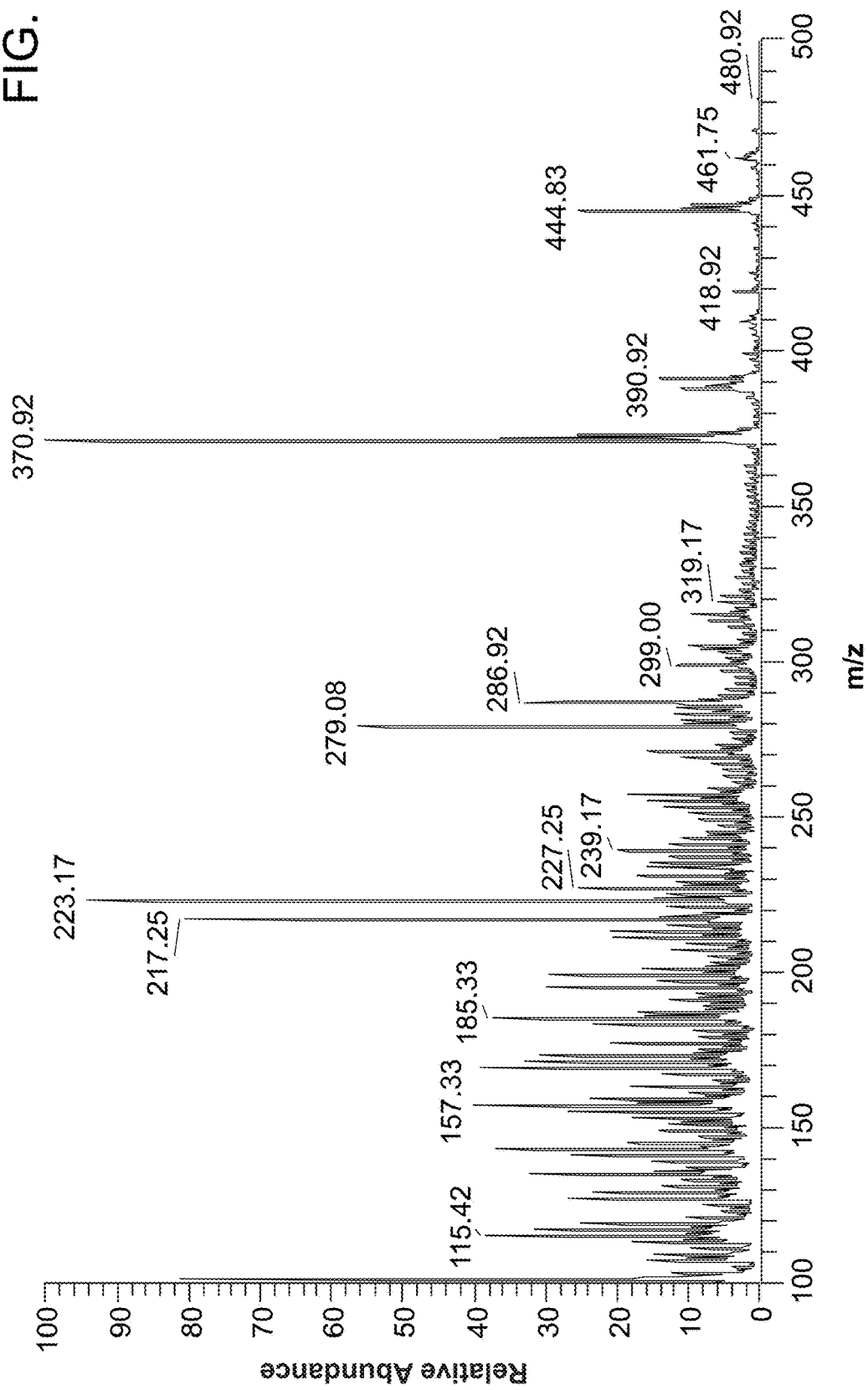

FIG. 11 is an MS spectra showing the difference between peptide analysis (10 ppm of bradykinin 2-9) on (A) paper slice and (B) PVDF membrane using the same parameters (~2 kV, Solvent: MeOH:H$_2$O=1:1).

Data herein show that probes of the invention work well over the mass/charge range from 50 to over 1000 for detection of pure compounds. Data further shows that detection was achieved down to as low as 1 ng/mL for most chemicals, including illegal drugs, such as heroin, cocaine and methadone.

Example 7: Complex Mixtures

Complex mixtures such as urine, blood, and cola drink were examined using methods, devices, and systems of the invention. All experiments were carried out with a Finnigan LTQ mass spectrometer (Thermo Electron, San Jose, Calif.).

Figure 7A:
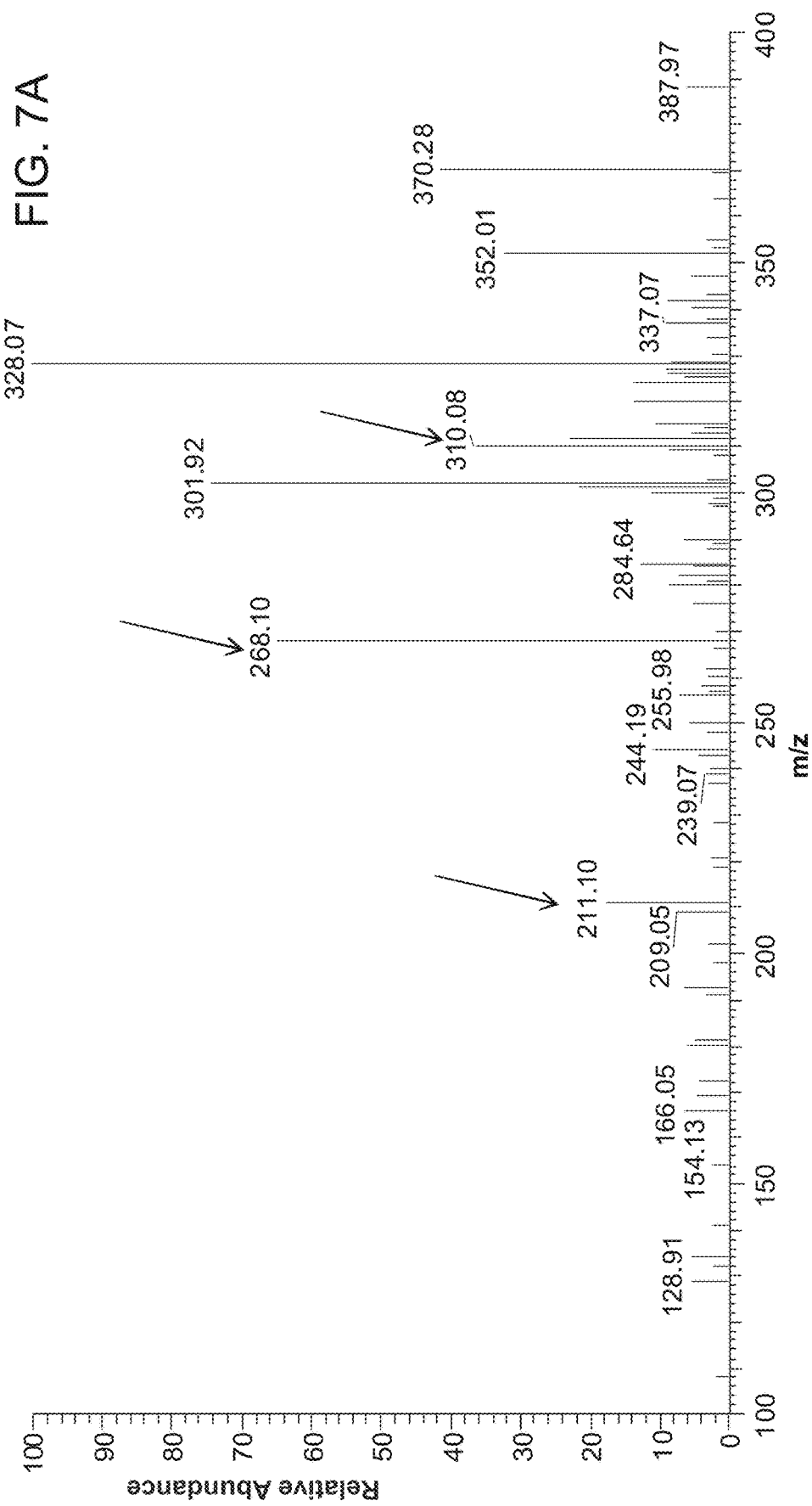
FIG. 7 panel (A) is a MS/MS spectrum showing that heroin can be detected from whole blood sample by a "spot" method.

FIG. 7 panel (A) shows an MS/MS spectrum that shows that heroin was detected from whole blood sample by a "spot" method. 0.4 µl of whole blood sample containing 200 ppb heroin was applied on the center of the triangle paper to form a 1 mm$^2$ blood spot. After the spot was dry, 10 µl of solvent (MeOH/H$_2$O/HOAc (50:49:1, v/v/v)) was applied to the rear end of the triangle paper. Due to the capillary effect, the solvent moved forward and dissolved the chemicals in the blood spot. Finally, electrospray occurred when the solvent reached the tip of the paper. To demonstrate the effectiveness of the "blood spot" method mentioned above, the whole blood was added on the paper for electrospray directly. MS/MS spectrum showed that heroin was not detected from 10 µl of whole blood sample, even when the concentration was as high as 20 ppm (FIG. 7 panel B).

Figure 8A:
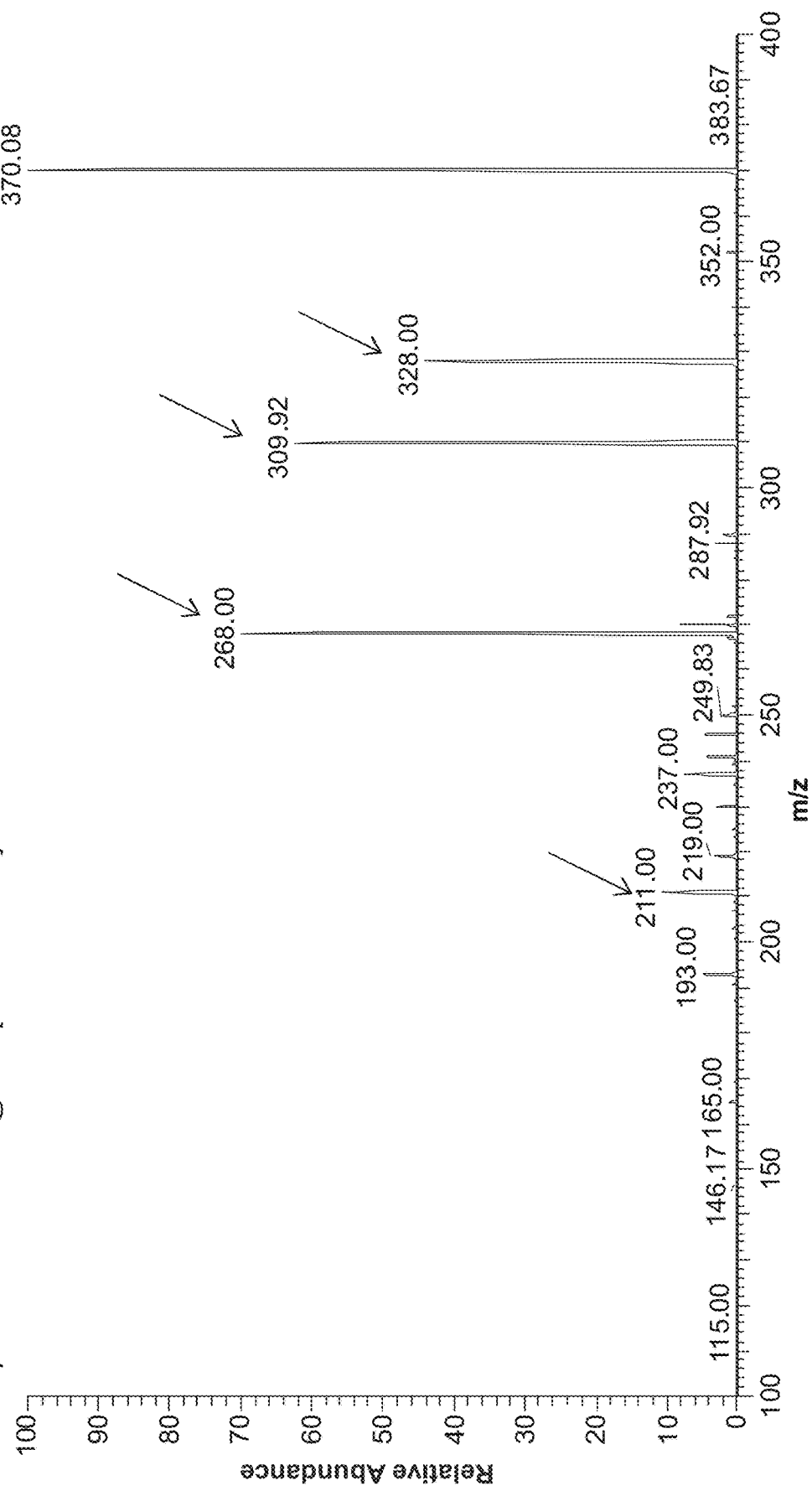
FIG. 8 panel (A) MS/MS spectrum shows heroin can be detected from raw urine sample by a "spot" method.
Figure 8B:
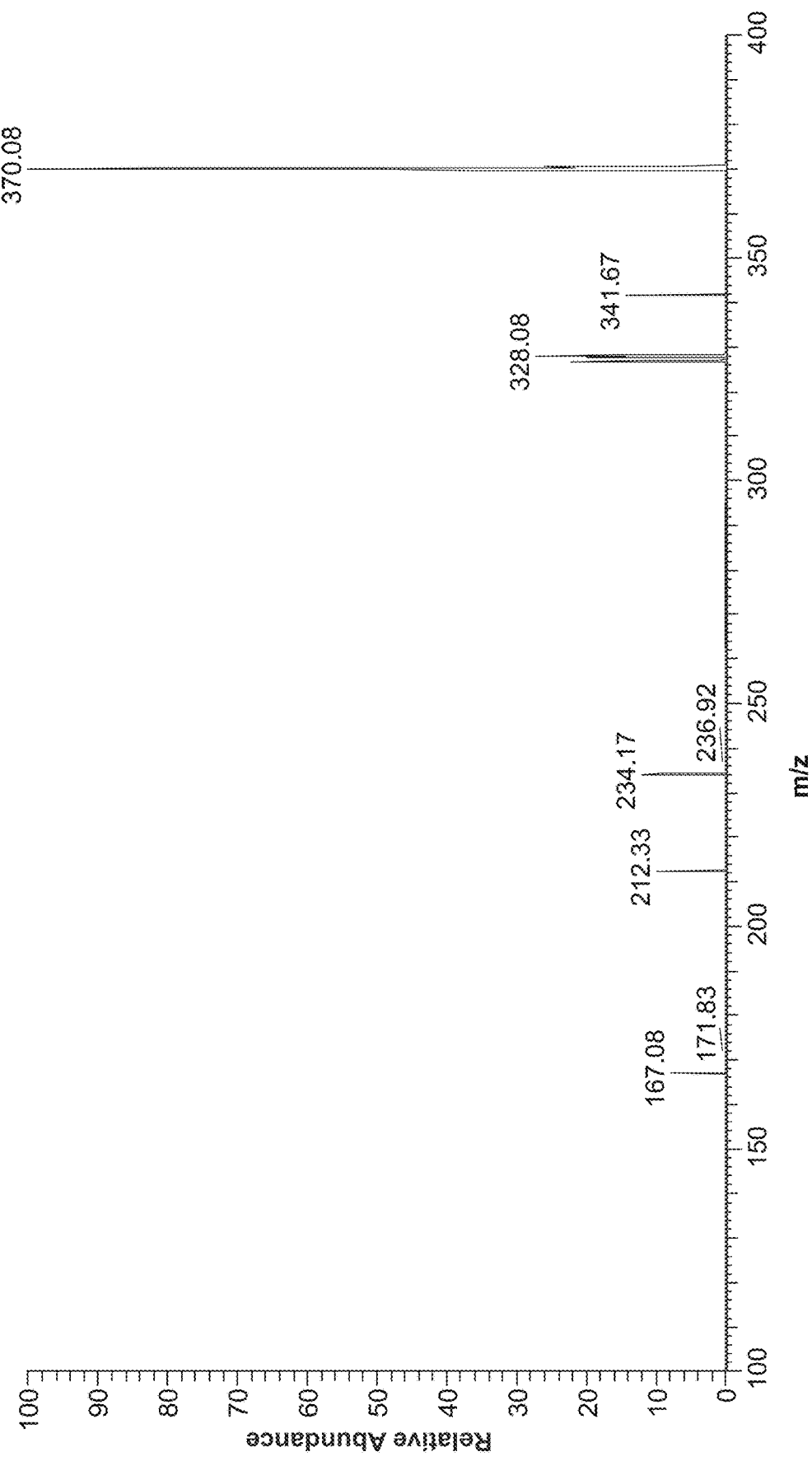

FIG. 8 panel (A) shows an MS/MS spectrum that shows that heroin can be detected from raw urine sample by a "spot" method. 0.4 µl of raw urine sample containing 100 ppb heroin was applied on the center of the triangle paper to form a 1 mm$^2$ urine spot. After the spot was dry, 10 µl of solvent (MeOH/H$_2$O/HOAc (50:49:1, v/v/v)) was applied to the rear end of the triangle paper. Due to the capillary effect, the solvent moved forward and dissolved the chemicals in the blood spot. Finally, electrospray occurred when the solvent reached the tip of the paper. To demonstrate the effectiveness of the "spot" method mentioned above, the raw urine was added on the paper for electrospray directly. MS/MS spectrum showed heroin was not detected from 10 µl of raw urine sample when concentration was 100 ppb (FIG. 8 panel B).

Figure 9A:
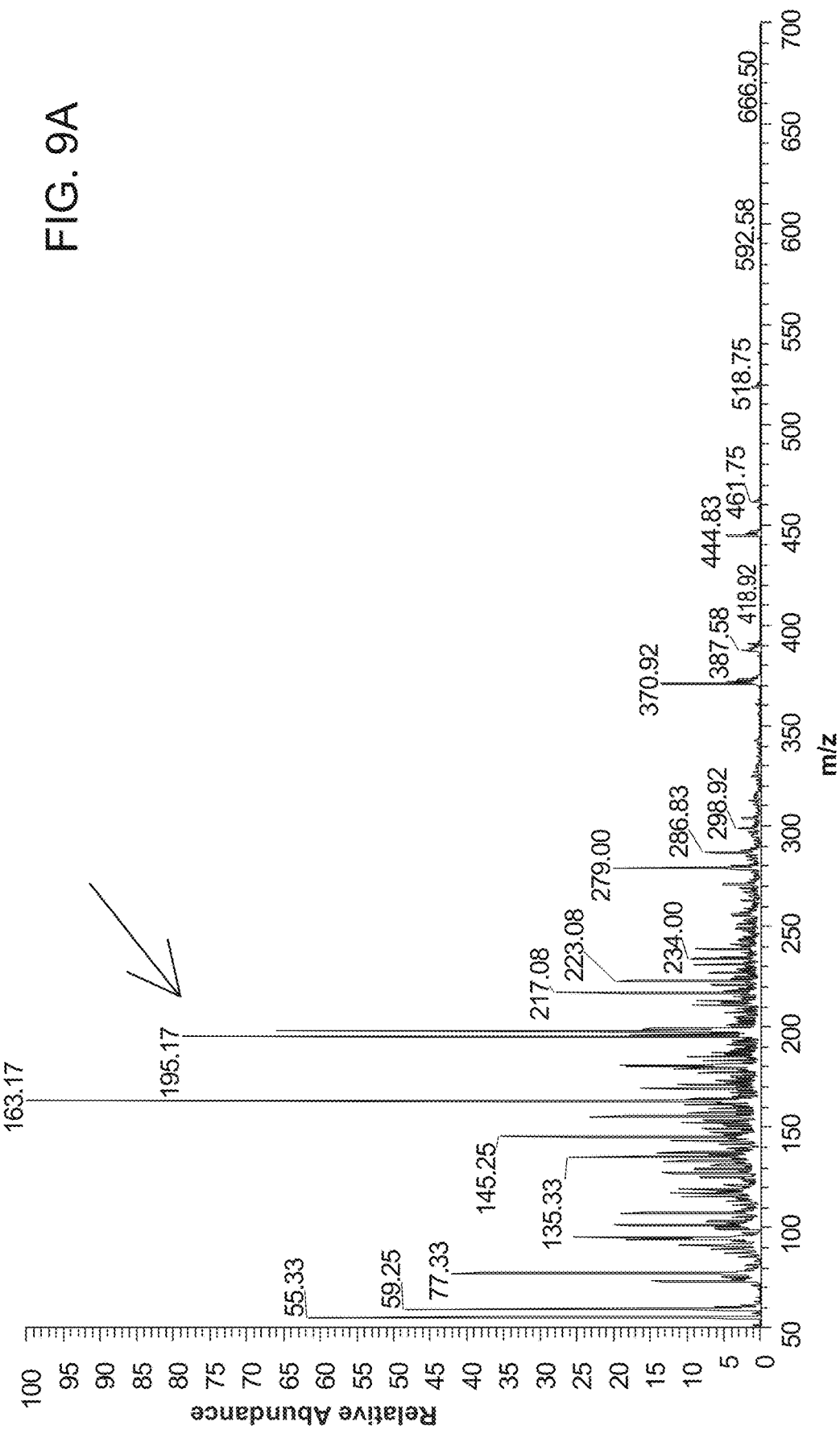
FIG. 9 panel (A) is a MS spectrum showing the caffeine detected from a cola drink without sample preparation.
Figure 9B:
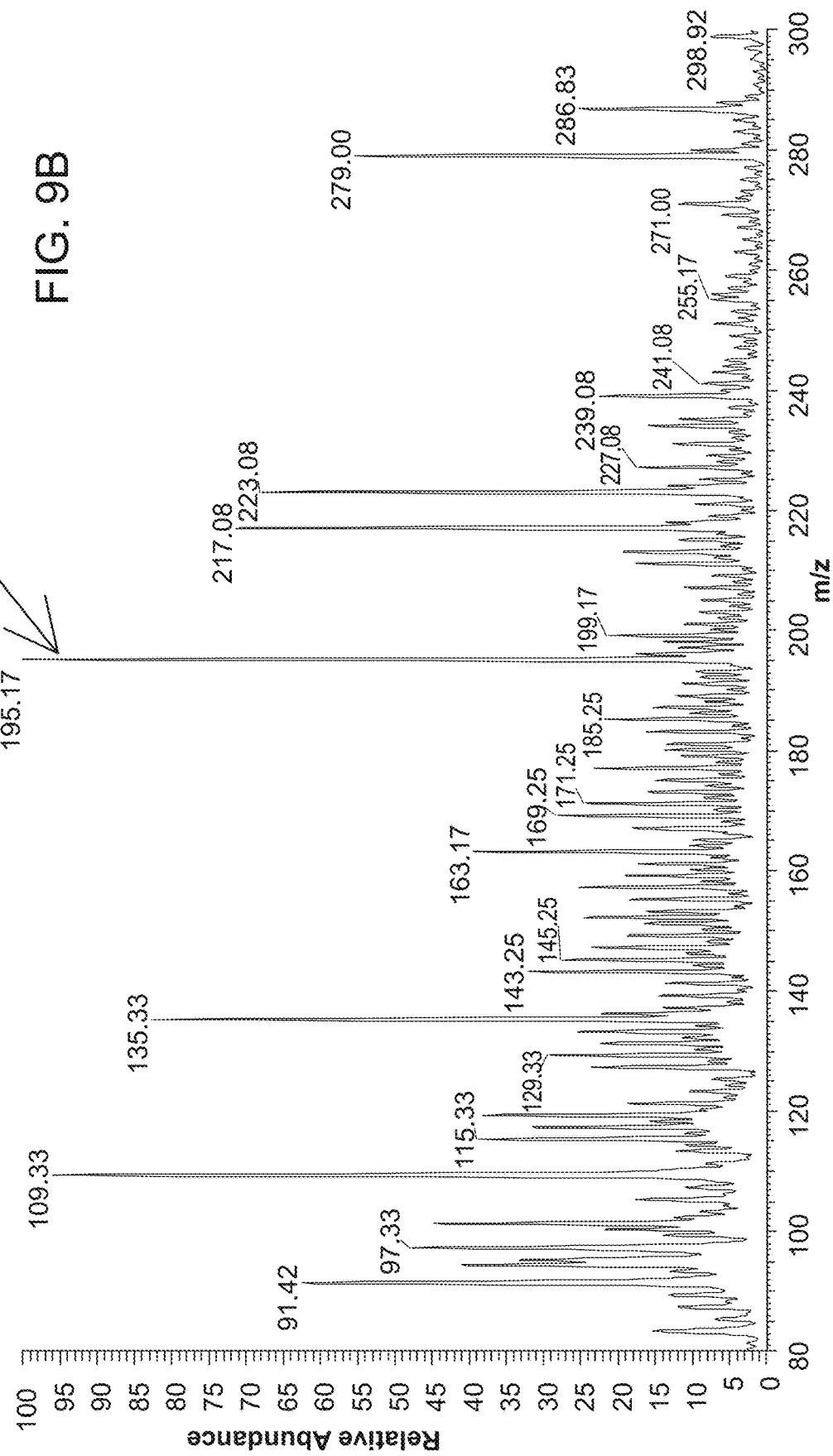

FIG. 9 panel (A) is an MS spectrum showing that caffeine was detected from a cola drink without sample preparation. FIG. 9 panel (B) is an MS spectrum showing that caffeine was detected from coffee powder. A paper triangle was used to collect the coffee powder from a coffee bag by swabbing the surface.

FIG. 22 panels (A-B) show the spectra of COCA-COLA (cola drink), analyzed in positive mode and negative mode, respectively. The peak of protonated caffeine, m/z 195, identified in MS/MS spectrum, was dominated in the mass spectrum in positive mode due to the high concentration of caffeine (100 ug/mL) in this drink (Panel C). Two high concentrated compounds, potassium benzoate and acesulfame potassium were identified in the MS/MS spectrum in negative mode (Panels D-E).

FIG. 22 panel F shows spectra of caffeine in urine from a person who had drunk COCA-COLA (cola drink) two hours before the urine collection. Urine typically contains urea in very high concentration, which is also easily ionized. Therefore, protonated urea [m/z, 61] and urea dimmer [m/z, 121] dominated the MS spectrum. However, the protonated caffeine was identified in the MS/MS spectrum, which showed good signal to noise ratio in the urine sample.

Figure 10B:
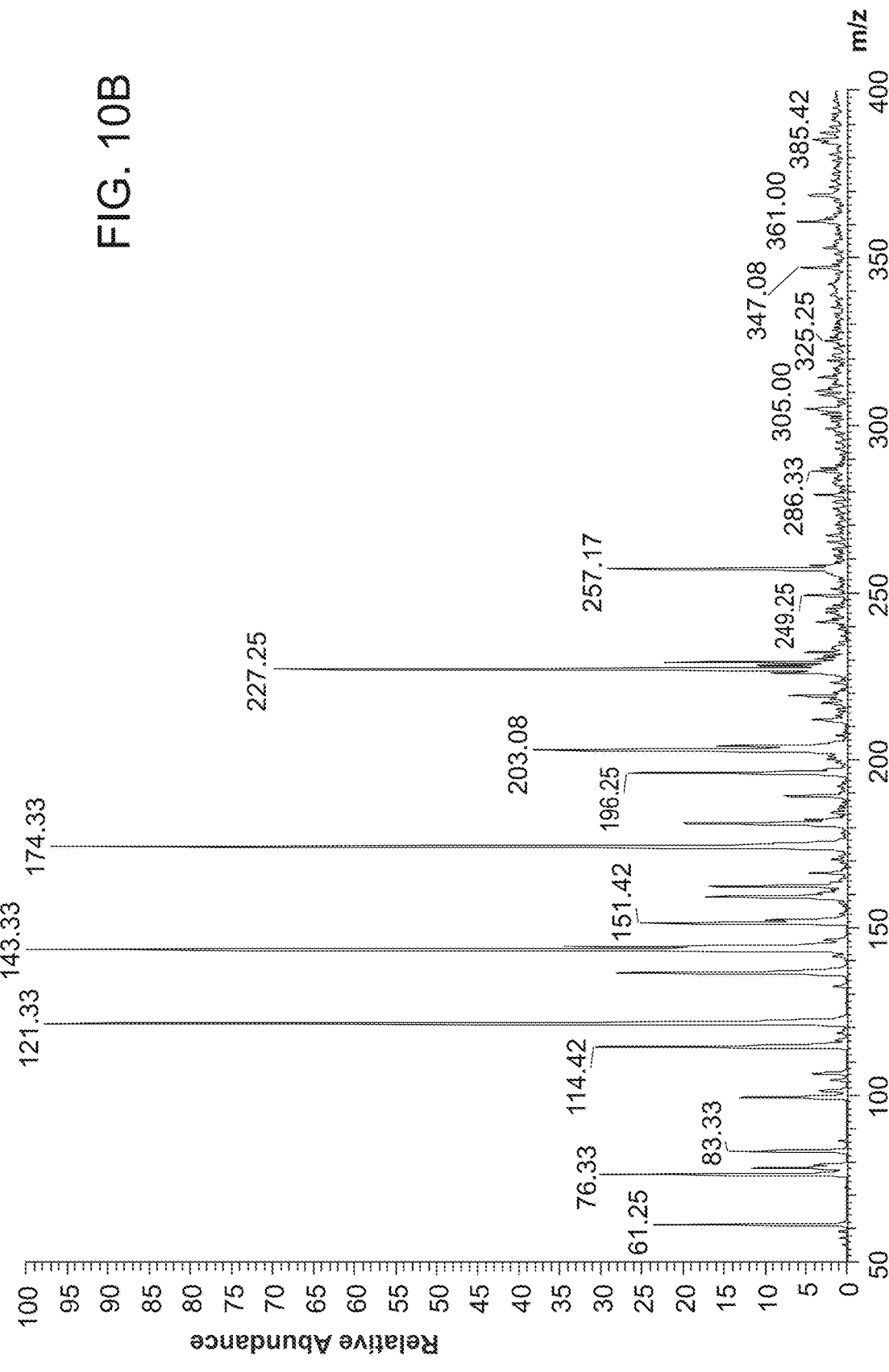
FIG. 10 shows MS spectra of urine analysis without sample preparation.

FIG. 10 shows MS spectra of urine taken for analysis without sample preparation. FIG. 10 panel (A) is a mass spectra of caffeine that was detected in urine from a person who had consumed coffee. FIG. 10 panel (B) is a mass spectra showing that caffeine was not detected in urine from a person who had not consumed any coffee.

FIG. 22 panel G shows the MS spectrum of heroin (m/z, 370) collected as a swabbed sample. A 5 uL solution containing 50 ng heroin was spotted on a 1 cm$^2$ area of a desktop. The paper triangle was wetted and used to swab the surface of the desktop. The paper triangle was then connected to the high voltage source for mass detection. This data shows that probes of the invention can have dual roles of ionization source as well as a sampling device for mass detection. Trace sample on solid surface could be simply collected by swabbing the surface using probes of the invention. Dust and other interferences were also collected on the paper triangle, but the heroin could be directly detected from this complex matrix.

Example 8: Plant Tissue Direct Analysis by ESI without Extraction

FIG. 12 shows direct MS spectra of plant tissues using sliced tissues of four kinds of plants. (A) Onion, (B) Spring onion, and two different leaves (C) and (D).

Figure 13A:
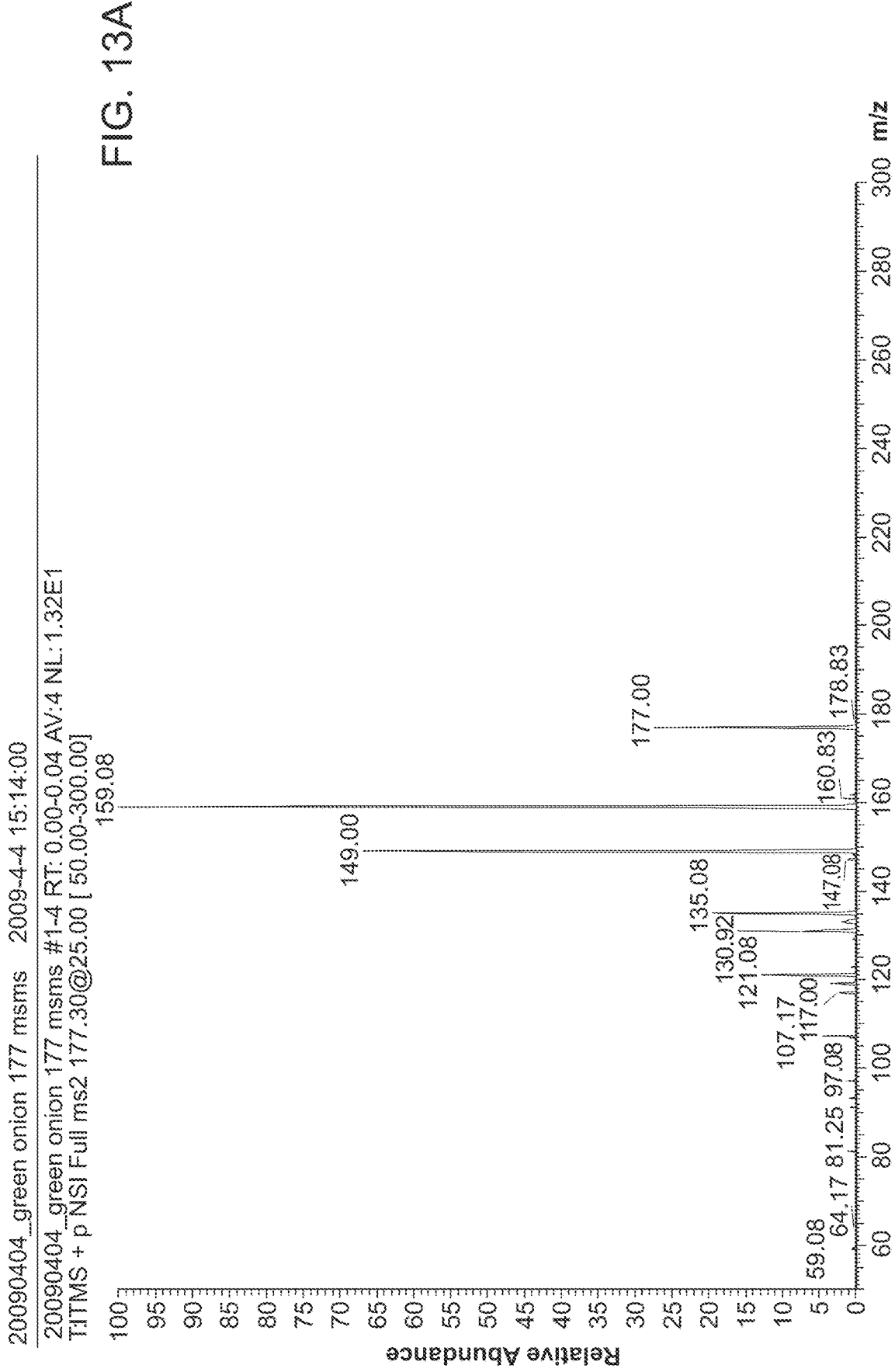
FIG. 13 shows MS/MS spectra of Vitamin C.
Figure 13B:
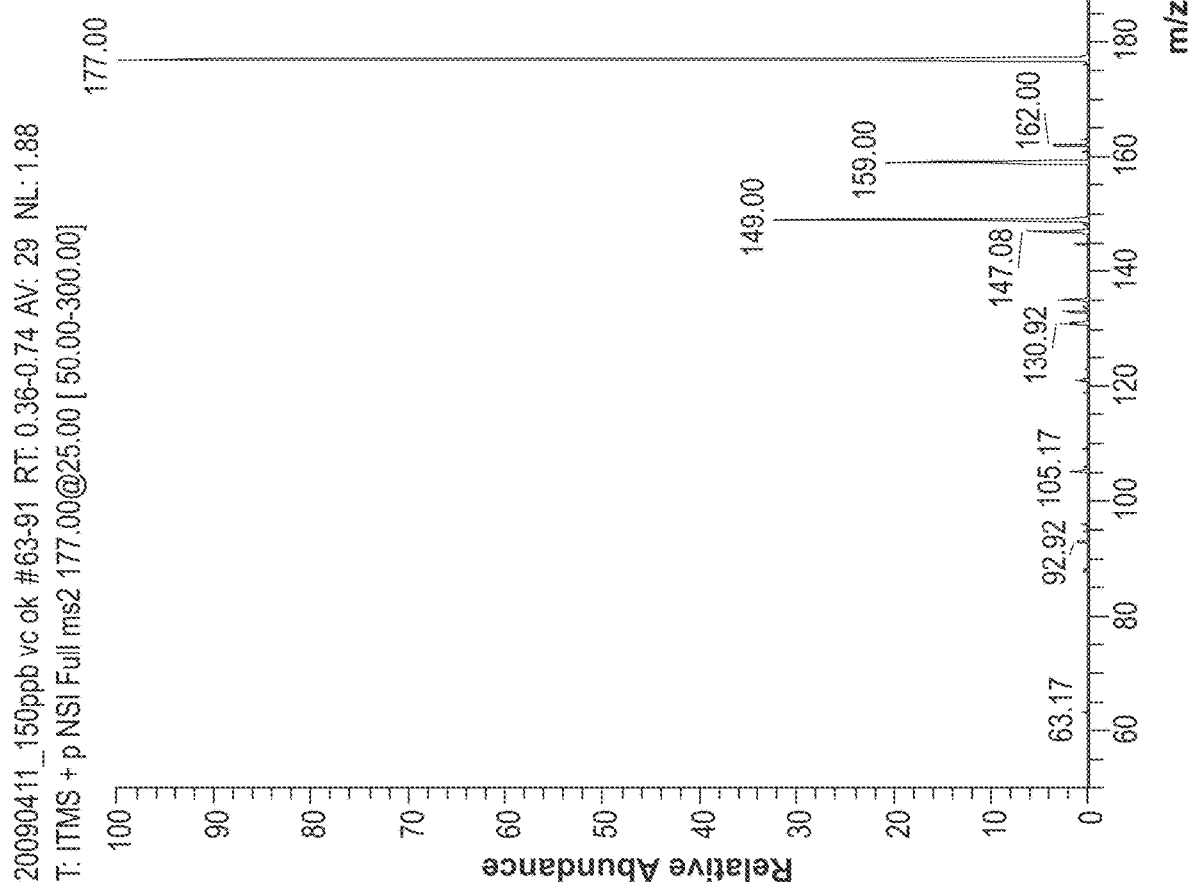

FIG. 13 shows an MS/MS spectra of Vitamin C analysis (A) direct analysis of onion without sample preparation, (B) using standard solution.

Example 9: Whole Blood and Other Biofluids

Body fluids, such as plasma, lymph, tears, saliva, and urine, are complex mixtures containing molecules with a wide range of molecular weights, polarities, chemical properties, and concentrations. Monitoring particular chemical components of body fluids is important in a number of different areas, including clinical diagnosis, drug development, forensic toxicology, drugs of abuse detection, and therapeutic drug monitoring. Tests of blood, including the derived fluids plasma and serum, as well as on urine are particularly important in clinical monitoring.

A wide variety of chemicals from blood are routinely monitored in a clinical setting. Common examples include a basic metabolic panel measuring electrolytes like sodium and potassium along with urea, glucose, and creatine and a lipid panel for identifying individuals at risk for cardiovascular disease that includes measurements of total cholesterol, high density lipoprotein (HDL), low density lipoprotein (LDL), and triglycerides. Most laboratory tests for chemicals in blood are actually carried out on serum, which is the liquid component of blood separated from blood cells using centrifugation. This step is necessary because many medical diagnostic tests rely on colorimetric assays and therefore require optically clear fluids. After centrifugation, detection of the molecule of interest is carried in a number of ways, most commonly by an immunoassay, such as an enzyme-linked immunosorbent assay (ELISA) or radioimmunoassay (RIA), or an enzyme assay in which the oxidation of the molecule of interest by a selective enzyme is coupled to a reaction with a color change, such as the tests for cholesterol (oxidation by cholesterol oxidase) or glucose (oxidation by glucose oxidase).

There is considerable interest in the pharmaceutical sciences in the storage and transportation of samples of whole blood as dried blood spots on paper (N. Spooner et al. *Anal Chem.*, 2009, 81, 1557). Most tests for chemicals found in blood are carried out on a liquid sample, typically serum or plasma isolated from the liquid whole blood. The required storage, transportation, and handling of liquid blood or blood components present some challenges. While blood in liquid form is essential for some tests, others can be performed on blood or other body fluids that have been spotted onto a surface (typically paper) and allowed to dry.

Figure 23A:
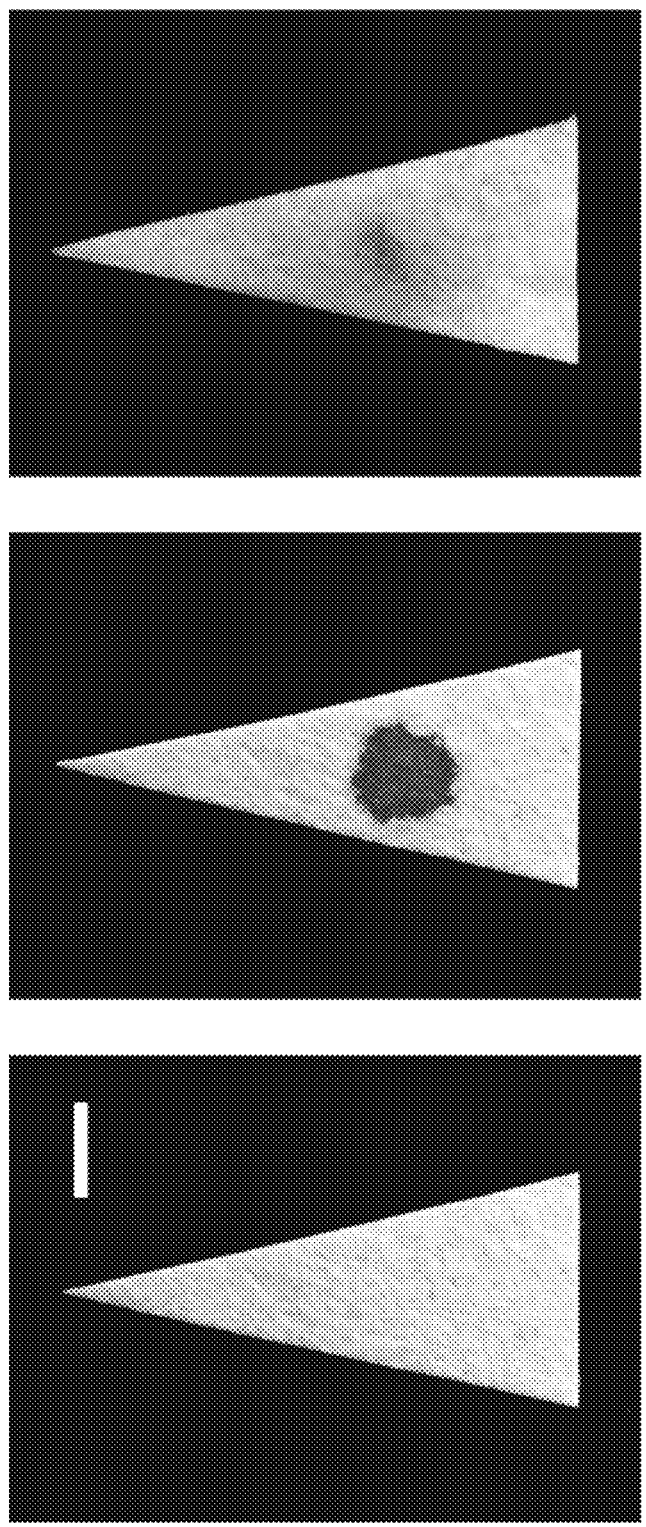
FIG. 23 panel (A) shows images of a probe of the invention used for blood analysis. In this embodiment, the porous material is paper. The panel on the left is prior to spotting with whole blood. The panel in the middle is after spotting with whole blood and allowing the spot to dry. The panel on the right is after methanol was added to the paper and allowed to travel through the paper. The panel on the right shows that the methanol interacts with the blood spot, causing analytes to travel to the tip of the paper for ionization and analysis. Panel (B) is a mass spectrum of Atenolol from whole blood. Panel (C) is a mass spectrum of heroin from whole blood.
Figure 23B:
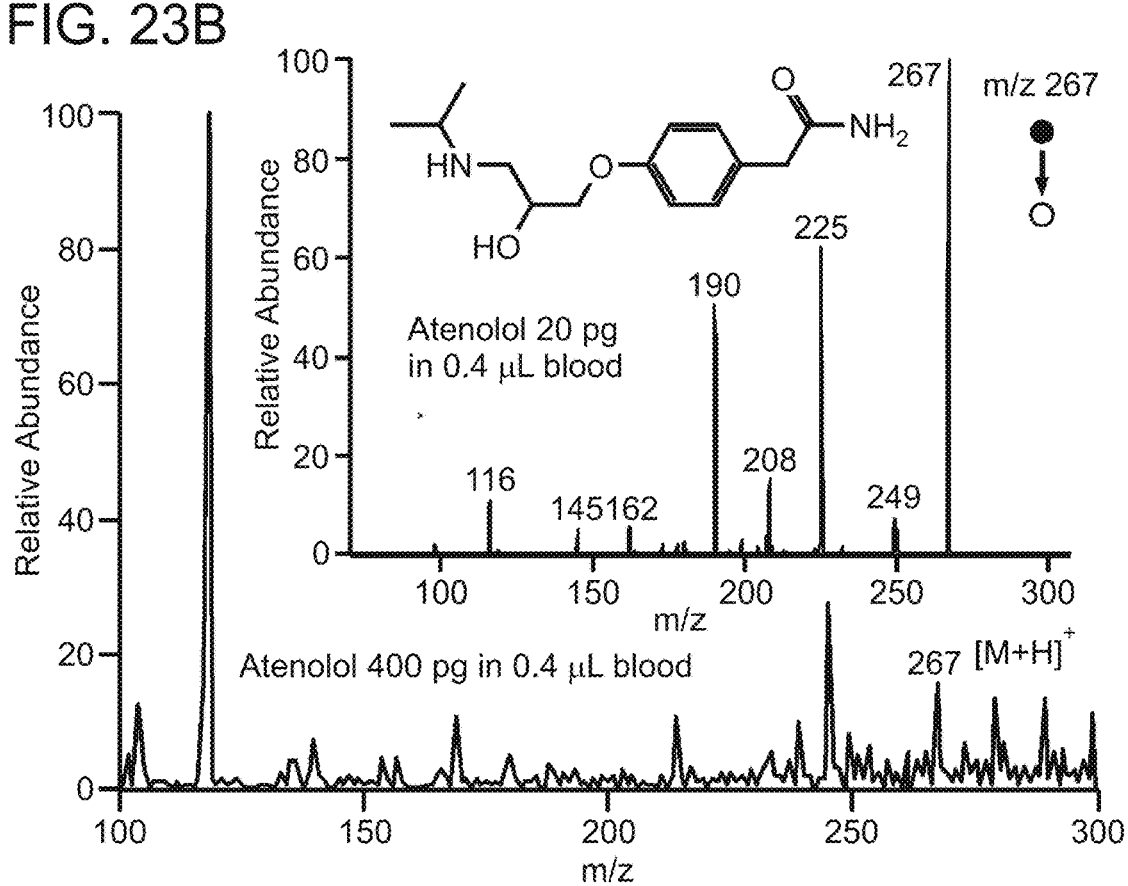
Figure 23C:
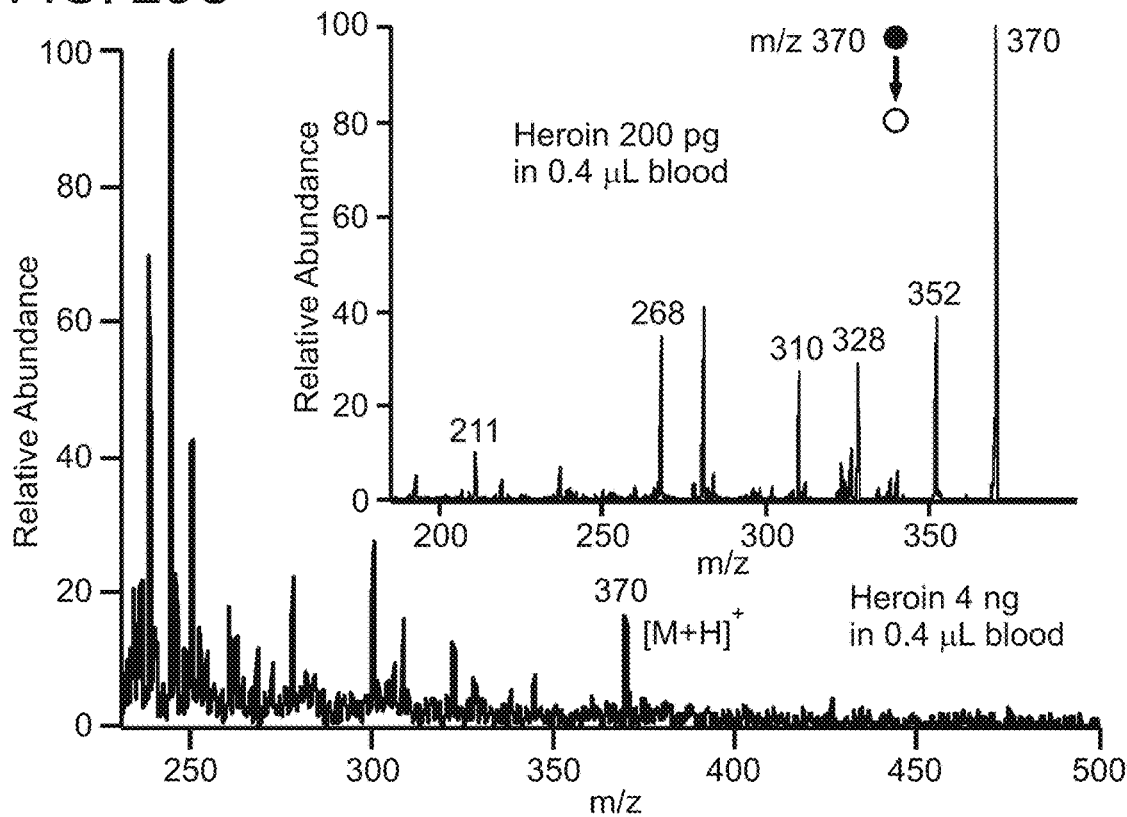

Probes and methods of the invention can analyze whole blood without the need for any sample preparation. The sample was prepared as follows. 0.4 uL blood was directly applied on the center of paper triangle and left to dry for about 1 min. to form a dried blood spot (FIG. 23 panel A). 10 uL methanol/water (1:1, v/v) was applied near the rear end of the paper triangle. Driven by capillary action, the solution traveled across the paper wetting it throughout its depth. As the solution interacted with the dried blood spot, the analytes from the blood entered the solution and were transported to the tip of the probe for ionization (FIG. 23 panel A). The process of blood sample analysis was accomplished in about 2 min.

Different drugs were spiked into whole blood and the blood was applied to probes of the invention as described above. Detection of different drugs is described below.

Figure 14A:
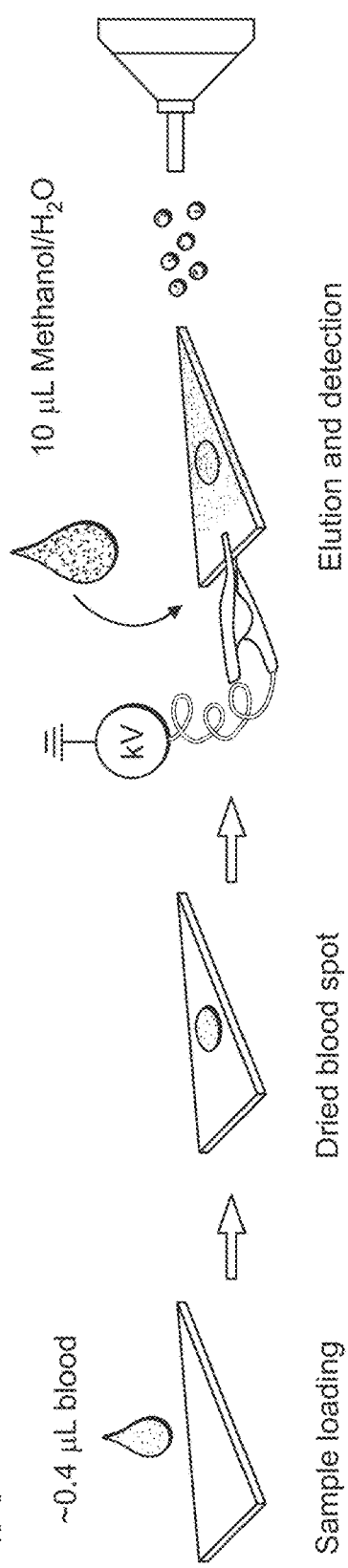
FIG. 14 panel A is a picture showing dried blood spot analysis on paper; 0.4 μL of whole blood is applied directly to a triangular section of chromatography paper (typically height 10 mm, base 5 mm). A copper clip holds the paper section in front of the inlet of an LTQ mass spectrometer (Thermo Fisher Scientific, San Jose, Calif.) and a DC voltage (4.5 kV) is applied to the paper wetted with 10 μL methanol/water (1:1 v/v). Panel B shows the molecular structure of imatinib (GLEEVEC) and paper spray tandem mass spectrum of 0.4 μL whole blood containing 4 μg/mL imatinib. Imatinib is identified and quantified (inset) by the MS/MS transition m/z 494→m/z 394 (inset). Panel C shows a quantitative analysis of whole blood spiked with imatinib (62.5-4 μg/mL) and its isotopomers imatinib-d8 (1 μg/mL). Inset plot shows low concentration range.
Figure 14B:
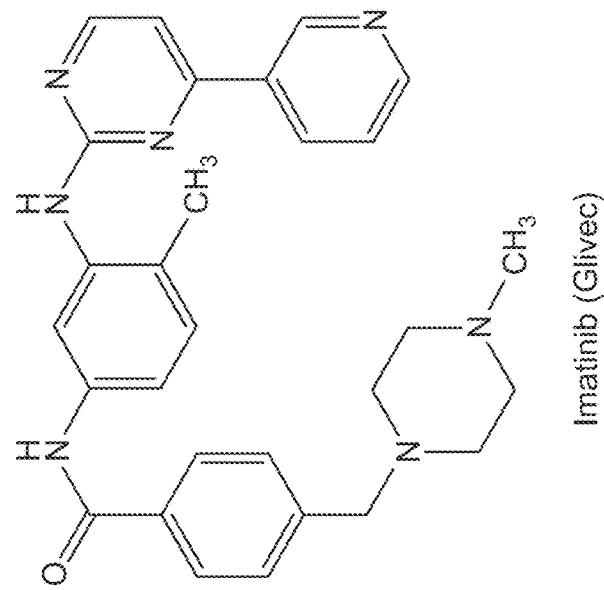
Figure 14C:
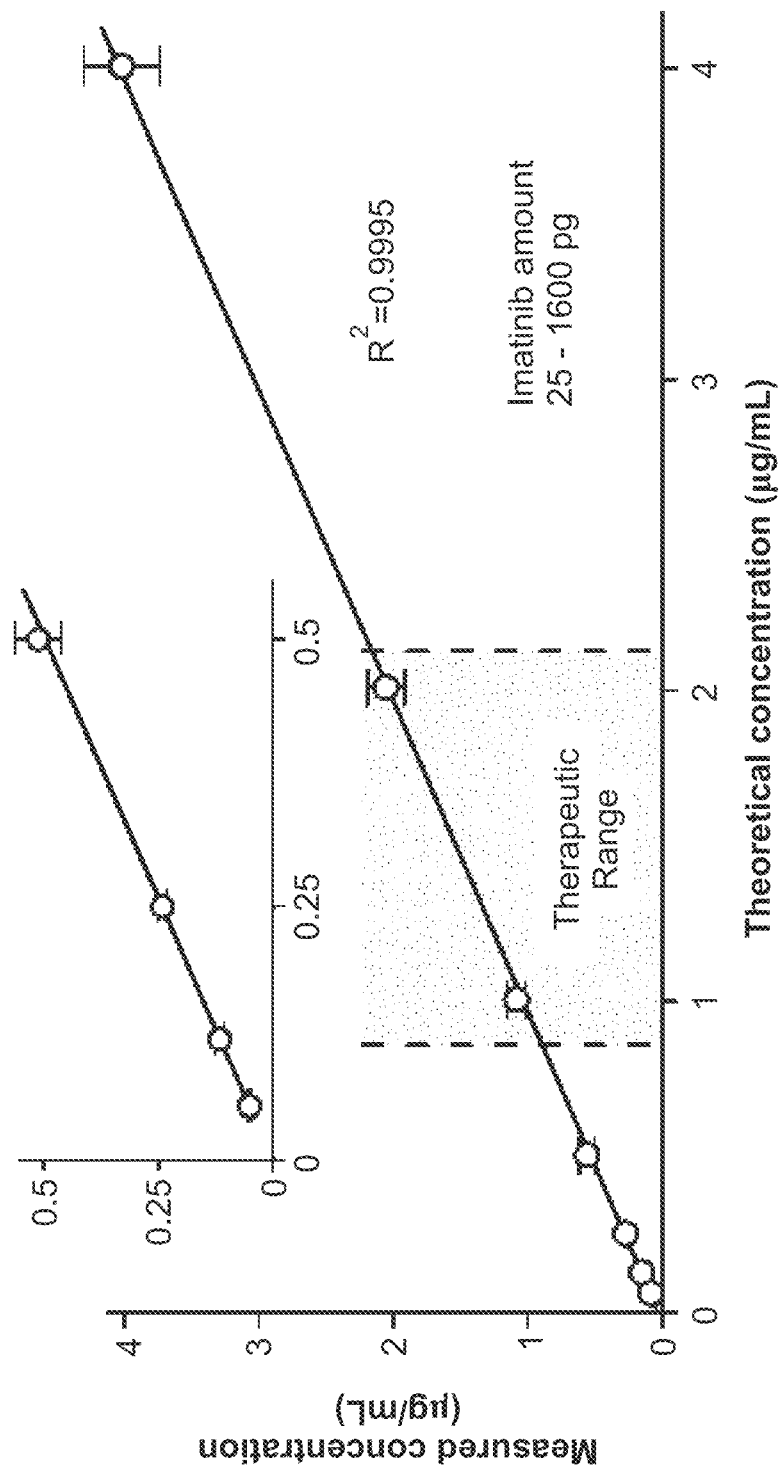

Imatinib (GLEEVEC), a 2-phenylaminopyrimidine derivative, approved by the FDA for treatment of chronic myelogenous leukemia, is efficacious over a rather narrow range of concentrations. Whole human blood, spiked with imatinib at concentrations including the therapeutic range, was deposited on a small paper triangle for analysis (FIG. 14, panel A). The tandem mass spectrum (MS/MS, FIG. 14 panel B) of protonated imatinib, m/z 494, showed a single characteristic fragment ion. Quantitation of imatinib in whole blood was achieved using this signal and that for a known concentration of imatinib-d8 added as internal standard. The relative response was linear across a wide range of concentrations, including the entire therapeutic range (FIG. 14 panel C).

Atenolol, a β-blocker drug used in cardiovascular diseases, was tested using the dried blood spot method to evaluate paper spray for whole blood analysis. Atenolol was directly spiked into whole blood at desired concentrations and the blood sample was used as described above for paper spray. The protonated atenolol of 400 pg (1 ug/mL atenolol in 0.4 uL whole blood) in dried blood spot was shown in mass spectra, and the MS/MS spectra indicated that even 20 pg of atenolol (50 ug/mL atenolol in 0.4 uL whole blood) could be identified in the dried blood spot (FIG. 23 panel B).

FIG. 23 panel (C) is a mass spectra of heroin in whole blood. Data herein show that 200 pg heroin in dried blood spot could be detected using tandem mass.

Figure 18:
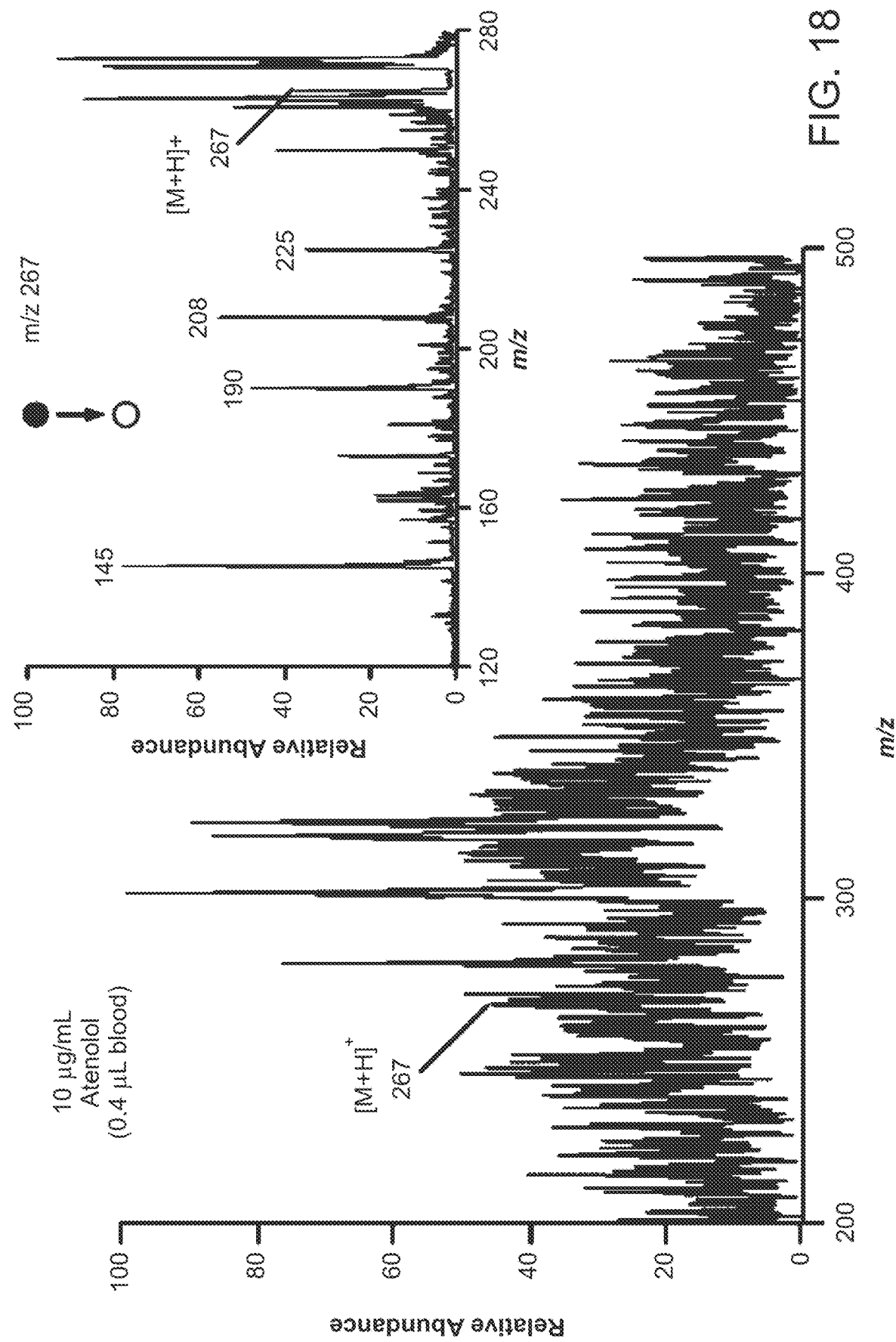
FIG. 18 is a mass spectrum of whole blood spiked with 10 μg/mL atenolol. The data was obtained by combining systems and methods of the invention with a handheld mass spectrometer.
Figure 19A:
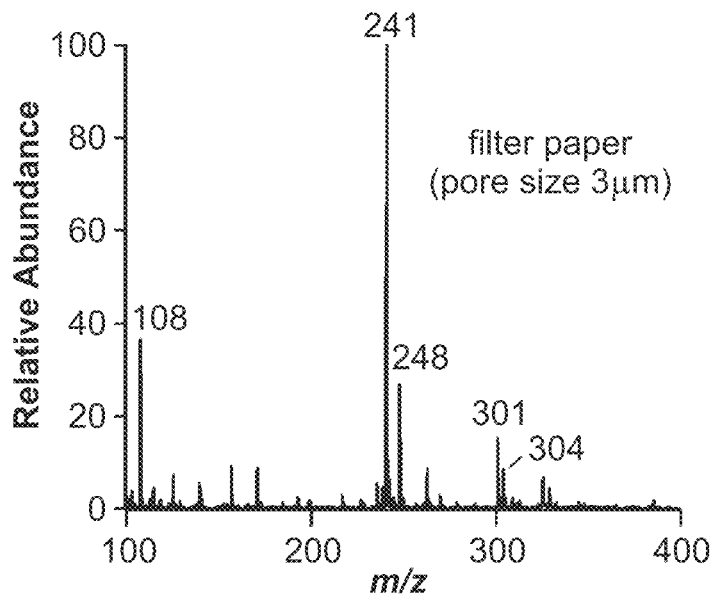
FIG. 19 panels A-F show mass spectra of cocaine sprayed from six different types of paper (Whatman filter paper with different pore sizes: (a) 3 μm, (b) 4-7 μm, (c) 8 μm, and (d) 11 μm, (e) glass fiber paper and (f) chromatography paper). The spray voltage was 4.5 kV.
Figure 19B:
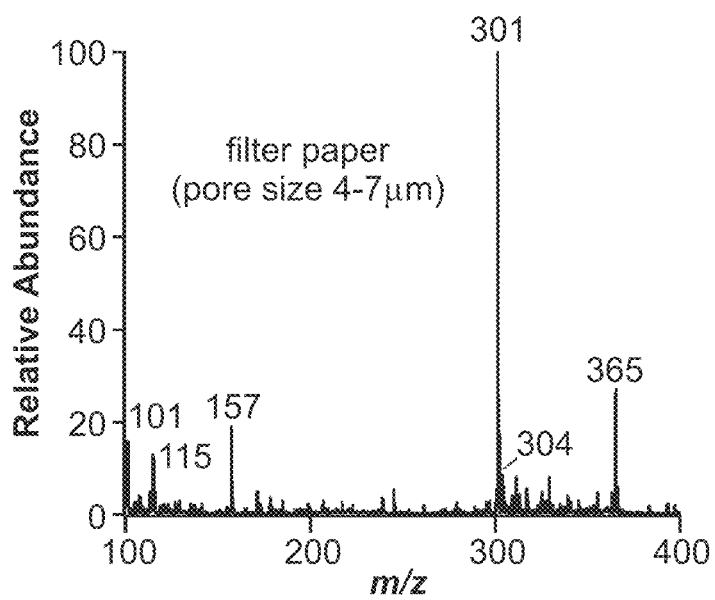
Figure 19C:
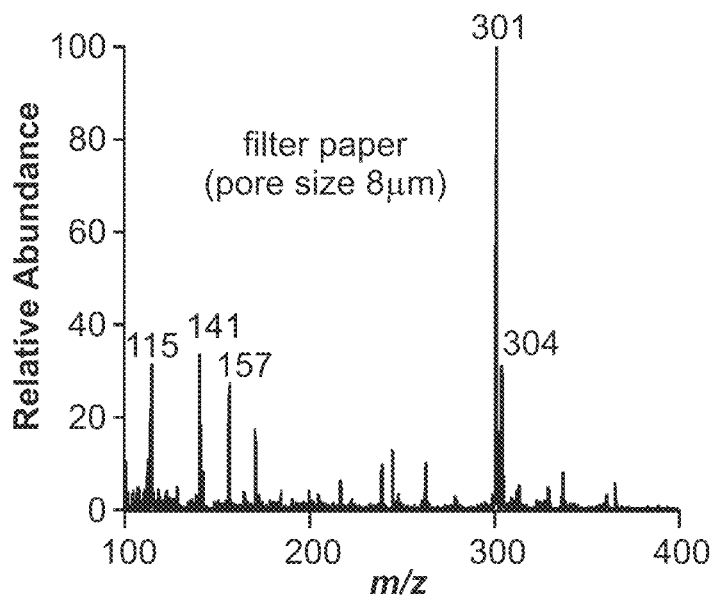
Figure 19D:
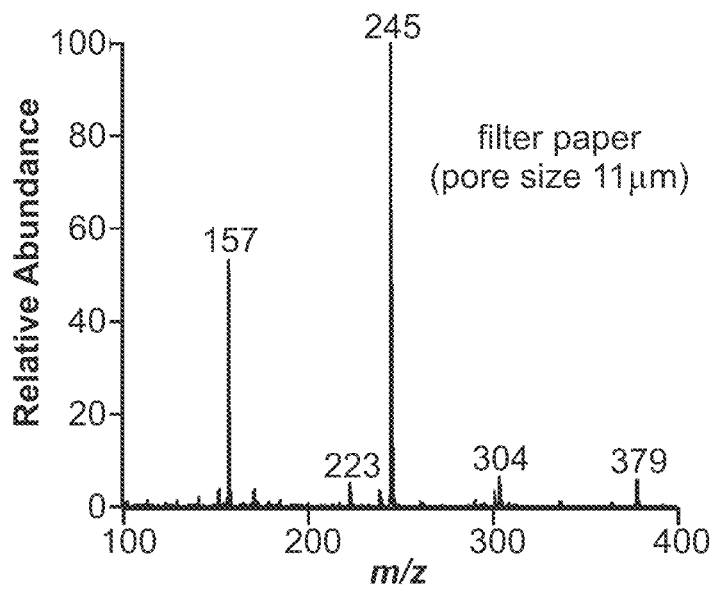
Figure 19E:
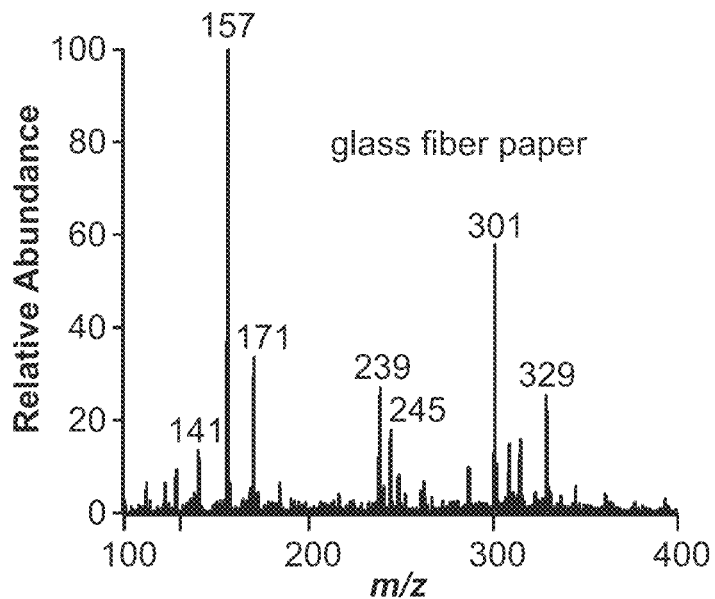
Figure 19F:
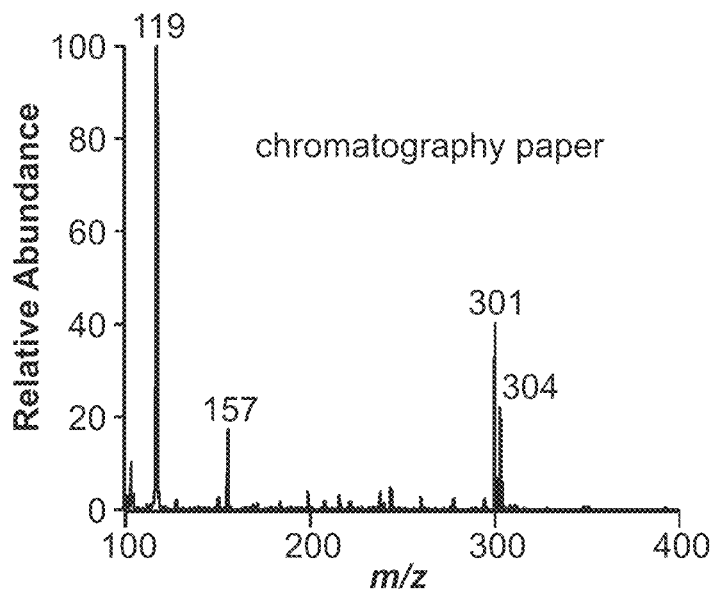

It was also observed that the paper medium served a secondary role as a filter, retaining blood cells. Significantly, samples were analyzed directly on the storage medium rather than requiring transfer from the paper before analysis. All experiments were done in the open lab environment. Two additional features indicated that the methodology had the potential to contribute to increasing the use of mass spectrometry in primary care facilities: blood samples for analysis were drawn by means of a pinprick rather than a canula; and the experiment was readily performed using a handheld mass spectrometer (FIG. 18 and Example 10 below).

Example 10: Handheld Mass Spectrometer

Systems and methods of the invention were compatible with a handheld mass spectrometer. Paper spray was performed using a handheld mass spectrometer (Mini 10, custom made at Purdue University). Analysis of whole blood spiked with 10 µg/mL atenolol. Methanol/water (1:1; 10 µL) was applied to the paper after the blood (0.4 uL) had dried (~1 min) to generate spray for mass detection (FIG. 18). The inset shows that atenolol could readily be identified in whole blood using tandem mass spectrum even when the atenolol amount is as low as 4 ng.

Example 11: Angiotensin I

Figure 15:
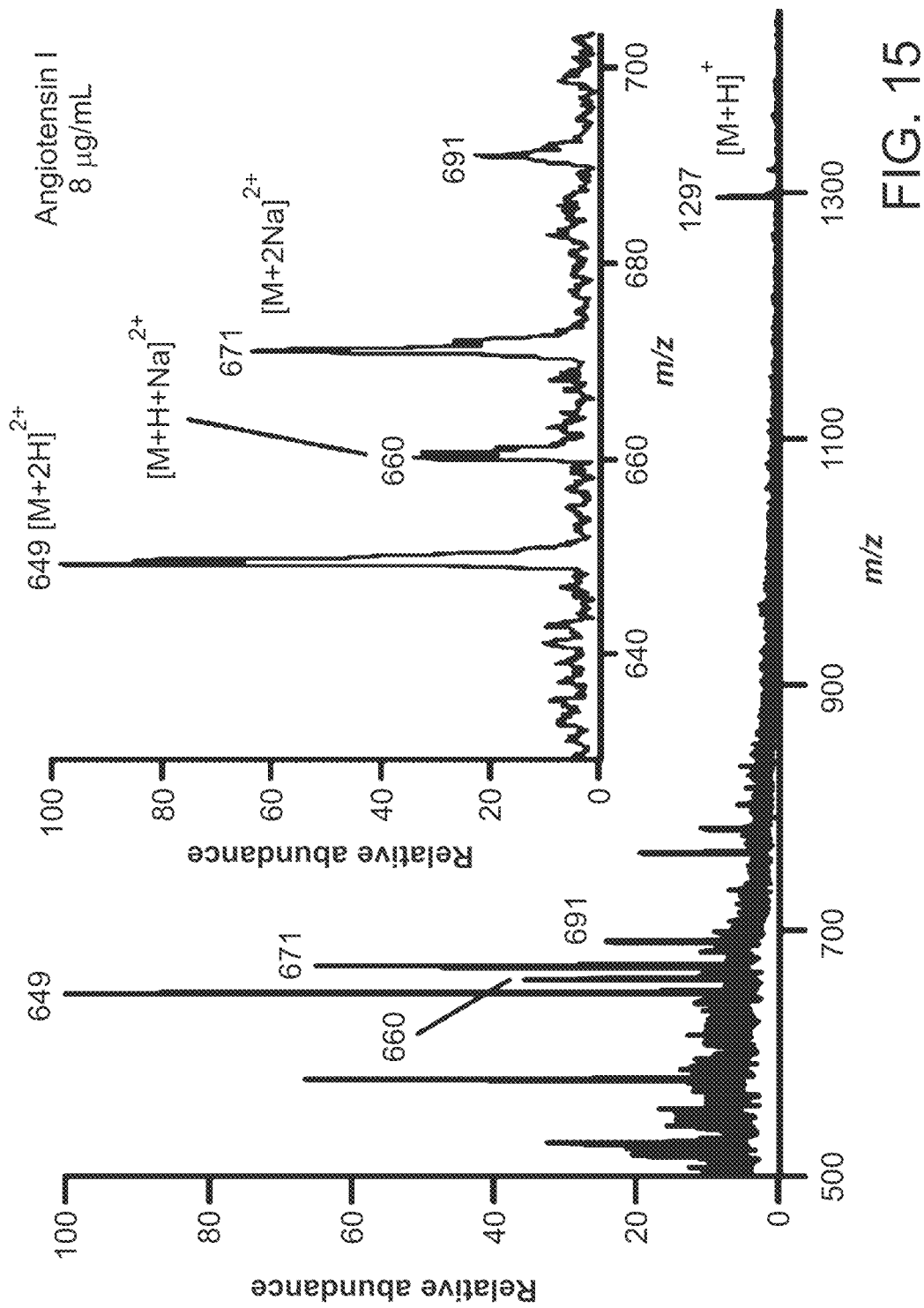
FIG. 15 is a paper spray mass spectrum of angiotensin I solution. The inset shows an expanded view over the mass range 630-700.

FIG. 15 is a paper spray mass spectrum of angiotensin I solution (Asp-Arg-Val-Tyr-Ile-His-Pro-Phe-His-Leu (SEQ ID NO: 1), 10 µL, 8 µg/mL in methanol/water, 1:1, v/v) on chromatography paper (spray voltage, 4.5 kV). The inset shows an expanded view over the mass range 630-700. The protonated ($[M+2H]^{2+}$) and sodium-adduct ions ($[M+H+Na]^{2+}$, $[M+2Na]^{2+}$) are the major ionic species.

Example 12: Agrochemicals on Fruit

Sample collection by paper wiping followed by analysis using probes of the invention was used for fast analysis of agrochemicals on fruit. Chromatography paper (3×3 cm) wetted with methanol was used to wipe a 10 $cm^2$ area on the peel of a lemon purchased from a grocery store. After the methanol had dried, a triangle was cut from the center of the paper and used for paper spray by applying 10 µL methanol/water solution. The spectra recorded (FIG. 34 panels A-B) show that a fungicide originally on the lemon peel, thiabendazole (m/z 202 for protonated molecular ion and m/z 224 for sodium adduct ion), had been collected onto the paper and could be identified easily with MS and confirmed using MS/MS analysis. Another fungicide imazalil (m/z 297) was also observed to be present.

Example 13: Tumor Sample

Systems and methods of the invention were used to analyze human prostate tumor tissue and normal tissue. Tumor and adjacent normal tissue sections were 15 µm thick and fixed onto a glass slide for an imaging study using desorption electrospray ionization (DESI). A metal needle was used to remove a 1 $mm^2$×15 µm volume of tissue from the glass slide from the tumor region and then from the normal region and place them onto the surface of the paper triangle for paper spray analysis.

Figure 17A:
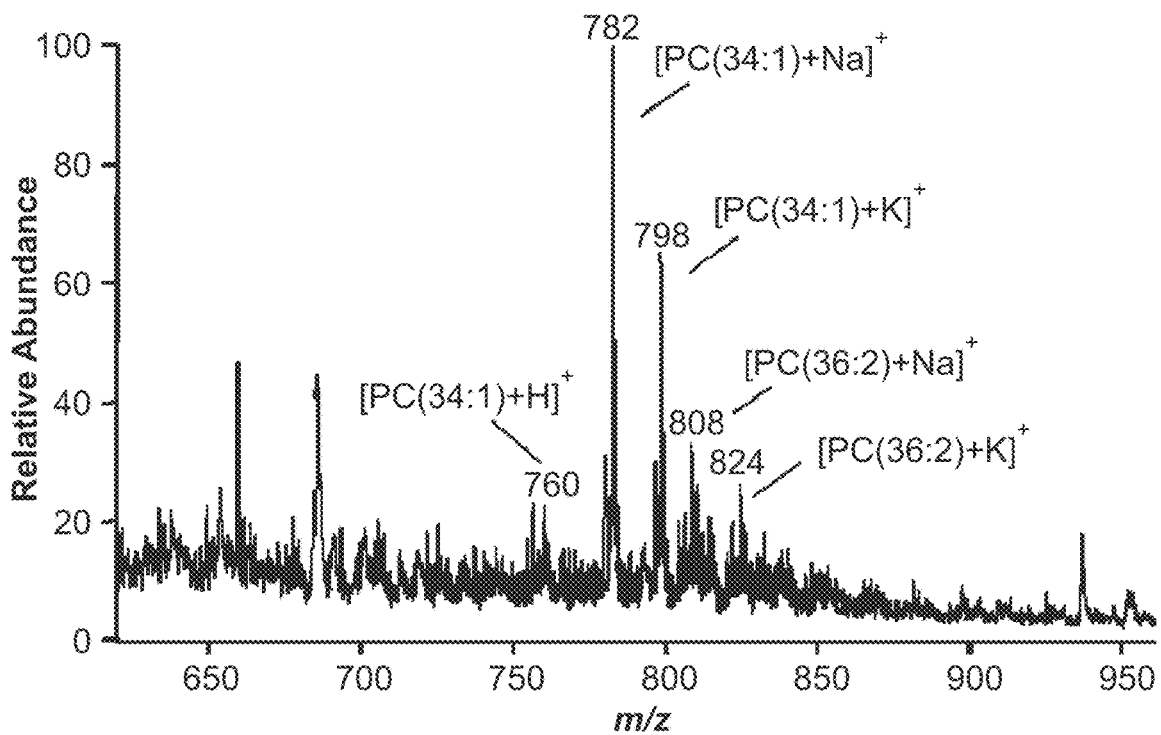
FIG. 17 panels A and B are mass spectra showing direct analysis of human prostate tumor tissue and normal tissue.
Figure 17B:
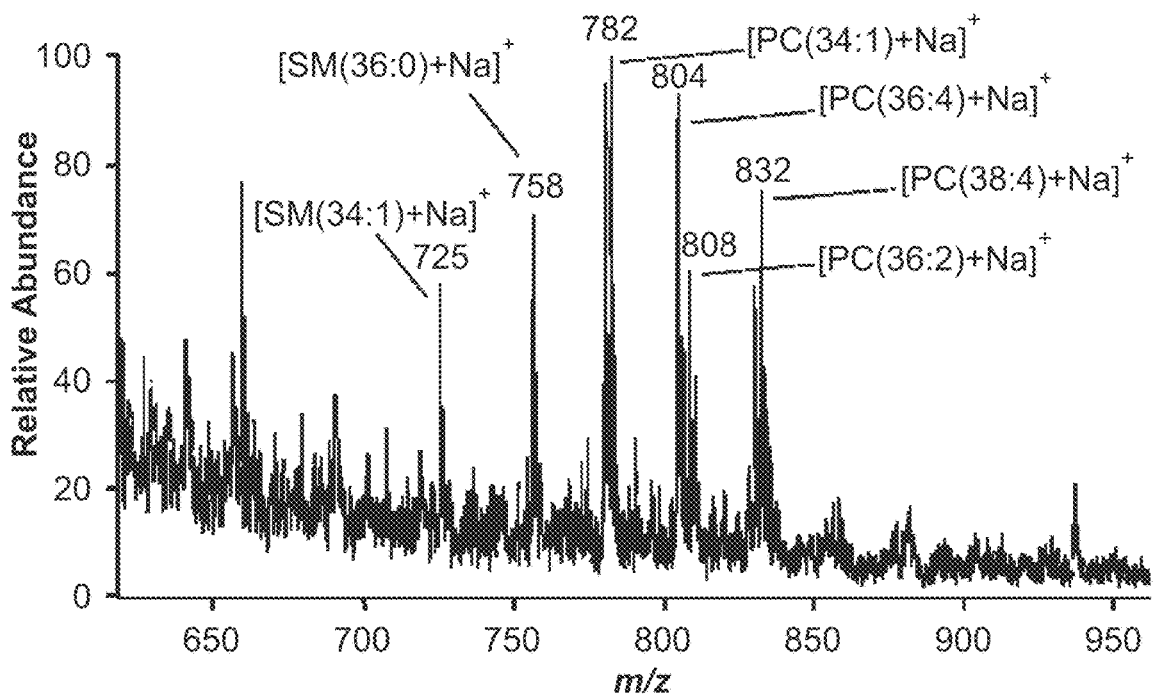

A droplet of methanol/water (1:1 v:v; 10 µl) was added to the paper as solvent and then 4.5 kV positive DC voltage applied to produce the spray. Phospholipids such as phosphatidylcholine (PC) and sphingomyelin (SM) were identified in the spectrum (FIG. 17 panels A and B). The peak of $[PC(34:1)+K]^+$ at m/z 798 was significantly higher in tumor tissue and peaks $[SM(34:1)+Na]^+$ at m/z 725, $[SM(36:0)+Na]^+$ at m/z 756, and $[SM(36:4)+Na]^+$ at m/z 804 were significantly lower compared with normal tissue.

Example 14: Therapeutic Drug Monitoring

The administration of a drug depends on managing the appropriate dosing guidelines for achievement of a safe and effective outcome. This guideline is established during clinical trials where the pharmacokinetics (PK) and pharmacodynamics (PD) of the drug are studied. Clinical trials use PK-PD studies to establish a standard dose, which may be fixed or adjusted according formulas using variables like body mass, body surface area, etc. However, the drug exposure, i.e. the amount of drug circulating over time, is influenced by a number of factors that vary from patient to patient. For example, an individuals' metabolic rate, the type and level of plasma proteins, and pre-existing conditions such as renal and/or hepatic impairment all play a role in affecting the exposure of the drug in vivo. Further, administration of a drug in combination with other medications may also affect exposure. As a result, it is often difficult to predict and prescribe an optimum regimen of drug administration.

Over- or underexposure to a drug can lead to toxic effects or decreased efficacy, respectively. To address these concerns, therapeutic drug monitoring (TDM) can be employed. TDM is the measurement of active drug levels in the body followed by adjustment of drug dosing or schedules to increase efficacy and/or decrease toxicity. TDM is indicated when the variability in the pharmacokinetics of a drug is large relative to the therapeutic window, and there is an established relationship between drug exposure and efficacy and/or toxicity. Another requirement for TDM is that a sufficiently precise and accurate assay for the active ingredient must be available. Immunoassays and liquid chromatography mass spectrometry (LC-MS) are commonly used methods for TDM. In comparison with immunoassay, LC-MS has advantages which include wide applicability, high sensitivity, good quantitation, high specificity and high throughput. Probes of the invention may be coupled with standard mass spectrometers for providing point-of-care therapeutic drug monitoring.

The drug Imatinib (GLEEVEC in USA and GLIVEC in Europe/Australia, for the treatment of chronic myelogenous leukemia) in a dried blood spot was analyzed using paper spray and a lab-scale LTQ mass spectrometer. Quantitation of Imatinib in whole blood was achieved using the MS/MS spectra with a known concentration of Imatinib-d8 being used as the internal standard (FIG. 14 panel C). The relative response was linear across a wide range of concentrations, including the entire therapeutic range (FIG. 14 panel C).

Example 15: High-Throughput Detection

Figure 28A:
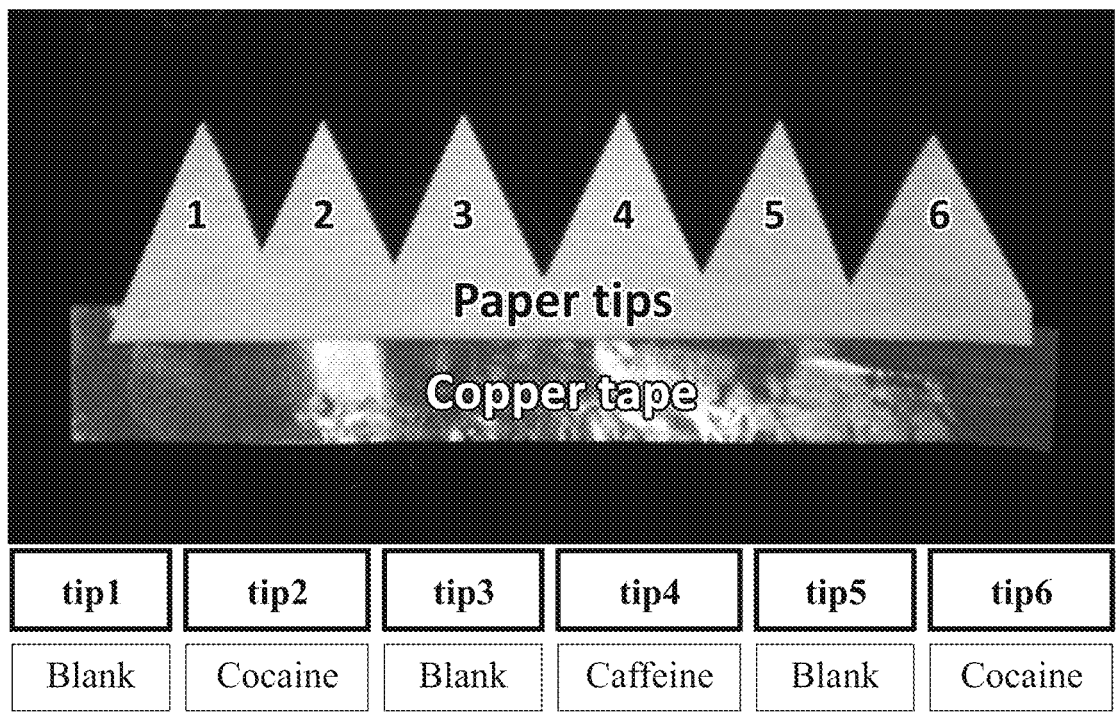
FIG. 28 panel (A) is a picture of a high-throughput probe device of the invention. Panel (B) shows spray from a single tip of the device into an inlet of a mass spectrometer. Panel (C) is a set of mass spectra showing MS signal intensity in high-throughput mode.
Figure 28B:
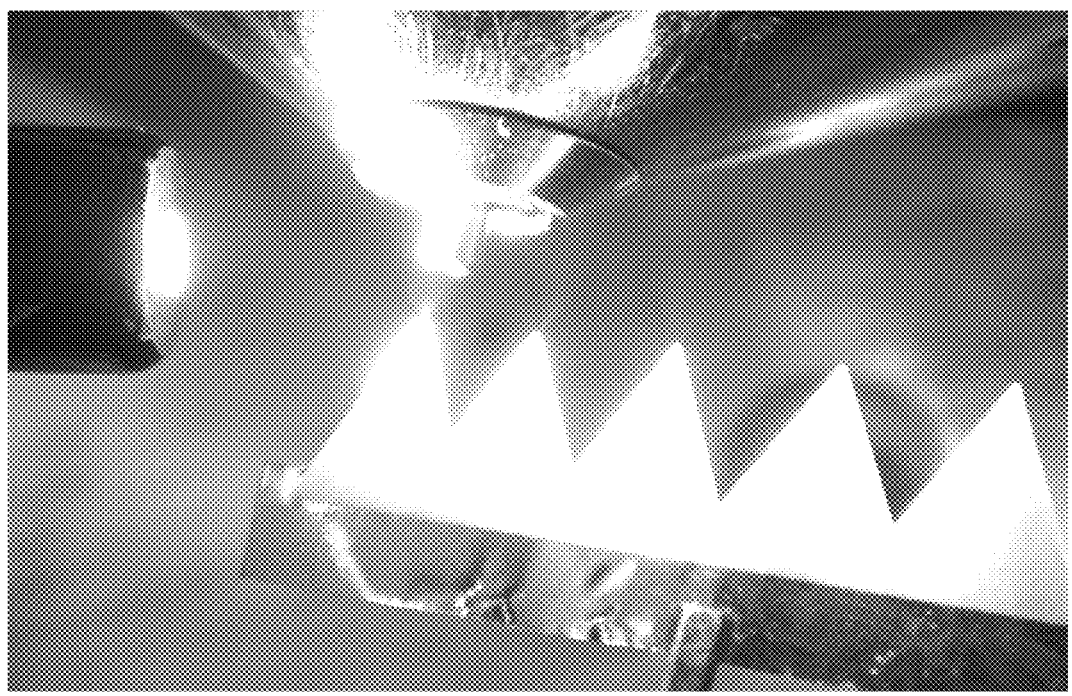
Figure 28C:
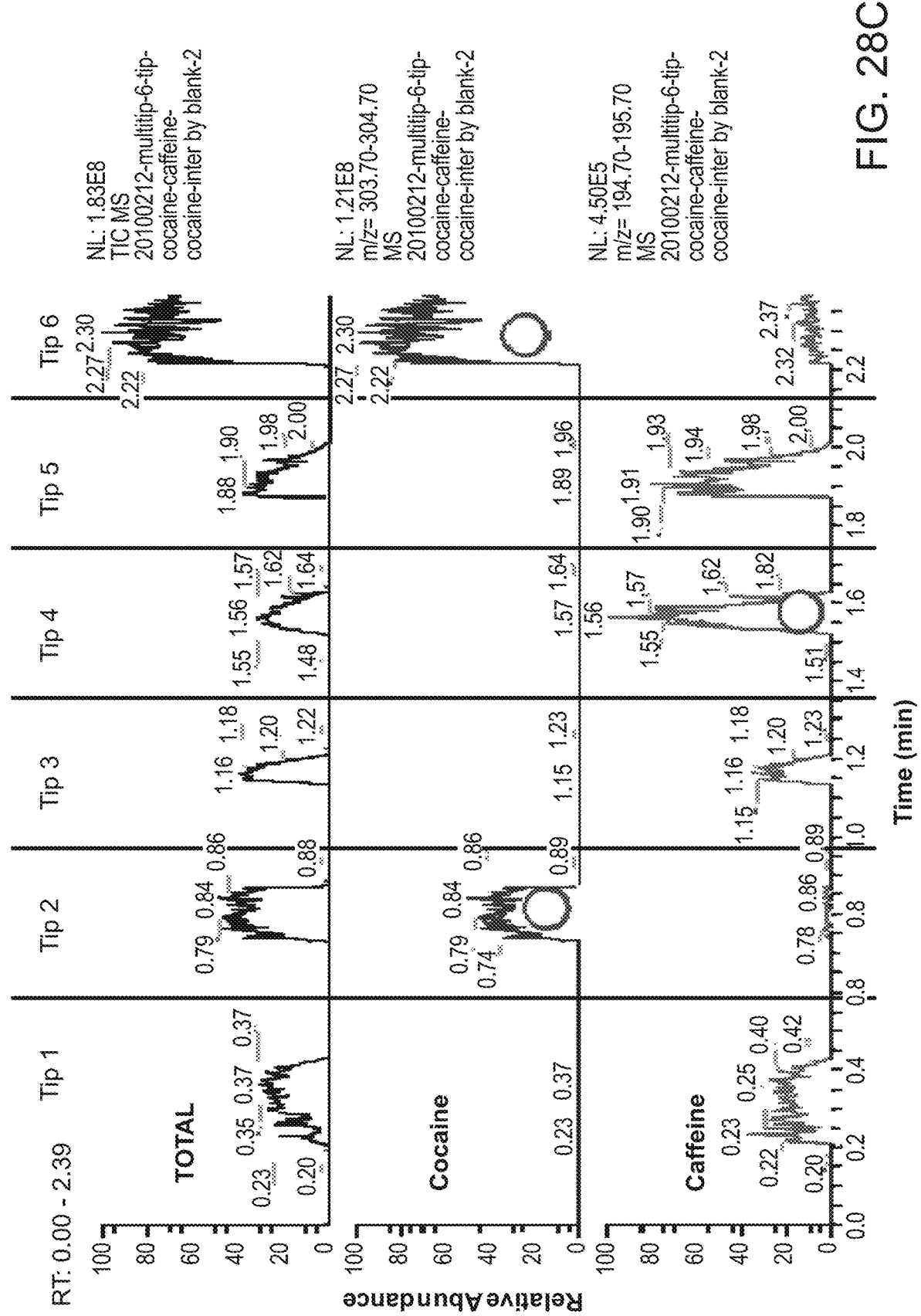

Multiple-tip devices were fabricated and applied for high throughput analysis (FIG. 28 panel A). The multiple-tip device was a set of paper triangles all connected to a single copper strip (FIG. 28 panel A). An electrode was connected to the copper strip. Multiple samples were put on a single paper substrate and analyzed in series using the multiple-tip probe (FIG. 28 panels B-C). Each tip was pre-loaded with 0.2 uL methanol/water containing 100 ppm sample (cocaine or caffeine) and dried. Then the whole multiple-tip device was moved on a moving stage from left to right with constant velocity and 7 uL methanol/water was applied from the back part for each tip during movement.

To prevent the contaminant during spray, blanks were inserted between two sample tips. FIG. 28 panel (C) shows the signal intensity for the whole scanning. From total intensity, six tips gave six individual high signal peaks. For cocaine, peaks only appeared when tip 2 and tip 6 were scanned. For caffeine, the highest peak came from tip 4, which was consistent with the sample loading sequence.

Example 16: Tissue Analysis

Figure 16:
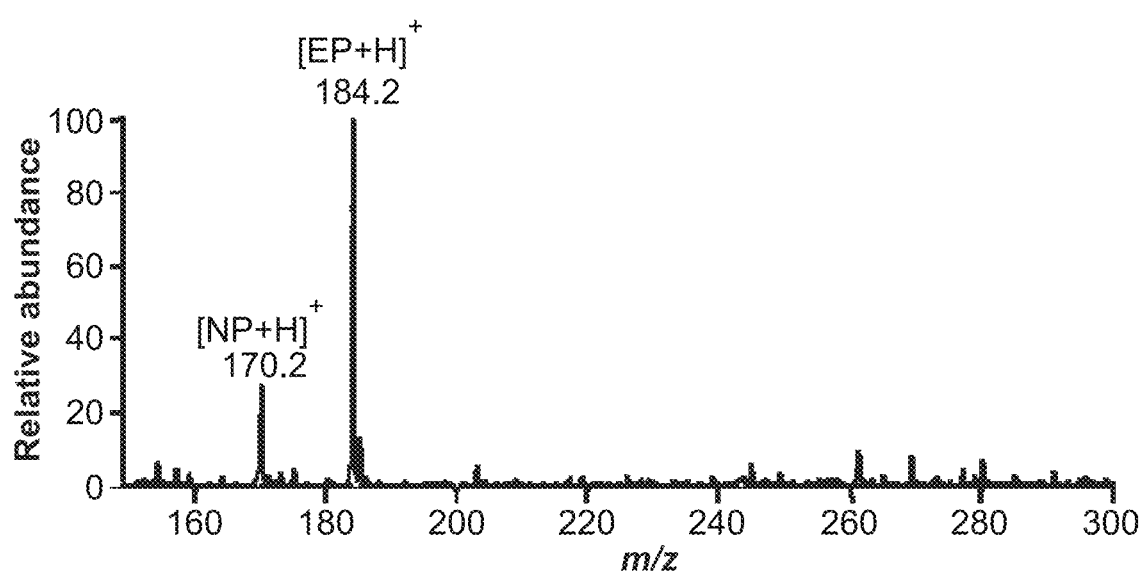
FIG. 16 is a mass spectrum showing direct analysis of hormones in animal tissue by probes of the invention.
Figure 29A:
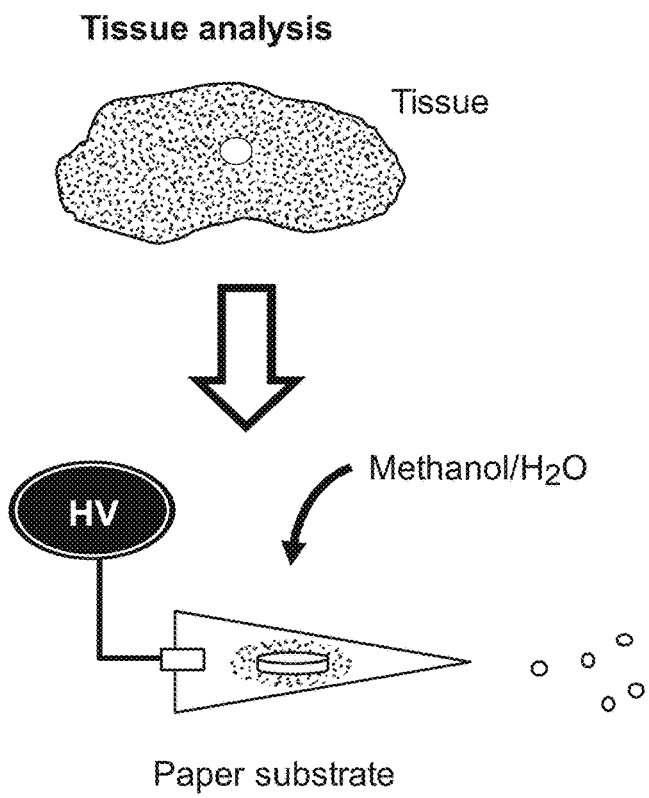
FIG. 29 panel (A) is a schematic depicting a protocol for direct analysis of animal tissue using probes of the invention. Panels (B through D) are mass spectra showing different chemicals detected in the tissue.
Figure 29B:
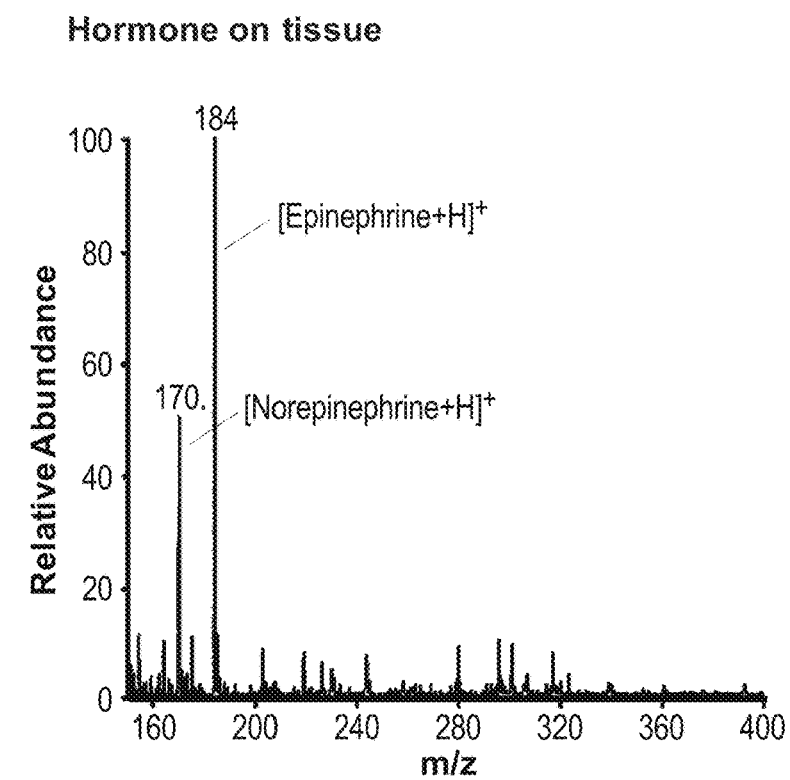

Direct analysis of chemicals in animal tissue using probes of the invention was performed as shown in FIG. 29 panel (A). A small sections of tissue were removed and placed on a paper triangle. Methanol/water (1:1 v:v; 10 µl) was added to the paper as solvent and then 4.5 kV positive DC voltage was applied to produce the spray for MS analysis. Protonated hormone ions were observed for porcine adrenal gland tissue (1 mm$^3$, Panel (B)). FIG. 16 is a mass spectrum showing direct analysis of hormones in animal tissue by paper spray. A small piece of pig adrenal gland tissue (1 mm×1 mm×1 mm) was placed onto the paper surface, MeOH/water (1:1 v:v; 10 µl) was added and a voltage applied to the paper to produce a spray. The hormones epinephrine and norepinephrine were identified in the spectrum; at high mass the spectrum was dominated by phospolipid signals.

Lipid profiles were obtained for human prostate tissues (1 mm$^2$×15 µm, Panel (C) & (D)) removed from the tumor and adjacent normal regions. Phospholipids such as phosphatidylcholine (PC) and sphingomyelin (SM) were identified in the spectra. The peak of [PC(34:1)+K]$^+$ at m/z 798 was significantly more intense in tumor tissue (panel C) and peaks [SM(34:1)+Na]$^+$ at m/z 725, [SM(36:0)+Na]$^+$ at m/z 756, and [SM(36:4)+Na]$^+$ at m/z 804 were significantly lower compared with normal tissue (panel D).

Example 17: On-Line Derivatization

For analysis of target analytes which have relatively low ionization efficiencies and relatively low concentrations in mixtures, derivatization is often necessary to provide adequate sensitivity. On-line derivatization can be implemented by adding reagents into the spray solution, such as methanol/water solutions containing reagents appropriate for targeted analytes. If the reagents to be used are stable on paper, they can also be added onto the porous material when the probes are fabricated.

As a demonstration, 5 µL methanol containing 500 ng betaine aldehyde chloride was added onto a paper triangle and allowed to dry to fabricate a sample substrate preloaded with a derivatization reagent for the analysis of cholesterol in serum. On-line charge labeling with betaine aldehyde (BA) through its reaction with hydroxyl groups has been demonstrated previously to be very effective for the identification of cholesterol in tissue (Wu et al., *Anal Chem.* 2009, 81:7618-7624). When the paper triangle was used for analysis, 2 µL human serum was spotted onto the paper to form a dried spot and then analyzed by using paper spray ionization. A 10 µL ACN/CHCl$_3$ (1:1 v:v) solution, instead of methanol/water, was used for paper spray to avoid reaction between the betaine aldehyde and methanol.

Figure 30A:
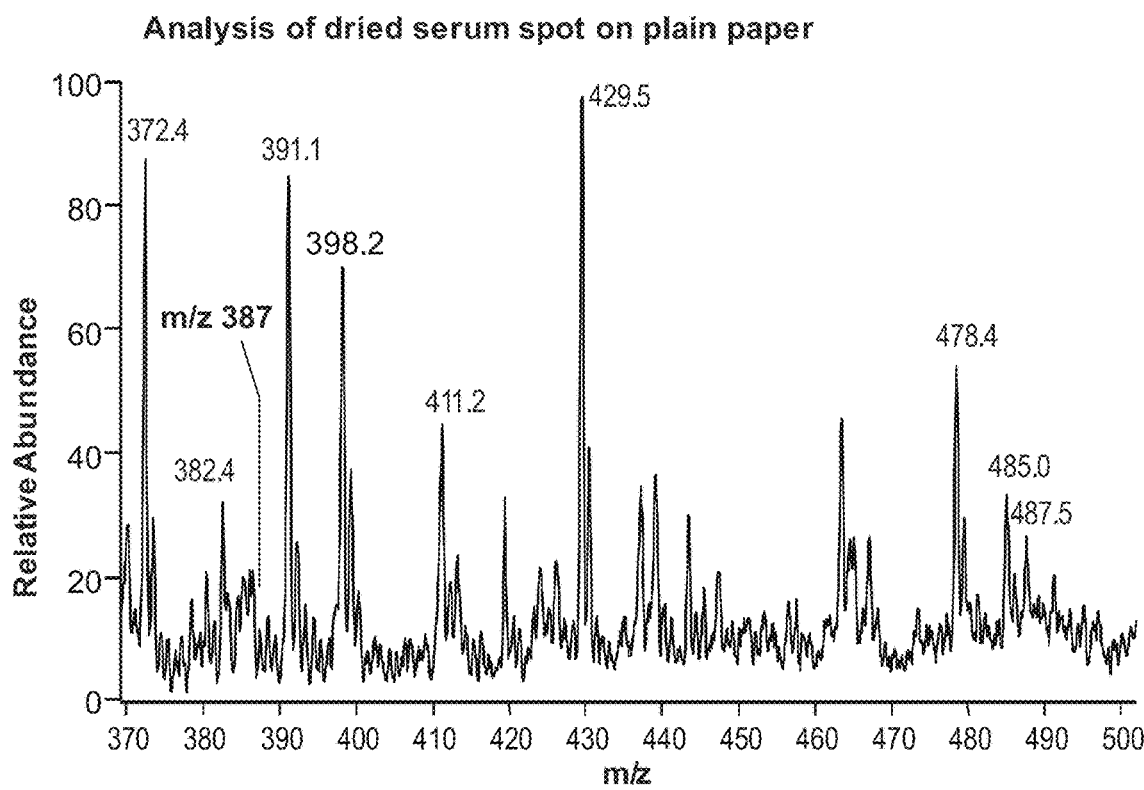
FIG. 30 panel (A) shows a mass spectral analysis of a dried serum spot on plain paper. Panel (B) shows a mass spectrum analysis of a dried serum sport on paper preloaded with betaine aldehyde (BA) chloride. Panel (C) shows a MS/MS analysis of reaction product [M+BA]$^+$ (m/z 488.6).
Figure 30B:
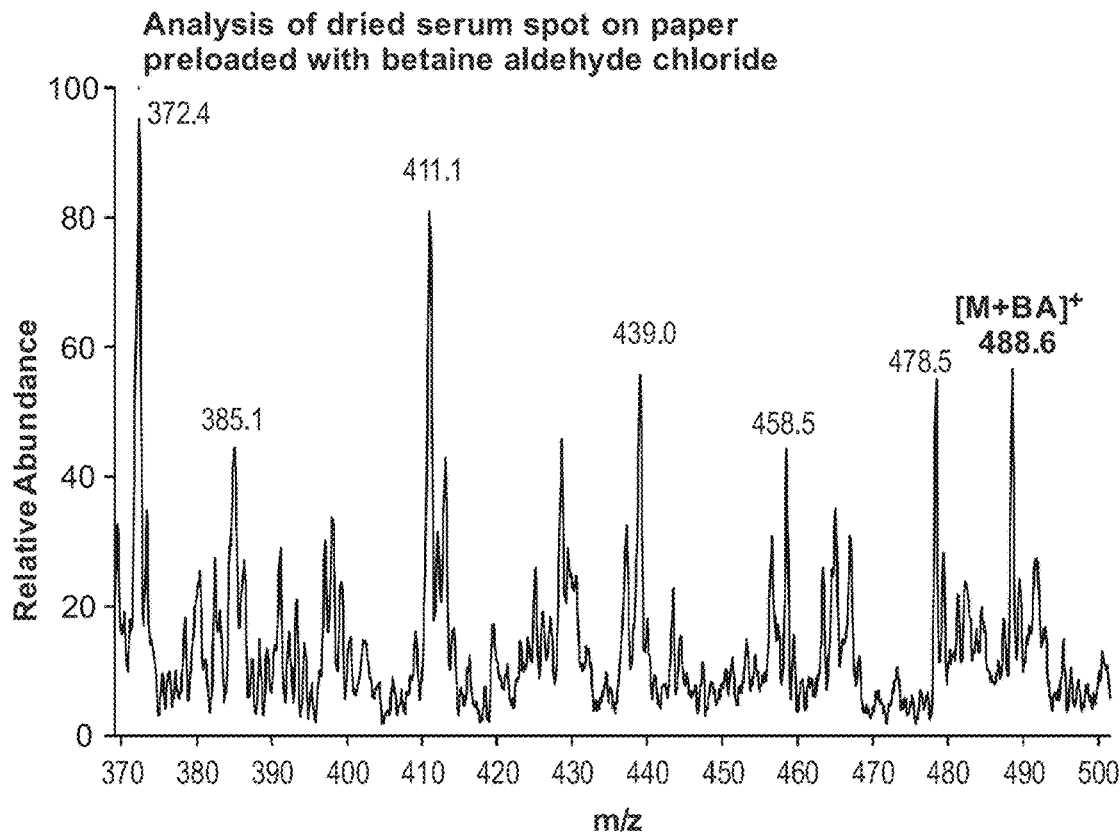
Figure 30C:
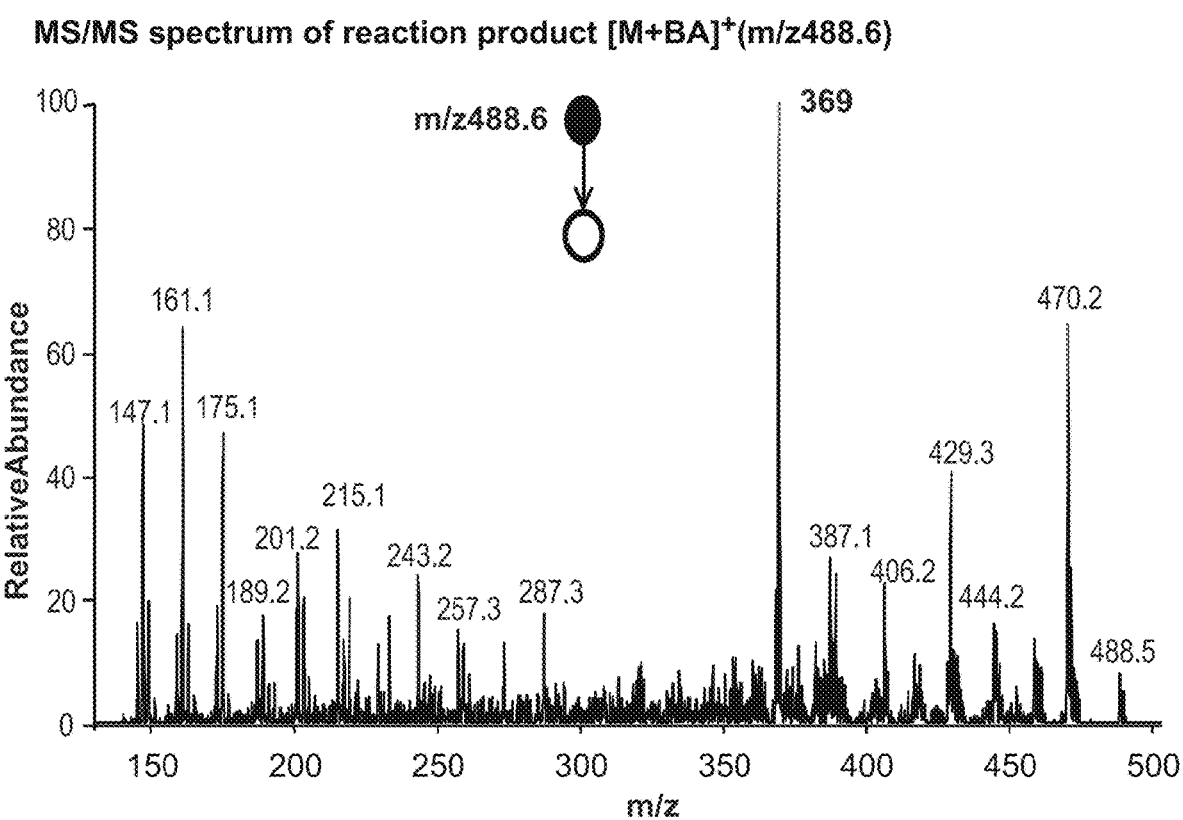

The comparison between analysis using a blank and a reagent-preloaded paper triangle is shown in FIG. 30 panels (A) and (B). Without the derivatization reagent, cholesterol-related peaks, such as protonated ion [Chol+H]$^+$ (m/z 387), water loss [Chol+H—H$_2$O]$^+$ (m/z 369), and sodium adduction [Chol+Na]$^+$ (m/z 409), were not observed (Panel A). With the derivatization reagent, the ion [Chol+BA]$^+$ was observed at m/z 488.6 (Panel B). MS/MS analysis was performed for this ion and a characteristic fragment ion m/z 369 was observed (Panel C).

Example 18: Peptide Pre-Concentration Using Modified Paper Spray Substrate

Pre-concentration of chemicals on the paper surface using photoresist treatment. Chromatography paper was rendered hydrophobic by treatment with SU-8 photoresist as described previously (Martinez et al., *Angew Chem Int. Ed.,* 2007, 46:1318-1320). Then 5 µl bradykinin 2-9 solution (100 ppm in pure H$_2$O) was applied on the paper surface. When the solution was dry, the paper was put into water and washed for 10 s. After washing, the paper triangle was held in front of the MS inlet, 10 µl pure MeOH was applied as solvent and the voltage was set at 4.5 kV for paper spray. The same experiment was done with untreated paper substrate for comparison.

Figure 31A:
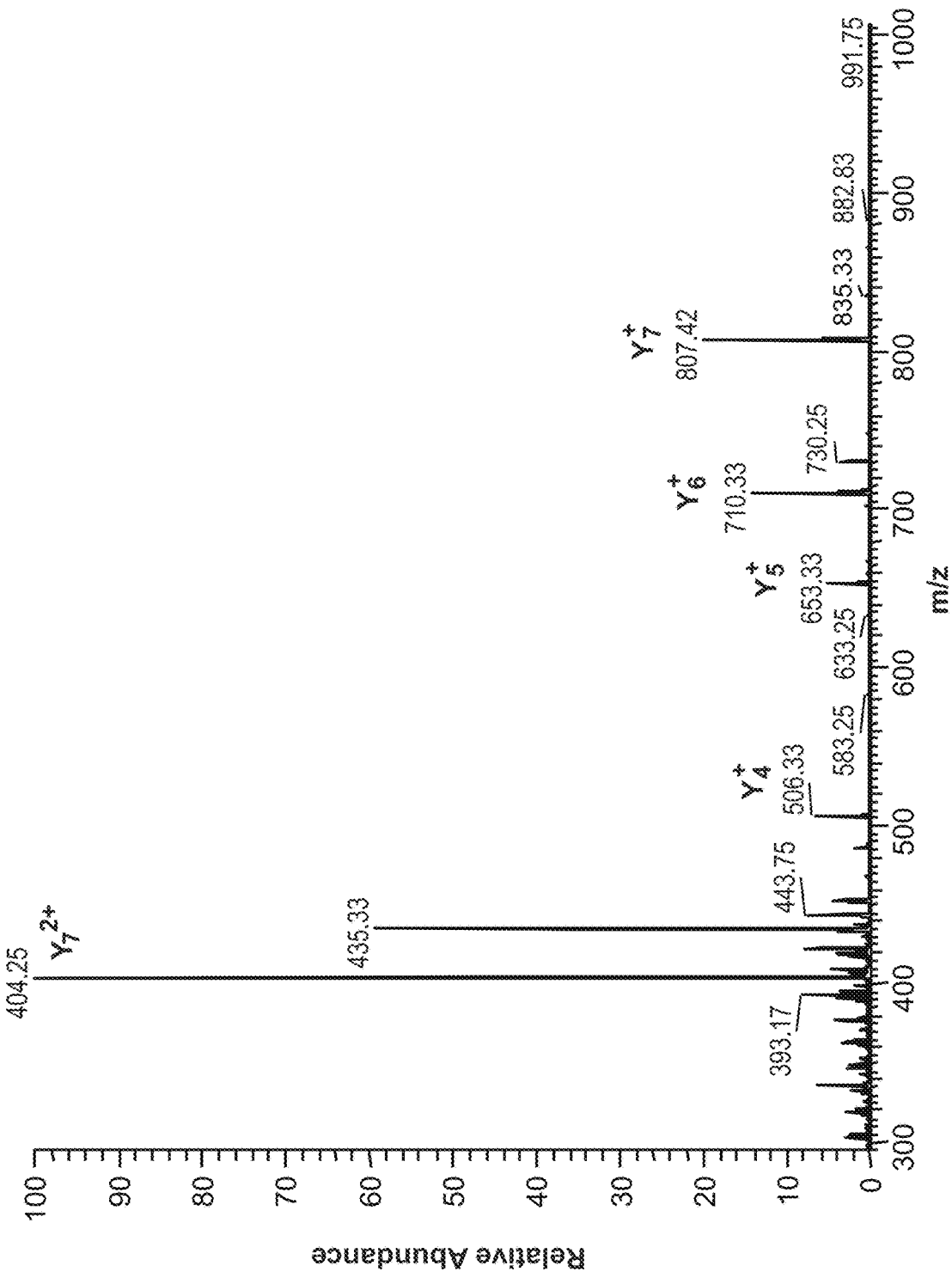
FIG. 31 shows MS/MS spectra recorded with modified (panel A) and unmodified (panel B) paper substrates.
Figure 31B:
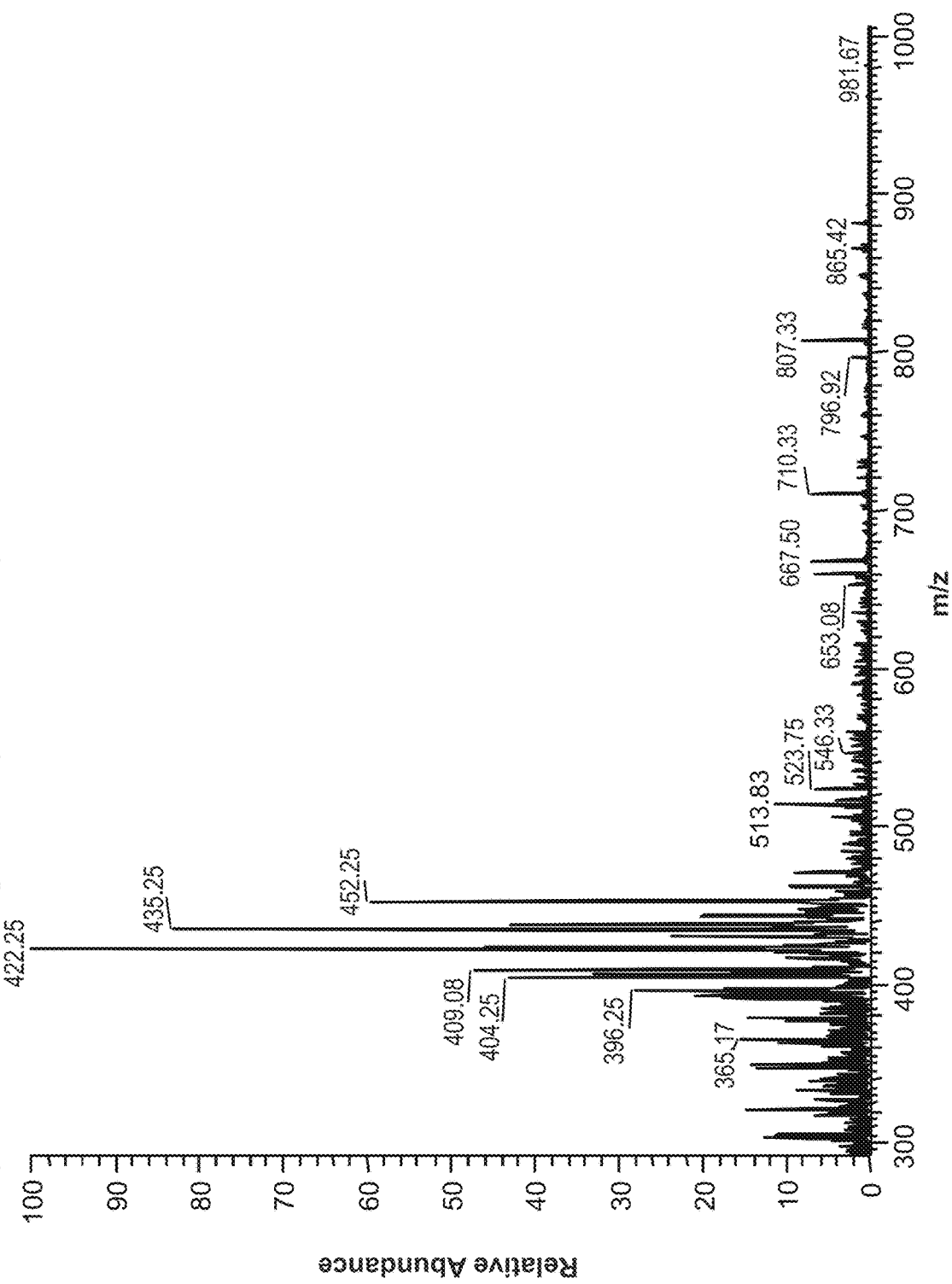

FIG. 31 panel (A) shows the tandem MS spectrum of bradykinin 2-9 from paper with photoresist treatment. The intensity of the most intense fragment ion 404 is 5.66E3. FIG. 31 panel (B) shows the tandem MS spectrum of bradykinin 2-9 from normal chromatography paper without photoresist treatment. The intensity of the most intense fragment ion 404 is only 1.41E1. These data show that the binding affinity between photoresist-treated chromatography paper and peptide is much higher than that between normal chromatography paper and peptide, thus more peptide can be kept on the paper surface after washing by water. When pure methanol is applied, these retained peptides will be desorbed and detected by MS. This method can be used to pre-concentrate hydrophobic chemicals on the paper surface, and other hydrophilic materials (e.g. salts) can also be removed from the paper surface.

Example 19: Inverted Polarities

The polarity of the voltage applied to the probe need not match that used in the mass analyzer. In particular, it is possible to operate the probes of the invention with a negative potential but to record the mass spectrum of the resulting positively changed ions. In negative ion mode, a large current of electrons (or solvated electrons) is produced in paper spray. These electrons, if of suitable energy, can be captured by molecules with appropriate electron affinities to generate radical anions.

Alternatively, these electrons might be responsible for electron ionization of the analyte to generate the radical cation or alternatively ESI might involve a solvent molecule which might then undergo charge exchange with the analyte to again generate the radical cation. If this process occurs with sufficient energy, characteristic fragment ions might be produced provided the radical cation is not collisionally deactivated before fragmentation can occur.

Figure 32:
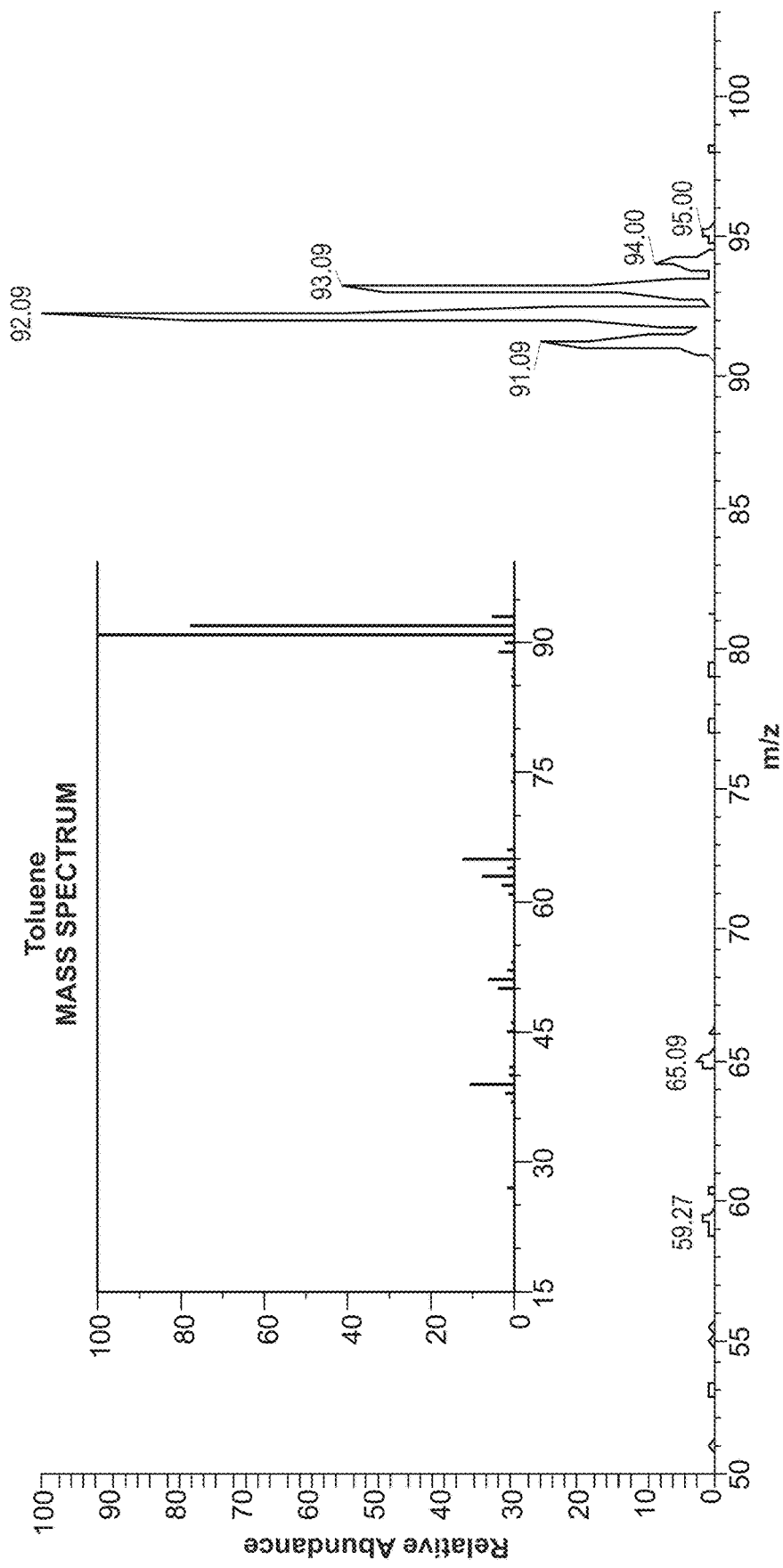
FIG. 32 is a mass spectrum showing that ions can be generated using a negative ion source potential but positively charged ions are mass-analyzed.

An experiment was done on a benchtop LTP using toluene vapor, with a probe of the invention conducted at −4.5 kV with methanol:water as solvent applied to the paper. The spectrum shown in FIG. 32 was recorded. One notes that ion/molecule reactions to give the protonated molecule, m/z 93 occur as expected at atmospheric pressure. One also notes however, the presence of the radical cation, m/z 92 and its characteristic fragments at m/z 91 and 65.

An interesting note is that the "EI" fragment ions were most easily produced when the source of toluene vapor was placed close to the MS inlet; i.e., in the cathodic region of the discharge between the paper tip and MS inlet. This suggests that direct electron ionization by energetic electrons in the "fall" region might be at least partly responsible for this behavior.

Example 20: Cartridge for Blood Analysis

Figure 33A:
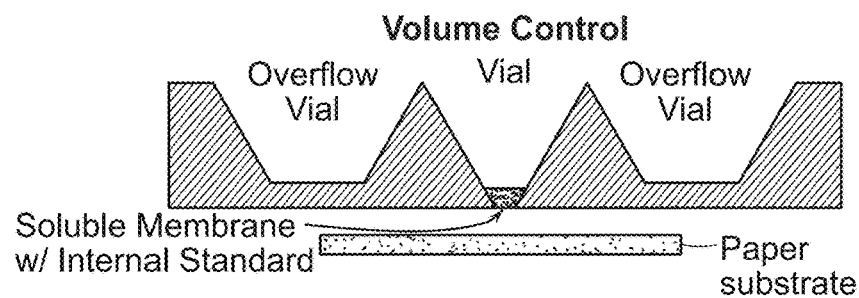
FIG. 33 panel (A) is a schematic showing the design of a sample cartridge with volume control and overflowing vials. A soluble plug with internal standard chemical is used to block the bottom of the volume control vial. Panel (B) shows a step-by-step process of applying blood samples onto the cartridge to prepare a dried blood spot on paper from a controlled volume of blood.
Figure 33B:
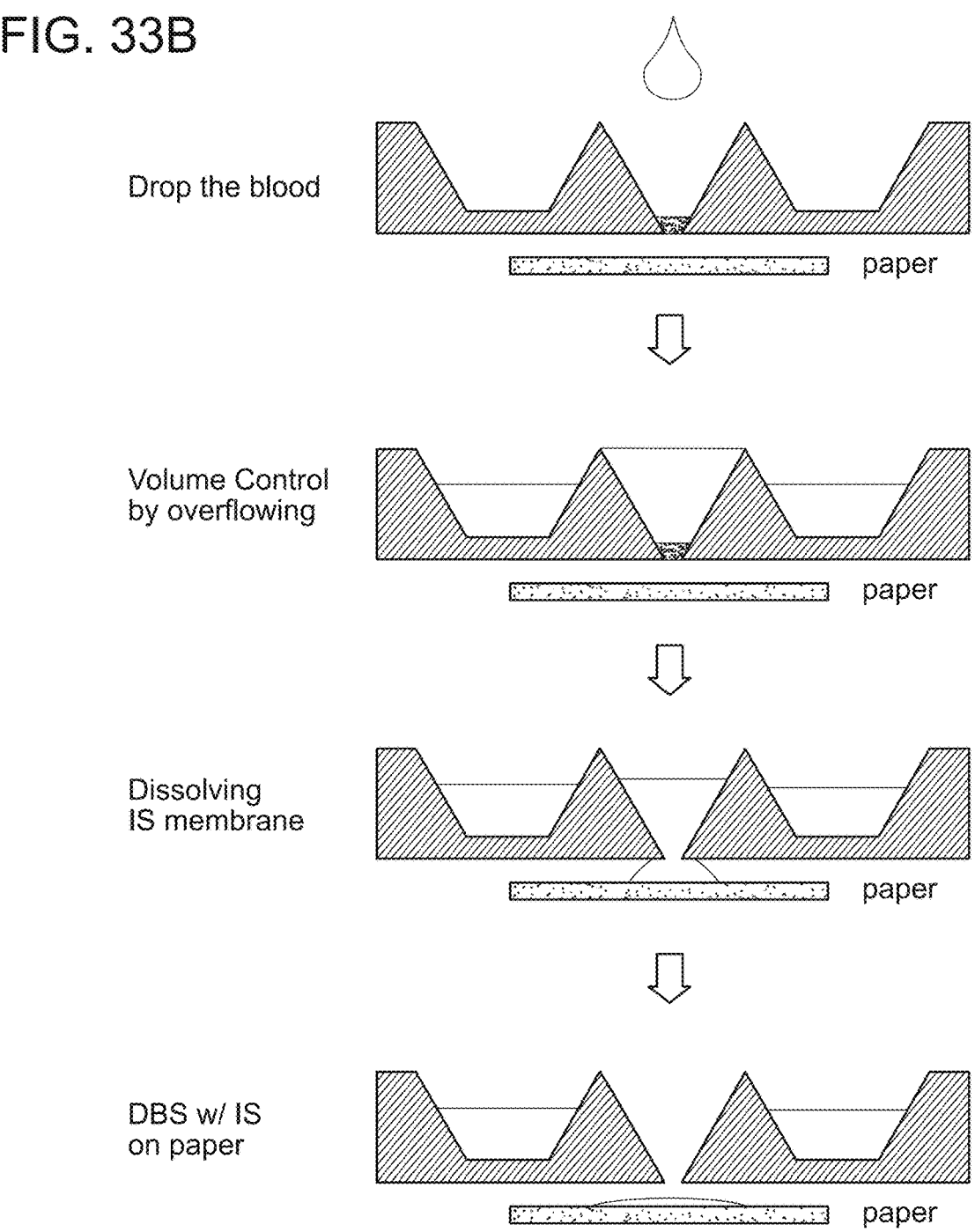
Figure 36A:
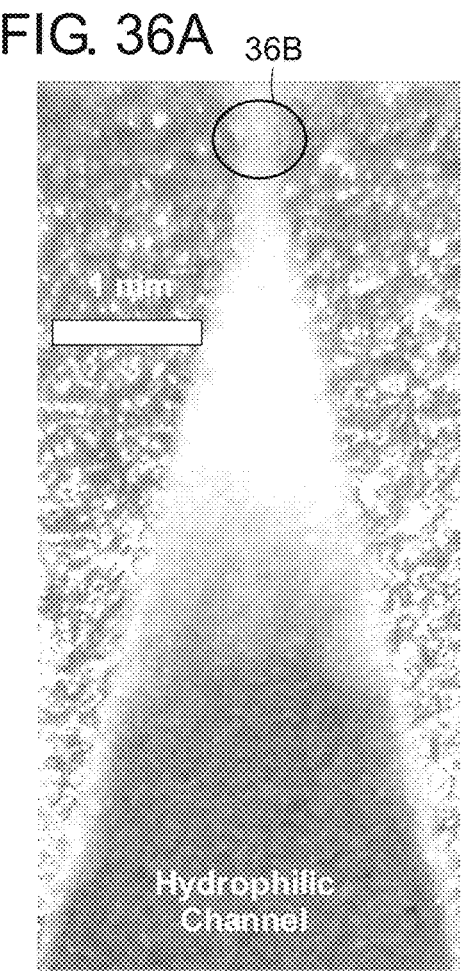
FIG. 36 panels (A and B) show a spray tip fabricated on a piece of chromatography paper using SU-8 2010 photoresist. Panel (C) shows a MS spectrum of methanol/water solution containing a mixture of asparagines.
Figure 36B:
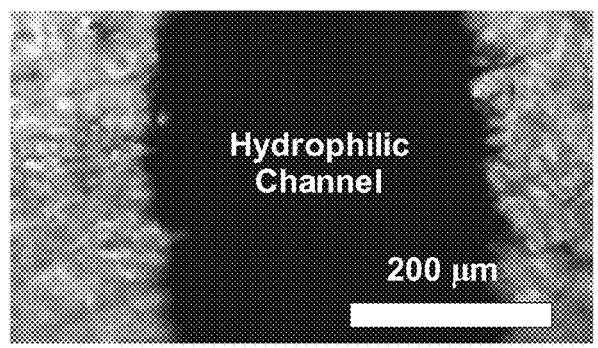
Figure 36C:
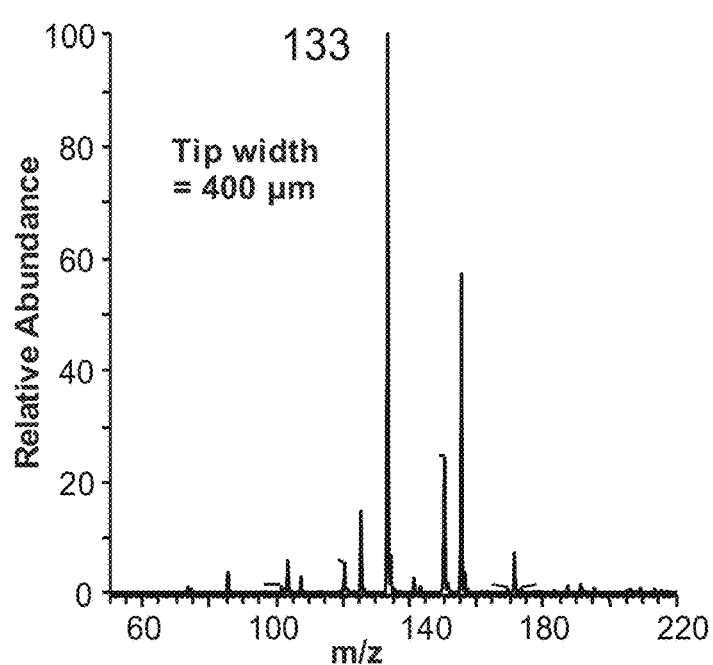

FIG. 33 panel (A) shows an exemplary case for spotting blood onto porous material that will be used for mass spectral analysis. The cartridge can have a vial with a volume at the center and vials for overflows. A plug, such as a soluble membrane containing a set amount of internal standard chemical, is used to block the bottom of the vial for volume control. A drop of blood is placed in the vial (Panel B). The volume of the blood in the vial is controlled by flowing the extra blood into the overflow vials (Panel B). The blood in the vial is subsequently dissolved in the membrane at the bottom, mixing the internal standard chemical into the blood (Panel B). Upon dissolution of the plug, blood flows to the paper substrate, and eventually forms a dried blood spot having a controlled amount of sample and internal standard (Panel B).

Example 21: Sample Dispenser Including an Internal Standard

This example provides a device for transfer of complex mixture using, e.g., glass capillaries coated with internal standard. A sampling glass capillary was prepared by filling it with an internal standard solution through capillary action and drying in air to form an internal standard coating on its inner surface. The capillary was used to take a liquid sample containing the analyte, also through capillary action, and to transfer it to a sample substrate for ambient analysis. During this process the internal standard was automatically mixed into the sample. Since the volumes of the internal standard solution and sample are both regulated by the capillary volume, accurate control of the capillary length of volume is not necessary to retain quantitative accuracy, which is good for mass production of the capillaries. The performance of using sampling capillary for quantitative analysis of different chemicals in complex mixtures, including blood, river water and urine was characterized. Significant improvements in quantitation accuracy were obtained for analysis of 1 μL samples using various ambient ionization methods, including paper spray ionization, low temperature plasma (LTP) and desorption electrospray ionization (DESI).

Materials

Glass capillaries (I.D. 0.4 mm; length, 75 mm) were purchased from Drummond Scientific Co. (Broomall, Pa.). Pipette tips (1000 μL) were purchased from Eppendorf (Hauppauge, N.Y.). Whatman Grade 1 chromatography paper was purchased from GE Healthcare UK Limited (Buckinghamshire, England). Imatinib was purchased from Santa Cruz Biotechnology (Santa Cruz, Calif.), imatinib-d8 was purchased from EJY Tech (Rockville, Md.). Atrazine, atrazine-d5, cocaine, and cocaine-d3 were purchased from Sigma-Aldrich (Milwaukee, Wis.). Bovine blood (sodium citrate) was purchased from Innovative Research (Novi, Mich.). River water was collected from Wabash River (West Lafayette, Ind.). Urine was collected from a group member.

Blood samples were examined with paper spray ionization by using a TSQ Quantum Access Max (Thermo Scientific, San Jose, Calif.) in the selected reaction monitoring (SRM) mode. River water and urine samples were examined with LTP and DESI, respectively, by using an Exactive Orbitrap (Thermo Scientific, San Jose, Calif.) in full scan mode. For paper spray mass spectrometry, the chromatography paper was cut into triangle (5 mm in base and 10 mm in height). The paper triangle was held by clip and placed in front of the MS inlet with a 5 mm distance. Spray solvent (35 μL acetonitrile: water, 90:10, v:v) was applied on the blood spot to extract chemicals for MS detection. For LTP measurement, the river water was deposited on glass slide and allowed to dry. Experiment conditions for LTP includes Helium gas flow 0.5 L/min, 10 mm distance between sample and LTP probe, 5 mm distance between sample and MS inlet. For DESI measurement, the urine was 10× diluted with methanol and deposited on PTFE sheet and allowed to dry. Experiment conditions for DESI includes 150 psi nitrogen gas, 4.5 kV spray voltage, methanol/water (50:50, v:v) flow rate 3 μL/min, 5 mm distance between sample and DESI probe, 1 mm distance between sample and MS inlet.

Results

Figure 37A:
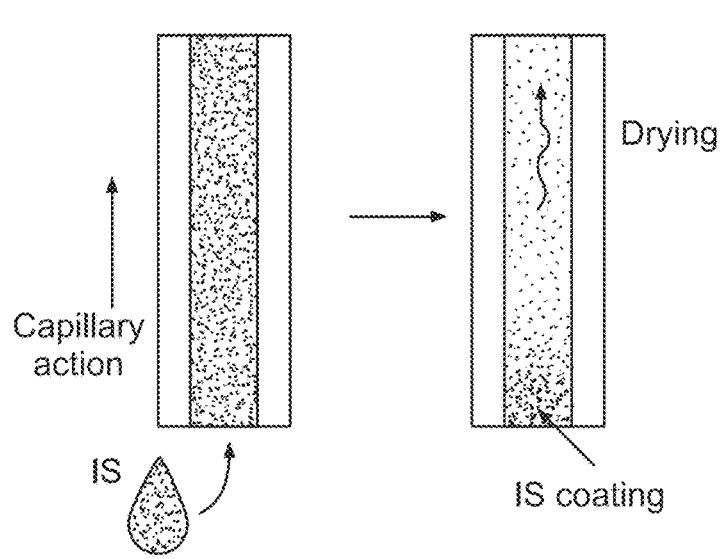
FIG. 37, panel A shows a sampling glass capillary (0.4 mm I.D., about 8 mm long) that was prepared by filling it with an internal standard solution through capillary action and drying in air to form an internal standard coating on its inner surface.
Figure 37B:
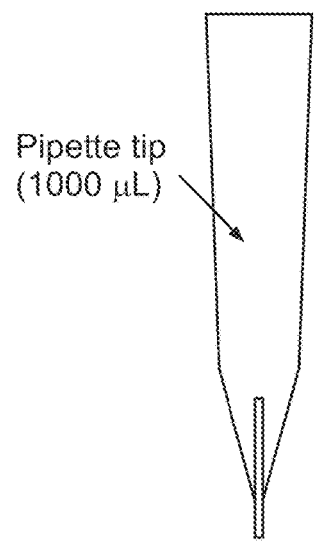
Figure 37C:
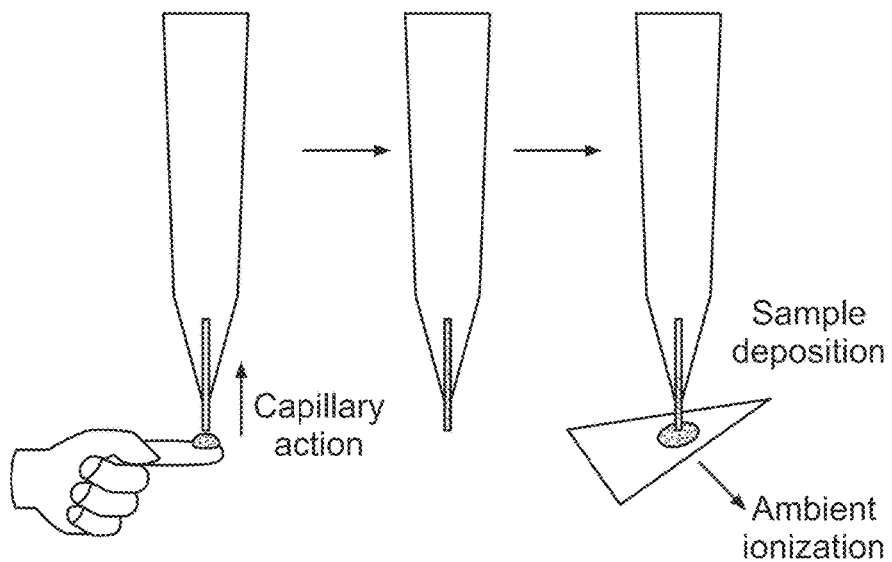
Figure 38B:
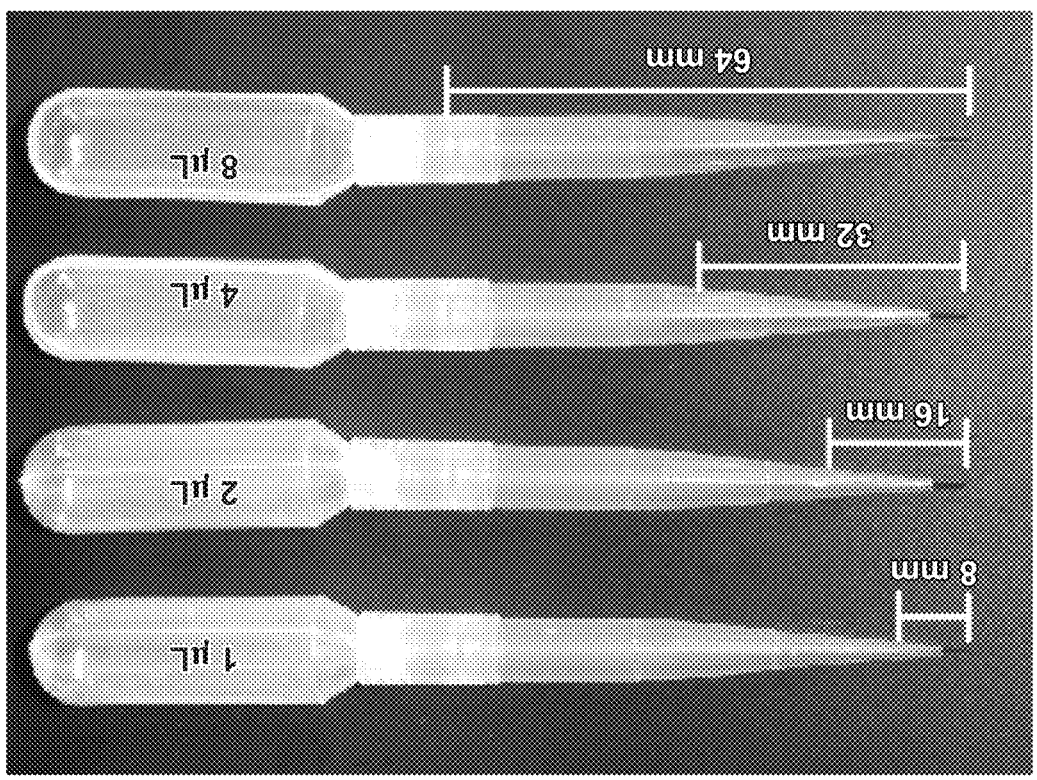
FIG. 38, panel A is a photograph showing sampling capillaries with different sampling volumes (from left to right, 1, 2, 4, 8 µL).
Figure 38A:
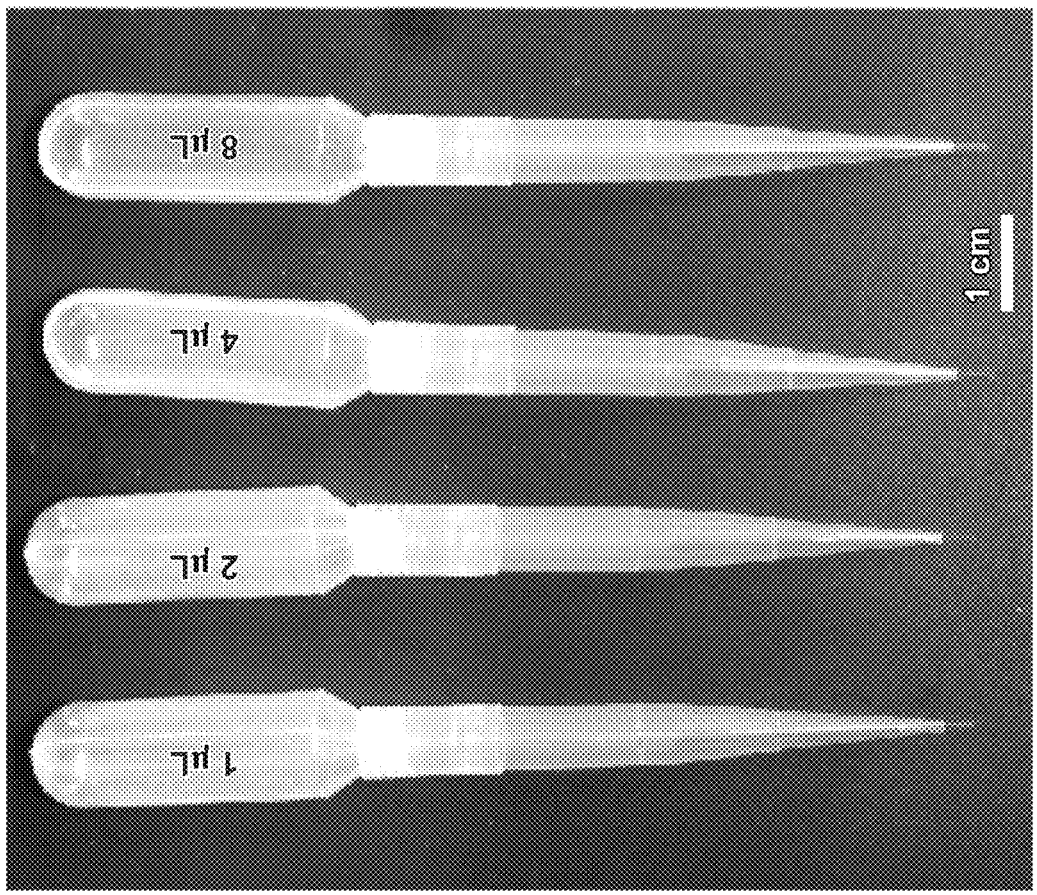

A sampling capillary was prepared for taking about 1 μL liquid sample while mixing internal standard from the walls of the capillary into the sample at an accurate concentration without requiring the use of normal in-lab procedures. The sampling capillary was fabricated by cutting glass capillaries (0.4 mm I.D., 75 mm long) into ~8 mm long sections then a coating procedure was developed to immobilize the internal standard onto the inside wall of the capillary sections. As shown in FIG. 37 panel A, one end of the capillary was touched to a bulk internal standard solution (e.g., methanol solution) and the capillary was filled by capillary action so that the total volume of the solution matched the capillary volume. The capillary was then held in a vertical position in air at 60° C. for 5 min (Table 1 below provides a characterization of drying time) while the solvent was dried. The chosen temperature was close to the boiling point of methanol (65° C.) while low enough to avoid the decomposition of the internal standard. A 1000 μL plastic pipette tip was used as a holder for easy handling of the sampling capillary (FIG. 37 panel B). The pipette tip also helped to apply a pneumatic pressure to push the viscous samples out of the capillary by using an air displacement pipette or a plastic bulb (FIG. 38 panels A and B). When used for taking liquid samples as shown in FIG. 37 panel C, the sampling capillary already coated with internal standard is filled with sample solution again through capillary action and in a volume that matches the internal volume of the capillary. As this is done the internal standard dissolves from the walls and mixes into the liquid sample. The concentration of the internal standard introduced into the sample is well controlled since the volumes of the internal standard solution and sample are both regulated by the capillary volume.

TABLE 1

Drying time for coating the capillary using methanol solution containing internal standard; oven temperature, 60° C.

| | For methanol | | | |
|---|---|---|---|---|
| Volume (μL) | 1 | 2 | 4 | 8 |
| Drying time (s) | 106 ± 3 | 211 ± 3 | 310 ± 8 | 796 ± 58 |

An important aspect of dispensers of the invention is that an accurate capillary length is not required. Rather, the volumes of internal standard solution and liquid sample are both fixed by the capillary volume, regardless of any variation in the actual volume. This is a self-regulating feature of devices of the invention. Besides that, the organic solvent used for dissolution of internal standard is completely removed during the drying process, minimizing matrix effects due to solvent.

Figure 39A:
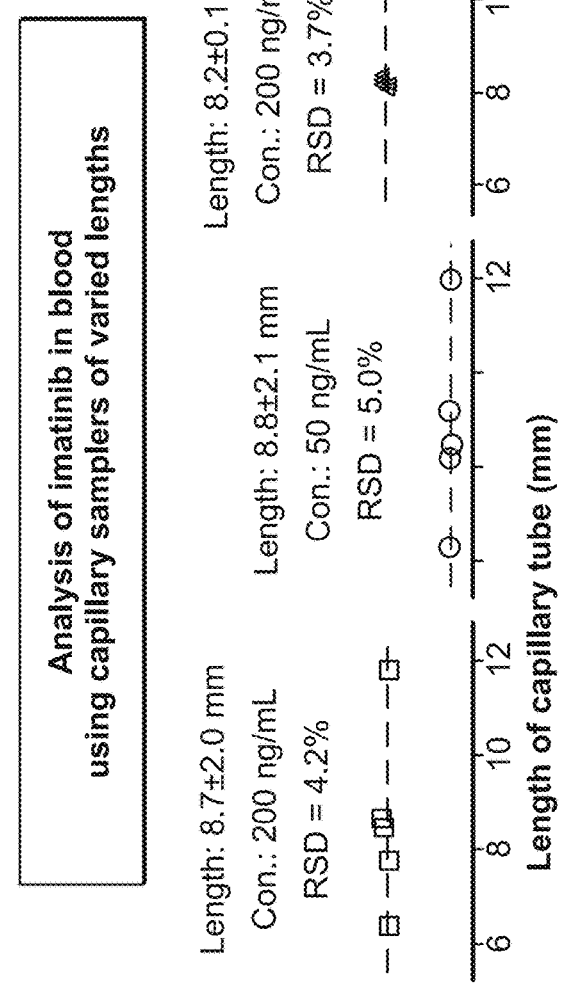
FIG. 39 panel A shows Imatinib measurements in blood (1000, 200, 50 and 200 ng/mL for each set) using sampling capillaries of varied lengths. Capillaries are coated with imatinib-d8 (100 ng/mL) as internal standard. Dashed lines are theoretical concentrations. The RSDs of measured concentration of imatinib with each set of capillaries are noted (n=5).
Figure 39B:
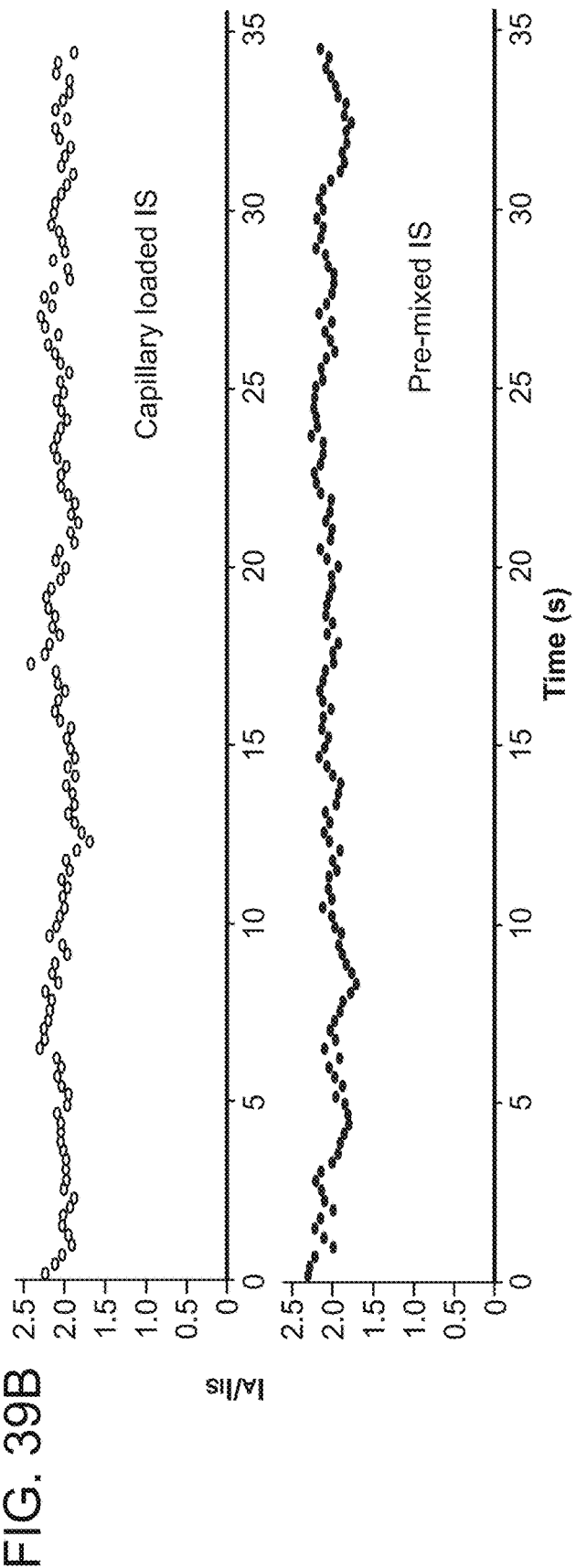

FIG. 39 panels A-B show the analysis of imatinib in blood at different concentrations using capillaries coated with imatinib-d8 as internal standard. Capillaries of different lengths (6-12 mm, corresponding to 0.75-1.5 µL in volume) were used for this test. The variations in capillary length for the first three sets are around 25% (RSD, n=5), while the variations of measured concentration of imatinib obtained with these capillaries are only ~5% (RSD, n=5). This value is comparable to that obtained with the fourth set (RSD of measured concentration, 3.7%, n=5), in which the lengths were much more tightly controlled (RSD 2.4% in capillary length, n=17).

For evaluation, the sampling capillary was used for quantitative analysis of imanitib in blood with paper spray mass spectrometry. Paper spray mass spectrometry is described herein and is an ambient ionization method that is a fast and convenient means of quantitative analysis of therapeutic drugs in blood. Good sensitivity and dynamic range as well as high reproducibility have been obtained for quantitation of a set of oncology drugs in blood. It is preferred to use a streamlined protocol for paper spray MS for point-of-care (POC) analysis.

While good quantitative analysis has been achieved by mixing the internal standards into the blood before a small amount of sample (several microliters) is loaded onto the paper substrate for paper spray MS, this sample preparation procedure requires the skill set typical of an analytical chemist and a relatively large amount of blood (hundreds of microliters). Embodiments herein show pre-printing the internal standards onto the paper substrate. This only requires the operator to load blood of a fixed volume onto the paper. The internal standard already on the paper and the analyte in the applied blood sample mix and allow quantitative measurements. Adequate accuracy in quantitation with RSD values smaller than 15% has been achieved using this method. Although adequate limits of quantitation (LOQs) have been obtained with blood of volumes less than 1 µL, 15 µL blood is typically loaded onto the paper substrate to avoid significant variations in blood volume during pipetting.

Figure 40A:
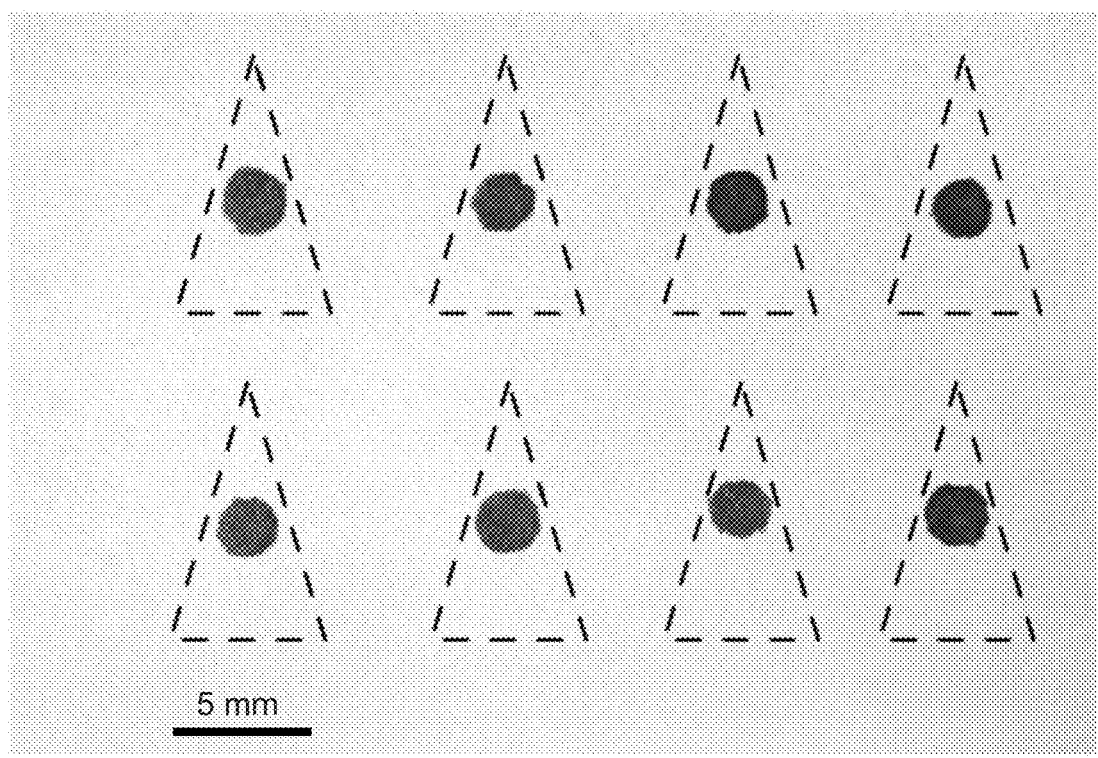
FIG. 40 panel A shows array of blood spots prepared on chromatography paper using sampling capillaries. Paper triangles were cut out along the dash lines and used for paper spray ionization. RSD of the area of the blood spots: 7.7%, n=8.
Figure 40B:
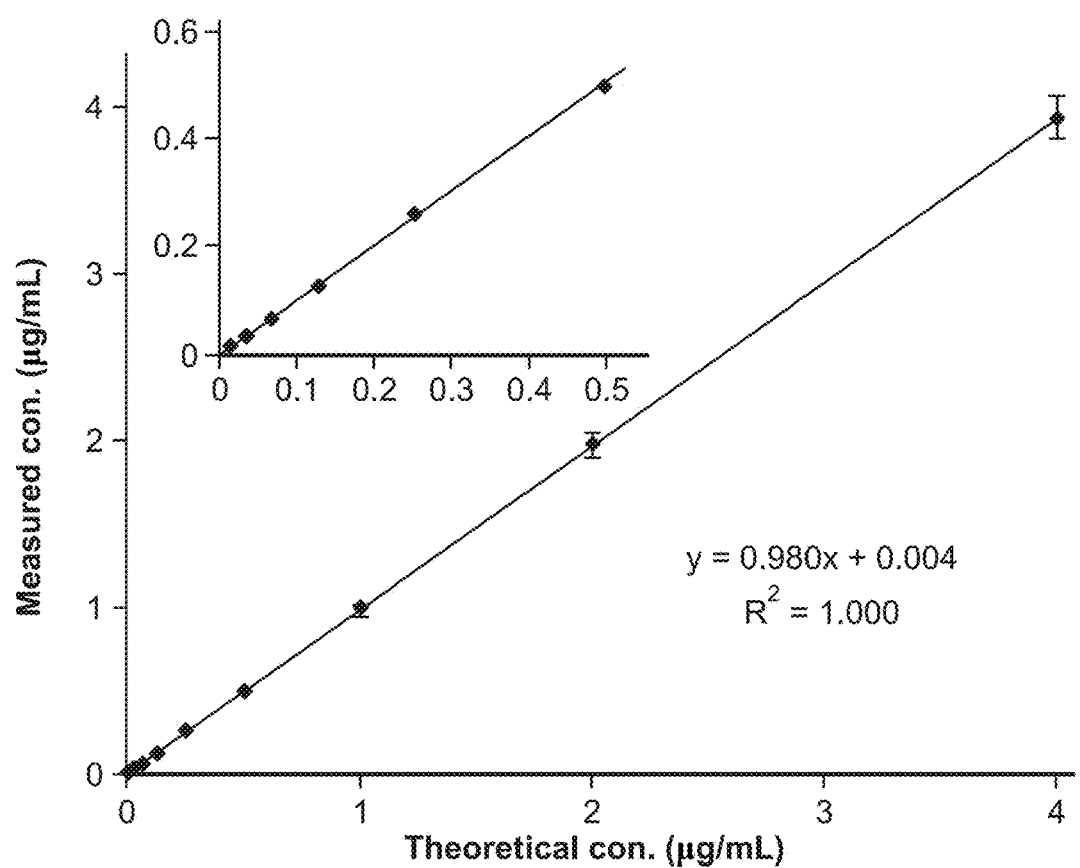

Using devices described herein, the blood sample was placed on a glass slides and sampled from there to simulate finger-stick blood sampling. The blood in the capillary was transferred onto a paper substrate by allowing the end of the capillary to touch the paper. A dried blood spot (DBS) array was easily be generated on paper as shown in FIG. 40A. Paper triangles cut out along the dashed lines were used for paper spray MS to analyze the chemicals in blood. Quantitative analysis of imatinib in blood with the concentration varying from 10 ng/mL to 4 µg/mL was successfully performed with RSD of 3-5% (RSD, n≥3) for the entire range of concentrations (FIG. 40B).

Using of devices of the invention to introduce internal standard to a sample was compared to traditional methods of premixing internal standard into blood. A comparison was made between the dried blood spots prepared by pipetting 1 µL blood containing imatinib at 200 ng/mL with imatinib-d8 premixed at 100 ng/mL and those prepared by direct sampling using the coated capillaries (imatinib at 200 ng/mL in blood, imatinib-d8 at 100 ng/mL in standard solution for coating). The MS/MS ion current of imatinib (m/z 494 to m/z 394) and imatinib-d8 (m/z 502 to m/z 394) were measured with paper spray MS and the ratio of these two signals was plotted as a function of paper spray time in FIG. 40 panel B. Comparable stability in ratio was observed for both methods.

The recovery of coated internal standard was also investigated. To evaluate the recovery of internal standard eluted during the sampling process, sampling capillary coated with 0.1 ng imatinib-d8 were eluted with blood spiked with 120 ng/ml imatinib. The elution was performed exactly the same as blood test with paper spray ionization as described previously. The tested recovery of imatinib-d8 is 99.6±6.7% (n=5), indicating most of the internal standard was spiked into the blood during the sampling process.

Devices and methods of the invention can be used with any analytical technique, for example, chromatography techniques, such as high performance liquid chromatography (HPLC), mass spectrometry techniques, and other analytical techniques.

In particular embodiments, devices and methods of the invention are used for preparation of a sample for analysis by mass spectrometry. Any mass spectrometry technique known in the art may be used with methods of the invention. Exemplary mass spectrometry techniques that utilize ionization sources at atmospheric pressure for mass spectrometry include electrospray ionization (ESI; Fenn et al., Science, 246:64-71, 1989; and Yamashita et al., J. Phys. Chem., 88:4451-4459, 1984); atmospheric pressure ionization (APCI; Carroll et al., Anal. Chem. 47:2369-2373, 1975); and atmospheric pressure matrix assisted laser desorption ionization (AP-MALDI; Laiko et al. Anal. Chem., 72:652-657, 2000; and Tanaka et al. Rapid Commun. Mass Spectrom., 2:151-153, 1988). The content of each of these references in incorporated by reference herein its entirety.

Exemplary mass spectrometry techniques that utilize direct ambient ionization/sampling methods including desorption electrospray ionization (DESI; Takats et al., Science, 306:471-473, 2004 and U.S. Pat. No. 7,335,897); direct analysis in real time (DART; Cody et al., Anal. Chem., 77:2297-2302, 2005); Atmospheric Pressure Dielectric Barrier Discharge Ionization (DBDI; Kogelschatz, Plasma Chemistry and Plasma Processing, 23:1-46, 2003, and PCT international publication number WO 2009/102766), Low Temperature Plasma (PCT/US2009/033760), and electrospray-assisted laser desoption/ionization (ELDI; Shiea et al., J. Rapid Communications in Mass Spectrometry, 19:3701-3704, 2005). The content of each of these references in incorporated by reference herein its entirety. In certain embodiments, the mass spectrometry technique is a paper spray based technique as described herein.

Figure 41A:
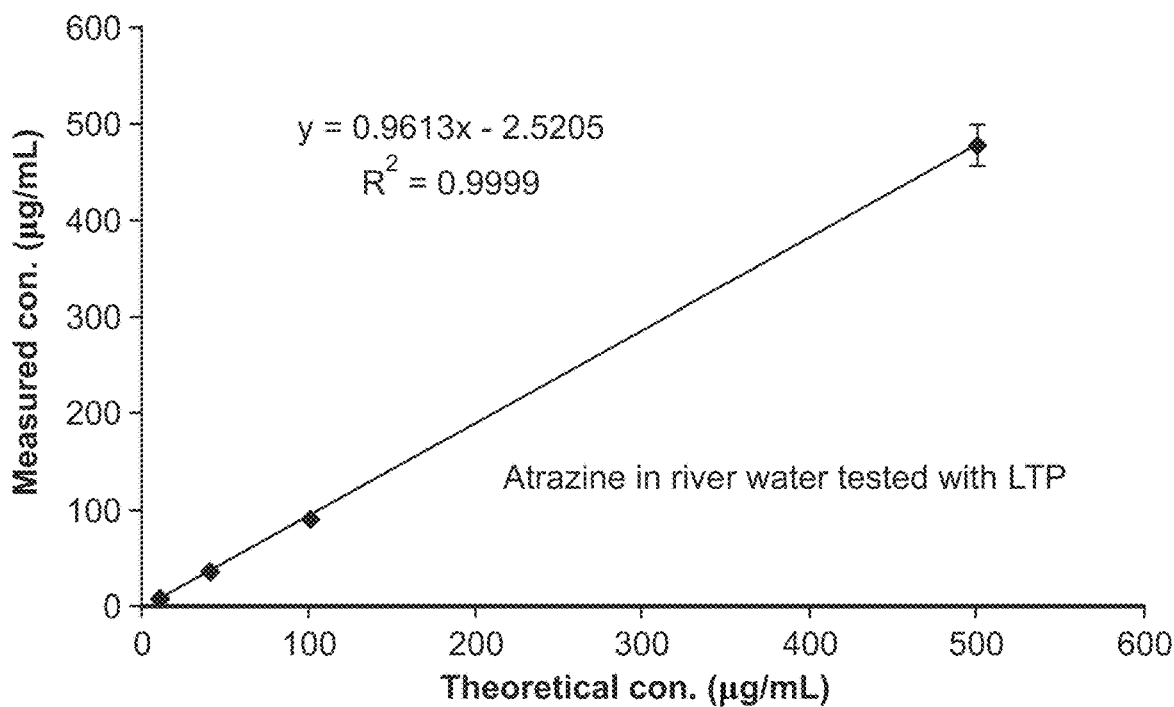
FIG. 41 panel A shows quantitative analysis of complex mixtures with different ambient ionization methods. Dried sample spots prepared on non-porous materials. a) Analysis of atrazine in river water (10-500 ng/mL) using LTP, dried sample spot on PTFE.
Figure 41B:
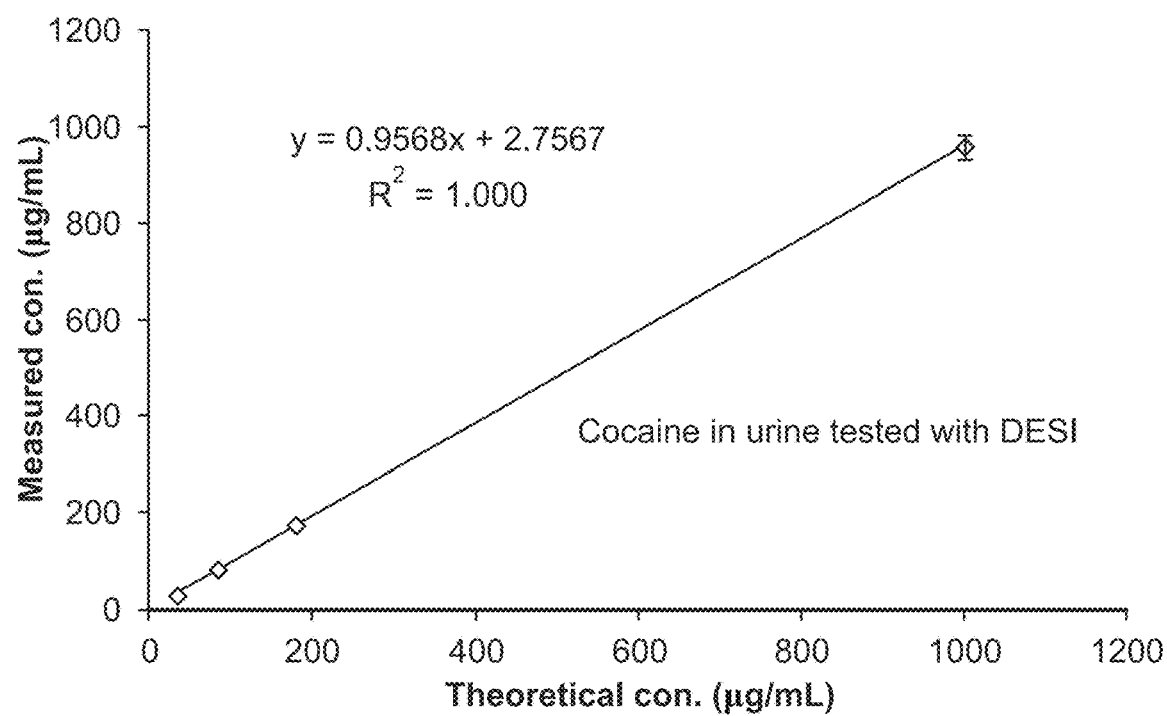

For example, devices of the invention were used for quantitative analysis of river water samples with low temperature plasma (LTP) and urine samples with desorption electrospray ionization, respectively. For LTP analysis, river water samples containing atrazine at 10-500 ng/mL were deposited on a glass slide, allowed to dry and analyzed with a LTP probe (FIG. 41, panel A). For DESI analysis, diluted urine samples containing cocaine at 33-1000 ng/mL were deposited on a PTFE sheet, allowed to dry and analyzed with DESI (FIG. 41 panel B). Sample amounts of about 1 µL were used for all tests and RSDs better than 5% were achieved for all quantitation measurements (Table 2).

TABLE 2

Using sampling capillaries for quantitative analysis of atrazine in river water with LTP and cocaine in urine with DESI, respectively.

| Samples | Analyte Con. (ng/mL) | Mean analyte/IS (n = 5) | Standard deviation | Relative standard deviation (%) |
|---|---|---|---|---|
| Atrazine | 500 | 4.79 | 0.23 | 4.8 |
| 1 μL river water | 100 | 0.91 | 0.025 | 2.7 |
| (IS: 100 ng/mL atrazine-d 5) | 40 | 0.37 | 0.012 | 3.2 |
| LTP | 10 | 0.08 | 0.006 | 7.5 |
| Cocaine | 1000 | 9.59 | 0.23 | 2.4 |
| 1 μL urine | 180 | 1.76 | 0.034 | 1.9 |
| (IS: 100 ng/mL cocaine-d 3) | 80 | 0.84 | 0.016 | 1.9 |
| DESI | 30 | 0.31 | 0.010 | 3.2 |

By varying the length of the capillary, a series of glass capillaries was fabricated with sampling volumes varying from 1 μL to 8 μL (FIG. 38 panels A-B). Most liquids are able to be collected and dispensed with these capillaries, including aqueous solutions, organic solvents, and biofluids (FIG. 42, panels A-C). Characterization of the sampling process for methanol, urine, blood and serum was performed (FIG. 42, panels A-C). For urine, methanol and serum, sampling times are around 1 s for an 8 μL capillary but shorter for smaller capillary (Table 3 below). For blood, the sampling time varies from ~15 s for an 8 μL capillary to less than 0.5 s for a 1 μL capillary, which is fast enough for taking finger-stick blood for POC analysis. Dispensing times for different liquids have also been measured. For urine, methanol and serum, liquids can be simply dispensed onto paper by capillary action due to the porous nature of paper. The dispensing time is about an order of magnetite longer than the loading time for each liquid (Table 3 below). When dispensing blood, the micropores on paper could be blocked by blood cells. Using a bulb on the dispenser holder to put some pressure through the capillary can help to complete the blood transfer within one or two seconds.

TABLE 3

Sample collection time and dispensing time for different liquids using capillary action.

| | Urine | Methanol | Blood | | | | Serum | | | |
|---|---|---|---|---|---|---|---|---|---|---|
| Viscosity (mPa · s, 20° C.) | 0.8 | 0.59 | ~10 | ~10 | 3-4 (37° C.) | 3-4 (37° C.) | 1.4-1.8 | | | |
| Surface tension (mN/m, 20° C.) | ~66 | 22.6 | ~61 | ~61 | ~58 (37° C.) | ~58 (37° C.) | ~59 | ~59 | ~53 (37° C.) | ~53 (37° C.) |
| Volume (μL) | 8 | 8 | 8 | 4 | 2 | 1 | 8 | 4 | 2 | 1 |
| Loading time | 1.0 ± 0.1 | 1.2 ± 0.1 | 15.4 ± 0.8 | 3.8 ± 0.3 | 1.2 ± 0.1 | <0.5 | 1.0 ± 0.1 | <0.5 | <0.5 | <0.5 |
| Dispensing time (s) | 13.8 ± 0.6 | 6.4 ± 0.3 | N/A | | | | 11.2 ± 0.7 | 4.9 ± 0.7 | 2.7 ± 0.1 | 1.2 ± 0.1 |

[a.] A smearing action or pressurizing is required to dispense blood.

In conclusion, a method using internal standard coated capillary has been developed for quantitative measurement of compounds in liquid samples. Accurate quantitation can be achieved with a sample volume at 1 μL and traditional laboratory procedures of sample preparation are not required. This method bridges the crude samples and the ionization sources in a simple fashion and with user-friendly procedures. This method also addresses two fundamental issues related to chemical analysis in quantitation: 1) how to collect sample in an easy, fast and accurate manner; 2) how to quantitatively spike internal standards into the collected samples. The capillaries loaded with internal standards are stable at 4° C. for at least days (FIG. 43). As such, it is suitable for point-of-care applications. High throughput processes for analysis can also be developed using this method for preclinical study, where quantitative measurement must be performed with limited amounts of biofluidic samples from small animals.

What is claimed is:

1. A method for analyzing a sample comprising:
   preparing a mixture of a sample with a controlled amount of an internal standard, wherein the preparing step comprises introducing the sample to a capillary on which walls of the capillary comprise the internal standard;
   contacting the mixture to a porous substrate;
   applying a high voltage to the porous material to generate ions of an analyte and ions of the internal standard that are expelled from the porous material; and
   analyzing the expelled ions.

2. The method according to claim 1, wherein the porous substrate is kept separate from a flow of solvent.

3. The method according to claim 2, further comprising applying a solvent to the porous substrate.

4. The method according to claim 3, wherein the solvent assists in transport of the sample through the porous substrate.

5. The method according to claim 3, wherein the solvent minimizes salt and matrix effects.

6. The method according to claim 1, wherein analyzing comprises providing a mass analyzer to generate a mass spectrum of analytes in the sample.

7. The method according to claim 1, wherein the sample is a biological sample.

8. The method according to claim 7, wherein the biological sample is a blood sample or a urine sample.

9. The method according to claim 1, further comprising quantifying a target analyte in the sample.

10. The method according to claim 1, wherein a volume of the capillary regulates a volume of the sample and a volume of the internal standard that comprise the mixture.

11. The method according to claim 1, wherein the sample comprises a volume of about 1 µL or less.

* * * * *